(12) United States Patent
Myette

(10) Patent No.: US 7,767,420 B2
(45) Date of Patent: Aug. 3, 2010

(54) HEPARAN SULFATE GLYCOSAMINOGLYCAN LYASE AND USES THEREOF

(75) Inventor: James Myette, Waltham, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 593 days.

(21) Appl. No.: 11/265,908

(22) Filed: Nov. 3, 2005

(65) Prior Publication Data

US 2007/0098708 A1   May 3, 2007

(51) Int. Cl.
*C12P 19/28* (2006.01)
*C12N 9/00* (2006.01)
*C12N 9/88* (2006.01)
*C12N 1/20* (2006.01)
*C12N 15/00* (2006.01)
*C07H 21/04* (2006.01)

(52) U.S. Cl. .................. 435/85; 435/232; 435/252.3; 435/320.1; 536/23.2

(58) Field of Classification Search .................. 435/85, 435/183, 232, 252.3, 320.1; 536/23.2
See application file for complete search history.

(56) References Cited

U.S. PATENT DOCUMENTS

| | | | |
|---|---|---|---|
| 5,145,778 | A | 9/1992 | Bellamy et al. |
| 5,455,162 | A | 10/1995 | Bellamy et al. |
| 5,714,376 | A | 2/1998 | Sasisekharan et al. |
| 5,830,726 | A | 11/1998 | Sasisekharan et al. |
| 5,997,863 | A | 12/1999 | Zimmermann et al. |
| 6,217,863 | B1 | 4/2001 | Godavarti et al. |
| 6,841,375 | B2 | 1/2005 | Su et al. |
| 6,869,789 | B2 | 3/2005 | Liu et al. |
| 7,056,504 | B1 | 6/2006 | Sasisekharan et al. |
| 2001/0006635 | A1 | 7/2001 | Bennett et al. |
| 2001/0034043 | A1 | 10/2001 | Su et al. |
| 2004/0018187 | A1 | 1/2004 | Denholm et al. |
| 2005/0153398 | A1 | 7/2005 | Su et al. |
| 2005/0191288 | A1 | 9/2005 | Bennett et al. |
| 2005/0233402 | A1 | 10/2005 | Liu et al. |
| 2006/0067928 | A1 | 3/2006 | Liu et al. |
| 2006/0105430 | A1 | 5/2006 | Sasisekharan et al. |
| 2006/0140928 | A1 | 6/2006 | Bennett et al. |
| 2006/0182734 | A1 | 8/2006 | Liu et al. |
| 2006/0183713 | A1 | 8/2006 | Liu et al. |
| 2007/0134226 | A1 | 6/2007 | Myette et al. |

FOREIGN PATENT DOCUMENTS

| | | |
|---|---|---|
| CN | 1429913 | 7/2003 |
| CN | 1699424 | 11/2005 |
| CN | 1712418 | 12/2005 |
| CN | 1757739 | 4/2006 |
| DE | 10207708 | 9/2003 |
| EP | 0370958 | 5/1990 |
| EP | 0610408 | 8/1994 |
| EP | 0769961 | 5/1997 |
| EP | 0852491 | 7/1998 |
| EP | 1552846 | 7/2005 |
| KR | 100206182 | 4/1999 |
| KR | 100257168 | 2/2000 |
| KR | 2001055115 | 7/2001 |
| KR | 2002046293 | 2/2002 |
| WO | WO 93/08289 | 4/1993 |
| WO | WO 97/16556 | 5/1997 |
| WO | WO 00/12726 | 3/2000 |
| WO | WO 01/53474 | 7/2001 |
| WO | WO 01/66772 | 9/2001 |
| WO | WO2007/056218 | 5/2007 |

OTHER PUBLICATIONS

Chica et al. Curr Opin Biotechnol. Aug. 2005;16(4):378-84.*
Seffernick et al. J Bacteriol. Apr. 2001; 183 (8): 2405-10.*
Witkowski et al. Biochemistry. Sep. 7, 1999; 38(36): 11643-50.*
Rieger et al. Glossary of Genetics (1991), p. 16.*
Sasisekharan et al. Proc Natl Acad Sci U S A. Apr. 15, 1993;90(8):3660-4.*
Xu et al. Accession Q89YQ6, Jun. 1, 2003.*
Hedner et al. Semin Thromb Hemost. 2000;26 Suppl 1:23-9.*
Xu et al. Accession Q89YS4, Jun. 1, 2003.*
Venkataraman et al. Science. Oct. 15, 1999;286(5439):537-42.*
Pojasek et al. Biochemistry. Apr. 11, 2000;39(14):4012-9.*
Sen et al. Appl Biochem Biotechnol. Dec. 2007;143(3):212-23.*
Ahn, M.Y., K.H. Shin, et all. "Characterization of a Bacteroides Species from Human Intestine that Degrades Glycosaminoglycans", *Can J Microbiol*, 44(5):423-9, (1998).
Kim, B. T., S.W. Hong, et al. "Purification and Characterization of Acharan Sulfate Lyases. Two Novel Heparinases, from Bacteroides Steroris HJ-15", *Eur J Biochem*, 268(9):2635-41, (2001).
Kim, W.S., B. T. Kim, et al. "Purification and Characterization of Heparin Lyase I from Bacteroides Stercoris HJ-15", *J Biochem Mol Biol* 37(6):684-90, (2004).
Sonnenburg, j.L., J. Xu, et al. "Glycan Foraging in vivo by an Intestine-adapted Bacterial Symbiont", *Science*, 307(5717): 1955-9, (2005).
Xu, J., M.K. Bjursell, et al. "A Genomic View of the Human-Bacteroides Thetaiotamicron Symbiosis", *Science*, 299(5615):2074-6, (2003).
GenBank Accession No. AE016946, (Priority Date:: Mar. 28, 2003); 905 pages.
GenBank Accession No. AAO79762, (Priority Date:: Mar. 28, 2003); 2 pages.
GenBank Accession No. AAO79780, (Priority Date:: Mar. 28, 2003); 2 pages.

(Continued)

*Primary Examiner*—Christian L Fronda
(74) *Attorney, Agent, or Firm*—Lando & Anastasi, LLP

(57) ABSTRACT

The invention provides recombinant *B. thetaiotaomicron* HSGAG lyase polypeptides. The invention also provides nucleic acid molecules encoding such polypeptides, recombinant expression vectors containing *B. thetaiotaomicron* HSGAG lyase nucleic acid molecules, and host cells into which the expression vectors have been introduced. Characterization, diagnostic and therapeutic methods utilizing compositions of the invention are also provided.

9 Claims, 12 Drawing Sheets

OTHER PUBLICATIONS

GenBank Accession No. AE015928, (Priority Date:: Mar. 28, 2003); 905 pages.

Byung-Taek Kim et al., "Purification and Characterization of a Novel Heparinase from *Bacteroides stercoris* HJ-15[1]", J. Biochem. vol. 128, pp. 323-328 (2000).

Extended European Search Report from corresponding European Application No.: 506836937.0 dated Aug. 20, 2009.

Riley T V et al., "Heparinase Production by Bacteroides"-SPP, vol. 25, No. 99-100, pp. 141-148, 1984.

Riley T V et al., "Heparinase Production by Anaerobic Bacteria", vol. 40, No. 4, Apr. 1987.

Myette James R et al. "The Heparin/Heparan Sulfate 2-0-Sulfatase From Flavobacterium Heparinum. Molecular, Cloning, Recombinant Expression, and Biochemical Characterization", vol. 278, No. 14, pp. 12157-12166, Apr. 4, 2003.

* cited by examiner

```
   1 GACAAACGAAAGGCAGCCGTAAGGGTTGCCTTTCGTATTTTTGCACCGTCGATAAACTTAATACCGGATAGAATGAAAAA
  81 ATACATTTGGTTATTTATGATGGCGGCAGGATGCACGATGCACCGATGCTCAGACTGAAAATACGCAAACACTGATGC
 161 CACTCACCGAACGGTAAACCTACAGGCTGACTCTGCACGTATCAACCAGATTATTGACGGTTGCTGGGTAGCTGTCGGG
 241 ACGAATAAACCTCATGCCATTCAGCGTGAAGGTTATGCGACGTTTATCGAAAGGAGAAACGAAAGCGTGCCGAGTTTTCATATTGCTATGCAACTTCCG
 321 TGAAGACAATACACTGGAAGGTTATGCGACGTTTATCGAAAGGAGAAACGAAAGCACAGATCACAAAGACAGTTATCATCACGGAAGGGAGCT
 401 ACGATTTCAGGGAAGTTCCCGCGACTATGAGTTTTCGGTTTATATTCCTTCTCTTTAGACAGCAATGTCTCCACCATCTT
 481 TGTCCGCAAGGACGGAATGCCGACCGGTCCAGACGCTGGTCCAGAAGAATGTCGGACACGAAAAAGCCCAGACTGTTGACGAAT
 561 TGCCCAATGGCACGGAATGCCGACCGGTCCAGACGCTGGTCCAGAAGAATGTCGGACACGAAAAAGTGGCCAGACTGTTGACGAAT
 641 TTGTAGAACTGGAAAAAACGACCTTCTTCAAAAAGATGTCGGAACACGAAAAACCAACGGATGGTTGGTTGAACAGGGAGGATACCC
 721 CCGGTGAAAGATAAAAATGGAAAACTGTATATAAGGCAGGAAAAACTCCGACCGTAAATGGCTGACAGACAAAGATG
 801 GCCATTGGCATTCGGATTTTCCGGAGGACTGTTTTATATCAAAGCAAACTCCGACTTCGAATACAAGGCATCCACCATTGCCTAC
 881 ACCGTTGCAATGCAAACCCGGAAAGACGCCGTTATGAAACGCTGACTTCGTGTCCATATCGACTGGACGGTCTATGCAAGGA
 961 AAATTACCTTTTGCCGATTTCCCGAAGACTGTGAACGATGCTGGATTACTTCCGTGTCCATATCGACTGGACGGTCTATGCAAGGA
1041 AGCGGAAACGATTGTGAAGAGATTCTGATTGGACGTAACGACGAAGACGTATTACTTTAAGTTCGGAATTTACCGCGTAGGT
1121 TTGTCGATAATGAGAAGATTCTGATTGGACGTAACGACGAAGACGGTATTACTTTAAGTTCGGAATTTACCGCGTAGGT
1201 GATAGTACCGTTCCCGTTGCTACAATCTCGCAGGATATTCGGAAAGATAA
```

FIG. 1A

```
  1  MKKYILVIYM MAAGCTMLTA QTKNTQTLMP LTERVNVQAD SARINQIIDG CWVAVGTNKP
 61  HAIQRDFTNL FDGKPSYRFE LKTEDNTLEG YAKGETKGRA EFSYCYATSD DFRGLPADVY
121  QKAQITKTVY HHGKGACPQG SSRDYEFSVY IPSSLDSNVS TIFAQWHGMP DRTLVQTPQG
181  EVKKLTVDEF VELEKTTFFK KNVGHEKVAR LDKQGNPVKD KNGKPVYKAG KPNGWLVEQG
241  GYPPLAFGFS GGLFYIKANS DRKWLTDKDD RCNANPGKTP VMKPLTSEYK ASTIAYKLPF
301  ADFPKDCWIT FRVHIDWTVY GKEAETIVKP GMLDVRMDYQ EQGKKVSKHI VDNEKILIGR
361  NDEDGYYFKF GIYRVGDSTV PVCYNLAGYS ER
```

FIG. 1B

```
BT Hlyase I     1   MKKY VIYM AAGCTM TAQTKNTQTLMPLTE        RINQ  GC   T NK
FH heparinaseI  1   MK QI YLIVLQQ--LF CSAYAGQKKSGN PY       KQKA  NK  AWG I
consensus       1   MKK-IL-i-mm--gc--L-----n------l---RVNVQADSAr---IID--WVAVG-NKP BT Hlyase I    61   H  R  FTNL D                 K         A F  C    SD   RGL AD
FH heparinaseI 59   Y L Y DKLR N               A   S      A      T L  S    N   KKF PS
consensus      61   -AiQ-D----F-GKPSYRFELK-EDNtLEGYA-GETKGR-E-SY-YATs-DFr--P--VY BT Hlyase I   121    K  IT     H   A P    D  E         LDS VS         M D    Q  Q
FH heparinaseI 119   N  KL     Y   I  E      S T        FPD A          A S    A  E
consensus     121   Q-AQ--KTVYH-GKG-C-QGSSR-Y-FSVYIPSS---N-STIFAQWHG-P-RTLV-TP-G BT Hlyase I   181    K  TVD   E EKTTF      G      ARLDKQGNPV   N  PV K        L
FH heparinaseI 179    T  S E   A YDRMI       A D   E        D   IT V         K
consensus     181   EvK-LtvdEFv-L-----FKKNvgHeKV-rldkqgnpvKDK-GK---Y-AGKPNGW-VEQG BT Hlyase I   241    P       G L          K       DD C     GK P    L       A     L
FH heparinaseI 231     T       K Y         Q       A  N   ENSE     YS     T      KM
consensus     241   GYP-LAFGFS-G-FYIKANSDR-WLTDK-DR-NANP--t-VMKP-tSEYK-STIAYKIPF BT Hlyase I   301    D        R H   V     E       M    R D QE G KVSK    DNEK
FH heparinaseI 291   Q         D A   K     N   L   K    M T TKNK PQKA    N QE
consensus     301   A-FPKDCWITF-V-IDWT-YGKEA-TIvKPG-LDV-M-Y--q-K----HIV-n---ILIGR BT Hlyase I   361    E           D      C    A    R--
FH heparinaseI 351    D           N      T    S      TAR
consensus     361   NDeDGYYFKFGIYRVG-STVPV-YNL-GYSE-ar
```

1    ATGAAAAAATACATTTTGGTTATTTATATGATGGCGGCAGGATGCACGATGCTGACTGCTCAGACTGCTCAGAAAAATACGCAAAC
81   ACTGATGCCACTCACCGAACGGGTAAACGTACAGGCTGAACGTGACTCTGCACGTATCAACCAGATTATTGACGGTTGCTGGGTAG
161  CTGTCGGGACGAATAAACCTCATGCCATTCAGCGTGATTTTACCAACCTGTTTGATGGCAAGCCCTCCTATCGCTTTGAA
241  CTCAAAACTGAAGACAATACACTGGAAGGTTATGCCGACGTTTATGCCGACGTTTATCGAAAGGAGAAACGAAAGGACGTGCCGAGTTTTCATATTGCTATGC
321  AACTTCCGACGATTTCAGGGGATTACCTGCCGACTATGAGTTTTCGGTTTATATTCCTTCTTTAGACAGAATGTCTCC
401  AGGGAGCTTTGTCCGCAATGGCACGGAAGTTCCCGCGAATGCCCGACCGACGCTGGTCCAGACTCCTCAGGGCGAGGTGAAGAAACTGACTGT
481  ACCATCTTTGCCCAATGGCACGGAAGTTCCCGCGAATGCCCGACCGACGCTGGTCCAGACTCCTCAGGGCGAGGTGAAGAAACTGACTGT
561  TGACGAATTTGTAGAACTGGAAAAAACGACCTTCTTCAAAAAGAATGTCGGACACGAAAAAGTGGCCAGACTGGATAAAC
641  AAGGTAATCCGGTGAAAGATAAAAATGGAAAACCTGTATATAAGGCAGGAAAACCCAACGGATGGTTGGTTGAACAGGGA
721  GGATACCCGCCATTGGCATTCGGATTTTCCGGAGGACTGTTTTATATCAAAGCAAACTCCGACCGTAAATGGCTGACAGA
801  CAAAGATGACCGTTGCAATGCAAACCCGGAAAAGACAGCGCCCGTTATGAAAGACTGCTGGATTACTTTCCGTGTCCATATCGACTGGACGGTCTAT
961  TTGCCTACAAATTACCTTTTGCCGATTTCCCGAATTCCCGAAAGACTGCTGGATTACTTTCCGTGTCCATATCGACTGGACGGTCTAT
1041 GGCAAGGAAGCGGAAACGATTGTGAAACCGGGCATGCTGGATGTACGGATGGATTATCAGGAGCAAGGTAAGAAGTGAG
1121 CAAACACATTGTCGATAATGAAGAGATTCTGATTGGACGTAACGACGAAGACGGGTATTACTTTAAGTTCGGAATTTACC
1201 GCGTAGGTGATAGTACCGTTCCCGTTTGCTACAATCTCGCAGGATATTCGGAAAGATAA

FIG. 3A

```
MLTAQTKNTQ TLMPLTERVN VQADSARINQ IIDGCWVAVG TNKPHAIQRD FTNLFDGKPS YRFELKTEDN
TLEGYAKGET KGRAEFSYCY ATSDDFRGLP ADVYQKAQIT KTVYHHGKGA CPQGSSRDYE FSVYIPSSLD
SNVSTIFAQW HGMPDRTLVQ TPQGEVKKLT VDEFVELEKT TFFKKNVGHE KVARLDKQGN PVKDKNGKPV
YKAGKPNGWL VEQGYPPLA FGFSGGLFYI KANSDRKWLT DKDDRCNANP GKTPVMKPLT SEYKASTIAY
KLPFADFPKD CWITFRVHID WTVYGKEAET IVKPGMLDVR MDYQEQGKKV SKHIVDNEKI LIGRNDEDGY
YFKFGIYRVG DSTVPVCYNL AGYSER
```

FIG. 3B

```
   1 CAAACACTGATGCCACTCACCGAACGGGTAAACGTACAGGCTGACTCTGCACGTATCAACCAGATTATTGACGGTTGCTG
  81 GGTAGCTGTCGGGACGAATAAACCTCATGCCATTCAGCGTGATTTTACCAACCTGTTTGATGGCAAGCCCTCCTATCGCT
 161 TTGAACTCAAAACTGAAGACAATACACTGGAAGGTTATGCGAAAGGAGAAACGAAAGGACGTGCCGAGTTTTCATATTGC
 241 TATGCAACTTCCGACGATTTCAGGGAGATTACCTGCCGACGTTTATCGAGTTTTCGGTTTATATTCCTTCTTTAGACAGTTTATCATCA
 321 CGGGAAGGGAGCTTGTCCGCAAGGAAGTTCCCGCGAATGCCCGGACTATGAGTTTTCGGTTTATATTCCTTCTTTAGACAGCAATG
 401 TCTCCACCATCTTTGCCCAATGGCACGGAATGCCCGGACGCTGGTCCAGACTCCTCAGGGCGAGGTGAAGAAACTG
 481 ACTGTTGACGAATTTGTAGAACTGGAAAGATAAAAATGGAAAACGACCTTCTCAAAAAGAATGTCGGACACGAAAAAGTGGCCAGACTGGA
 561 TAAACAAGGTAATCCGGTGAAAGATAAAAATGGCATTCGGATTTTCCGGAGGACTGTTTTATATCAAAGCAGGAAAACCCAACGATGGTTGGTTGAAC
 641 AGGGAGGATACCCGCCATTGGCAATGCAAACCCGTTATGAAGAGACGCCCGTTATGAAGAGACGCCGTTATGAAGAGACGCCGTTATGAAGAGACGCC
 721 ACAGACAAAGATGACCGTTGCAATGCAAACCCGTTATGAAGAGACGCCCGTTATGAAGAGACGCCCGTTATGAAGAGACGCCCGTTATGAAGAGACGCCCGTTATGAAGAGACGCCTGACTTCTGAATACAAGGCATC
 801 CACCATTGCCTACAAATTACCTTTTGCCGATTTCCCGAAAGACTGCTGGATTACTTTCCGTGTCCATATCGACTGGACGG
 881 TCTATGGCAAGGAAGCGGAAAACGATTGTGAAACCGGGCATGCTGGATGTAACGACGAAGACGGGTATTACTTAAGTTCGGAAT
 961 GTGAGCAAACACATTGTCGATAATGAGAAGATTCGATTGGACGTAACGACGAAGACGGGTATTACTTAAGTTCGGAAT
1041 TTACCGCGTAGGTGATAGTACCGTTCCCGTTTGCTACAATCTCGCAGGATATTCGGAAAGATAA
```

FIG. 4A

QTLMPLTERV NVQADSARIN QIIDGCWVAV GTNKPHAIQR DFTNLFDGKP SYRFELKTED NTLEGYAKGE
TKGRAEFSYC YATSDDFRGL PADVYQKAQI TKTVYHGKG ACPQGSSRDY EFSVY

```
   1 atgaataaaa cctgaaata gttgaaaag cgagtattc tcgcttctca acctggacta cccggattg
  61 tatgccaag agttgaaaag cgagtattc tcaggaaggc aaagatgagg atgccgaaa agcactgctc
 121 gagaaagtaa aagccttaca tcaggaaggc aaagatgagg atgccgaaa agcactgctc
 181 gactactacc gtgcacgtac gaatgtgaag acgccgata ttaatctgaa aaagatcact
 241 atcggcaaag aagaacagca atgggcggat gacgattga agcatacatt ctttgttcac
 301 aaagctatc agccttctta caactacgga gaagatatca actggcaata ctggccggtg
 361 aaagacaatg aactccgctg agccttgcac cgtcatgcac ggttactcc gatgggtaag
 421 gcataccgtg tatcgggtga cgagaaatat gccaaagaat gggcatacca atacatcgac
 481 tggattaaaa agaatccgtt ggtgaagatg gacaagaaag aatacgaact ggtaagtgac
 541 gtaagatta aaggcgaagt ggaaaatgta cgtttcgcat ggcgtccgct ggaagtcagt
 601 aatcgtctgc aggatcagac tacccagttc cagttgttcc tccctctcc ttcttcact
 661 ccgattcc tgactgaatt tctggtgaac tatcataaac atgccgtaca tattctggct
 721 aattactctg atcagggtaa tcacttgttg ttcgaagccc agcgtatgat ttatgcagtt
 781 gcattcttcc cggaatttaa agaagctccg gcctggagca aagcggtat cgacattctg
 841 aaccgtgaag taaacgtaca ggttacaac gatggcggcc agtttgaact tgacccgcat
 901 tatcatcttg ctgctatcaa tatcttctgc aaggcattgg gtatcgcgga tgttaacgga
 961 ttccgtaatg agttcccaca ggaatatctg gatactatcg aaaagatgat catgttctat
1021 gccaatatt ctttcccgga ttacacaaat ccgtgttca gtgatgctaa aatcacagaa
1081 aagaaagaaa tgctgaagaa ctatcgtgca tggagcaaac tgttcccgaa aacgaaact
1141 atcaagtatt tggcaacaga cggcaaagaa ggcgcgttac ccgattatat gtcgaaaggt
1201 ttcctgaaat caggtttctt tgtgttccgc aattcctggg gaatggatgc tacacaaatg
1261 gtagtaaaag ccggtccgaa aggtttctgc cactgtcagc gactccggtt cggataacgg tactttcgaa
1321 atgtggttta acggcaagaa cctgttccca caactggcat cgtcagactt cgtatgtgta tgccggtgaa
1381 ggcgaagtga tggaacaacg tggaactgga aacaaccgaa tctgttacta cgtacacaa caccgtgact
1441 ctggacaata agaatctgga aacaaccgaa tctgttacta agctacaaga aactgtggca gccggaaggc
1501 aatatccaga ccttggttac agaaaaccca agctacaaga acttcaagca cgccgttcg
1561 gtcttcttcg tagacaatac ctactttgtc attgtagatg aagtatcagg cagcgccaaa
1621 ggttcttcg tagacaatac ctactttgtc attgtagatg aagtatcagg cagcgccaaa
1681 atgacattcc tgactcaatt cgaagatgga agcaacatga tagccaacag aacttcaatg cttcggccct
1741 gaaggcatga gcatgaaaaa cgaagatgga agcaacatga tagccaacag aacttcaatg cttcggccct
1801 aaacgtatga atgtttcatt accagtcaa gaagagcgca gatgccccta aatttgacgc taagttcaag
1861 acagttattt accagtcaa gaagagcgca gatgccccta aatttgacgc taagttcaag
1921 aacaaaacgt tcgatgaaaa cggactggaa atagaagtga aagtaaacgg caagaaacag
1981 tcattaaat ataaattata a
```

FIG. 5A

```
  1 mnktlkyivl ltfacfvgkq yaqelksevf sllnldypgl ekvkalhqeg kdedaakall
 61 dyyrartnvk tpdinlkkit igkeeqqwad dglkhtffvh kgyqpsynyg edinwqywpv
121 kdnelrwqlh rhkwftpmgk ayrvsgdeky akewayqyid wikknplvkm dkkeyelvsd
181 gislkgevenv rfawrplevs nrlqddttqf qlflpspsft pdflteflvn yhkhavhila
241 nysdqgnhll feaqrmiyag affpefkeap awrksgidil nrevnvqvyn dggqfeldph
301 yhlaainifc kalgiadvng frnefpqeyl dtiekmimfy anisfpdytn pcfsdakite
361 kkemlknyra wsklfpknet ikylatdgke galpdymskg flksgffvfr nswgmdatqm
421 vvkagpkgfw hcqpdngtfe mwfngknlfp dsgsyvyage gevmeqrnwh rqtsvhntvt
481 ldnknlette svtklwqpeg niqtlvtenp syknfkhrrs vffvdntyfv ivdevsgsak
541 gsvnlhyqmp kgeiansred mtfltqfedg snmklqcfgp egmsmkkepg wcstayrkry
601 krmnvsfnvk kdnenavryi tviypvkksa dapkfdakfk nktfdengle ievkvngkkq
661 slkykl
```

FIG. 5B

```
FH Hep. III    1   ■TT■IF■R■■IV■FAVIALSSGNIL■QSSS■■TRKD■■DH■■■E■S■■■■■NKAVAA■■NY■■■■
BT Hlyase II   1   -MN■TL■Y■■V■LTFACFVG---K■YAQE■KSEV■SL■■■D■■P■■■K■KALHQE■KD■■■■
consensus      1   m--K--K-Iiv--------gni-a----i----F---iNLeY-GLEKV------G--dDAA FH Hep. III   61   ■■■A■■EK■SKA■E■■■FSNAEKPADI■QP■D■VTREM■■KA■V■Q■QP■■■■■G-Y■D■■
BT Hlyase II  57   ■■■D■■■A■■NVK■T■■■IN------LKK■IT■G■EEQQW■■D■■K■■T■FV■■K■■■Q■SY■N■■
consensus     61   KALL-YYR-ks--r-PD--naekpa--r--I-K-----AD-aL-H-F--HKGY-p-f-YG FH Hep. III  120   K■■■■■■M■■■■■■■■■V■■■■■V■■WQA■■ALV■HA■■■■■■■R■■V■■■■SE■■AR■■■■■GLS
BT Hlyase II 111   E■■■■■Y■■■■■■■■■■■■HR■■TP■■GKA■■RVS■■■■■■■K■■■A■■■I■■IK■■■■VKM
consensus    121   -DINWQ--WPVKDNEvRWQLHR-KWw--Ma--Y--tGDEKYArEW-YQY-DW-rKNPL---

FH Hep. III  180   Q---------------■D■DK■■V■■■■■D■V■SLPPT■■S■■■VN■■■A■■■■A■■M■■■NS
BT Hlyase II 171   DKKEYELVSDGKIKGEV■■■VR■A■■■■■■■■■■N■■L■DQTTQ■■Q■■■LPS■S■■■D■■T■■■VN
consensus    181   -kkeyelvsdgkikgevdN-kF-WRPLEVS-RvQ-----F-LFv-SP-FTP-FL-EFL--

FH Hep. III  224   ■■QQ■■DY■STH■■A■■■■R■■■■■A■■■■NL■■■VS■■■■■KDS■■R■■Q■■■■SV■■T■■IKK■■■A
BT Hlyase II 231   ■■KH■VH■■LAN■SD■■■■L■■■■A■■M■Y■■AF■■■■■KEA■A■■KS■■DI■■R■MN■■■■N
consensus    241   YH--A--I----Y-eQGNH-LFEAQR-IfAG--FPEFKd-P-WR-tGI-vLN-Ei--QVY- FH Hep. III  284   ■■M■■■■S■I■HV■■■D■■LK■Y■S■KRVNLEK■■■■Q■S■VQ■■V■N■■■YALIS■■L■■■NT
BT Hlyase II 291   ■■G■■■■■D■H■■L■■AN■■■C■■L■■I■DVNGFRN■■■■E■LD■■■K■■■Y■FYAN■■F■■■TN
consensus    301   DG--QFEL-P-YHvAAI-IF-KA-G-A-------EFPQ-Yv-TvE-MIM----IS-PDY--

FH Hep. III  344   ■M■G■SW■■DKNFRM■QE■AS■■ARV■■■A■QA■■KY■■■A■■■■■K■QGKA■■■N■■L■■KA■LSNA■■■Y■T■■
BT Hlyase II 351   ■C■S■AK■■■E■KKEM■KN■■RA■■SK■■P■■K■NET■■KY■L■■TD■■KE■■AL■D■M■K■GFLKS■■■V■■
consensus    361   P-F-D--ITdK---m-qf--W-rvFP-N--IKY-ATDGK-G---P-fISKa----GFy-FR FH Hep. III  404   SG■■DKN■■V■■LK■ASS■P■EE■■A■■■■■■■■■■FL■IK■■R■FT■■■A■VE■■■S■■DEA■■KL■■■Y
BT Hlyase II 411   NS■■GMD■■Q■■V■■■A■G■■K■FW■■C■■■■■■■■MW■FN■■K■LF■■■S■■S■■■A■■EGEV■EQ■■■H
consensus    421   --W----AT-MVIKA-P-G--fH-QPDNGTFEIf--GrN--PD-G-fVY-Gd--iM--RNW- FH Hep. III  464   ■■■R■■S■■L■■■■QN■V■I■KARQNK■■ETGN■■LDV■■TYT■■F■S■PNLD■Q■RS■■L■■NKK■■■L
BT Hlyase II 471   ■■■SV■■N■■V■■■■K■LET■ESVTKL■QPEG■■QT■■VTE■■S■K■FK■R■■■F■■VDNT■■V
consensus    481   RQT-iH-TITLDN-Nm--T------W----NI--L--NPSY-N--H-RSV-Fi---YFI FH Hep. III  524   ■V■■RAI■■E■■T■■NLG■■■WC■■LKE■SNPVFD■TKNRVY■■TM■R■■■N■LM■■■SLNADRT■■L■NE■■E
BT Hlyase II 531   ■I■V■EVS■S■■K■SVNL■■Y■MPK-GEIANS■REDMTFL■QE■E■■■■SNMKL■Q■CFGP■EGM■S■KKK■■P
consensus    541   viD---G-A-G-I-vHwQI---d------k------T-y-DG-NI-iQ----d--SI--E-

FH Hep. III  584   ■KV■YV■■N■■EL■■PAFV■■EKP■KN■ACTQNE■VSIV■■■YDGQKAPEISIREN■KGND■■KCK■
BT Hlyase II 590   ■WC■TA■■R■RY■■MNVS■■NVK■D■■ENAVR■YITVI■■VKKSADAPKFDAKF■NKT■■DENG■
consensus    601   G--S--Y-K--KR----F---K-N-----fvsivYP---------K---Fe---L FH Hep. III  644   N■T■T■T■■■■KQ■LV■LVP-
BT Hlyase II 650   E■■EV■KV■■■■K■SL■KYKL
consensus    661   -I-I-iNGK-Q-v---I
```

FIG. 6

HEPARAN SULFATE GLYCOSAMINOGLYCAN LYASE AND USES THEREOF

BACKGROUND OF THE INVENTION

Heparin and heparan sulfate represent a class of glycosaminoglycans characterized by a linear polysaccharide of D-glucosamine linked to hexuronic acid (Linhardt, R. J. (1991) Chem. Ind. 2, 45-50; Casu, B. (1985) Adv. Carbohydr. Chem. Biochem. 43, 51-134). Heparin and heparan sulfate are complex carbohydrates that play an important functional role in the extracellular matrix of mammals. These polysaccharides modulate and regulate critical biochemical signaling pathways which impinge on normal physiological processes such as cell and tissue morphogenesis, cell-cell interactions, and growth and differentiation. These polysaccharides also play a critical role in various pathologies including wound healing, tumor growth and metastasis, certain neurodegenerative disorders and microbial pathogenesis, to name a few.

Much of the current understanding of heparin and heparan sulfate sequence has relied on studies of their biosynthesis (Linhardt, R. J., Wang, H. M., Loganathan, D., and Bae, J. H. (1992) Biol. Chem. 267, 2380-2387; Lindahl, U., Feingold, D., and Roden, L. (1986) Trends Biochem. Sci. 11, 221-225; Jacobson, I., and Lindahl U. (1980) J. Biol. Chem. 255, 5094-5100; Lindahl, U., and Kjellen, L. (1987) in The Biology of Extracellular Matrix Proteoglycans (Wight, T. N., and Mecham R., eds) pp. 59-104, Academic Press, New York).

Heparan sulfate, which is chemically related to heparin, is present on the cell surface and within the extracellular matrix (ECM) of virtually every mammalian cell type. These heparin-like glycosaminoglycans (HLGAGs) are present in this extracellular environment as protein-polysaccharide conjugates known as proteoglycans. It is increasingly recognized that HLGAGs play much more than a mere structural role as they interact in a functional manner with numerous proteins of the extracellular matrix, such as laminin, fibronectin, integrins, and collagen. As such, HLGAGs (as part of proteoglycans) help to define the biological properties of the matrix. These HLGAGs also interact with an array of cytokine-like growth factors and morphogens present within the extracellular matrix by facilitating their biochemical interaction with receptors and by protecting them from proteolytic degradation. For example, heparin potentiates the biological activity of aFGF, as reported by Thornton, et al., Science 222, 623-625 (1983), possibly by potentiating the affinity of aFGF for its cell surface receptors, as reported by Schreiber, et al., Proc. Natl. Acad. Sci. USA 82, 6138-6142 (1.985). Heparin protects aFGF and bFGF from degradation by heat, acid and proteases, as reported by Gospodarowicz and Cheng, J. Cell Physiol. 128, 475-4 84 (1986); Rosengart, et al., Biochem. Biophys. Res. Commun. 152, 432-440 (1988); and Lobb Biochem. 27, 2572-2578 (1988). bFGF is stored in the extracellular matrix and can be mobilized in a biologically active form by the hydrolyzing activity of enzymes such as heparanase as reported by Vlodavsky, et al., Proc. Natl. Acad. Sci. USA 84, 2292-2296 (1987) and Folkman, et al., Am. J. Pathol. 130, 393-400 (1988) and Emerson et. al. Proc. Natl. Acad. Sci. USA 101(14): 4833-8 (2004).

The binding of FGF to heparan sulfate is a prerequisite for the binding of FGF to its high affinity receptor on the cell surface, as reported by Yayon, et al., Cell 64, 841-848 (1991) and Papraeger, et al., Science 252, 1705-1708 (1991). A specific heparan sulfate proteoglycan has been found to mediate the binding of bFGF to the cell surface, as described by Kiefer, et al., Proc. Natl. Acad. Sci. USA 87, 6985-6989 (1990).

Heparin lyases, such as heparinases, are a general class of enzymes that are capable of specifically cleaving the major glycosidic linkages in heparin and heparan sulfate. Three heparinases have been identified in *Flavobacterium heparinum*, a GAG-utilizing organism that also produces exoglycoronidases, glycosidases, sulfoesterases, and sulfamidases and other enzymes which further act on the lyase-generated oligosaccharide products (Yang, et al. J. Biol. Chem. 260, 1849-1857 (1987); Galliher, et al. Eur. J. Appl. Microbiol. Biotechnol. 15, 252-257 (1982). These lyases are designated as heparinase I (heparinase, EC 4.2.2.7), heparinase II (heparinase II, no EC number) and heparinase III (heparinase EC 4.2.2.8). The three purified heparinases differ in their capacity to cleave heparin and heparan sulfate: Heparinase I primarily cleaves heparin, heparinase III specifically cleaves heparan sulfate; and heparinase II acts on both heparin and heparan sulfate. Several Bacteroides species (Saylers, et al. Appl. Environ. Microbiol. 33, 319-322 (1977); Nakamura, et al. J. Clin. Microbiol. 26, 1070-1071 (1988)) also produce heparin lyases. A heparin lyase has also been purified to apparent homogeneity from an unidentified soil bacterium by Bohmer, et al. J. Biol. Chem. 265, 13609-13617 (1990).

SUMMARY OF THE INVENTION

The invention is based, in part, on the discovery and recombinant expression of heparin sulfate glucosaminoglycan (HS-GAG) lyases from *Bacteroides thetaiotaomicron*, hereafter referred to as "*B. thetaiotaomicron* HSGAG lyases", e.g., *B. thetaiotaomicron* HSGAG lyase I and *B. thetaiotaomicron* HSGAG lyase II, useful, inter alia, in the structure-specific cleavage of heparin and/or heparan sulfate. Thus, the invention includes methods, compositions and kits with a *B. thetaiotaomicron* HSGAG lyase or functional fragments thereof and combinations of *B. thetaiotaomicron* HSGAG lyases or functional fragments thereof, for, e.g., characterization or modification of glycoaminoglycans (GAGs) such as heparin-like glycoaminoglycans (HLGAGs), e.g., heparin and heparan sulfate. For example, the methods, compositions and kits can be used to analyze and monitor heterogeneous populations of GAGs, e.g., HLGAGs. In other aspects, the methods, compositions and kits can be used to modify the structure and/or activity of GAGs, e.g., HLGAGs.

According, in one aspect, the invention features *B. thetaiotaomicron* HSGAG lyase polypeptides, or functional fragments thereof, e.g., *B. thetaiotaomicron* HSGAG lyase polypeptides, or functional fragments thereof, having the amino acid sequence shown in SEQ ID NOs:2, 4, 6, 8, 10 or 23; an amino acid substantially identical to the amino acid sequence shown in SEQ ID NOs:2, 4, 6, 8, 10 or 23; or an amino acid encoded by a nucleic acid molecule that hybridizes under stringent hybridization conditions to a nucleic acid molecule comprising the nucleic acid sequence of SEQ ID NOs:1, 3, 5, 7, 9, 22, wherein the nucleic acid encodes a full length *B. thetaiotaomicron* HSGAG lyase protein, or functional fragments thereof.

In another aspect, the invention features a composition that includes a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptides, *B. thetaiotaomicron* HSGAG lyase polypeptides, or functional fragments thereof, described herein. In one embodiment, the composition further comprises one or more HLGAG degrading enzyme, e.g., one or more heparinase and/or one or more HSGAG lyase polypeptide other than a *B. thetaiotaomicron* HSGAG lyase polypeptides. For example, the composition can further include one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV, mammalian heparanase); and functional fragments and variants thereof. Such compositions can be used, e.g., to cleave a HLGAG such as heparin and/or heparan sulfate, e.g., to characterize a preparation of HLGAGs such as heparin and/or heparan sulfate.

In another aspect, the invention features a method of specifically cleaving an HLGAG, e.g., heparin or heparan sulfate, that includes contacting an HLGAG with a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein. In one embodiment, the HLGAG is cleaved into di-, tri-, tetra-, penta-, hexa-, octa-, and/or deca-saccharides and, e.g., the method further includes determining the sequence of the di-, tri-, tetra-, penta-, hexa-, octa-, deca- and/or longer saccharides of the HLGAG. In one embodiment, the method further includes contacting the HLGAG with one or more HLGAG degrading enzyme, e.g., a heparinase polypeptide or a HSGAG lyase polypeptide other than a *B. thetaiotaomicron* HSGAG lyase polypeptide. For example, the HLGAG degrtading enzyme can be one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV, mammalian heparanase); and functional fragments and variants thereof.

In another aspect, the invention features methods for analyzing heterogeneous populations of HLGAGs, e.g., heparin (e.g., UFH, LMWH, and synthetic heparins), and heparan sulfate, that include contacting the population with a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein. Thus, in some aspects, the invention relates to methods and products associated with analyzing and monitoring heterogeneous populations of HLGAGs, e.g., to thus defining the structural signature and activity of heterogeneous populations of HLGAGs, using a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, or functional fragment thereof, described herein.

In some embodiments, the method includes determining the structural signature of one or more batches of an HLGAG product that has been contacted with a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein. In some embodiments, the method further includes selecting a batch as a result of the determination. In some embodiments, the method further includes comparing the results of the determination to preselected values, e.g., a reference standard. The preselected value can be, e.g., the presence or absence or a set value (e.g., mole % or area under the curve) of one or more di-, tri-, tetra-, penta-, hexa-, octa-, and/or deca-saccharide associated with cleavage of the HLGAG with a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragment thereof, described herein.

For any of the methods described herein, a completely or partially *B. thetaiotaomicron* HSGAG lyase polypeptide (or polypeptides) digested sample can be analyzed to determine the structural signature by, e.g., one or more of mass spectroscopy, NMR spectroscopy, gel electrophoresis, capillary electrophoresis, reverse-phase column chromatography (e.g., HPLC, e.g., HPLC with a stationary phase dynamically coated with a quanterrnary ammonium salt), ion-pair HPLC. The methods described herein can further include digesting the sample with one or more HLGAG degrading enzyme, e.g., a heparinase or a heparin lyase polypeptide other than a *B. thetaiotaomicron* HSGAG lyase polypeptide. For example, the HLGAG degrading enzyme can be one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV, mammalian heparanase); and functional fragments and variants thereof.

In another aspect, the invention features an HLGAG preparation (e.g., a heparin or heparan sulfate preparation) produced by contacting an HLGAG preparation with a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein. In one embodiment, the HLGAG preparation (e.g., the heparin or heparan sulfate preparation) has one or more of reduced anti-Xa activity and anti-IIa activity, e.g., as compared to a reference standard, e.g., as compared to a commercially available heparin or heparan sulfate or as compared to the heparin or heparan sulfate preparation prior to contacting with a *B.*

*thetaiotaomicron* HSGAG lyase polypeptide. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity is reduced. Such preparation can be useful, e.g., for applications where reduced anti-Xa activity and/or anti-IIa activity is desirable, e.g., such as the use of heparin or heparan sulfate as a carrier for another agent, e.g., a therapeutic agent, prophylactic or diagnostic agent. Thus, in some embodiments, the HLGAG preparation can further include a second agent other than the HLGAG, e.g., the preparation can further include one or more therapeutic, prophylactic or diagnostic agents. In another embodiment, the HLGAG preparation (e.g., the heparin or heparan sulfate preparation) has one or more of increased anti-Xa activity and anti-IIa activity, e.g., as compared to a reference standard, e.g., as compared to a commercially available heparin or heparan sulfate or as compared to the heparin or heparan sulfate preparation prior to contacting with a *B. thetaiotaomicron* HSGAG lyase polypeptide. Such preparation can be useful, e.g., for applications were increased anti-Xa activity and/or anti-IIa activity is desirable, e.g., as an anti-coagulant and/or anti-thrombotic agent.

In another aspect, the invention features a method of neutralizing one or more activities of an HLGAG (e.g., a heparin or heparan sulfate). The method includes contacting the HLGAG with a *B. thetaiotaomicron* HSGAG lyase polypeptide, or functional fragment thereof, e.g., a *B. thetaiotaomicron* HSGAG lyase I polypeptide, or functional fragment thereof, described herein. When the HLGAG is heparin or heparan sulfate, the activity to be neutralized can be one or more of anti-Xa activity and anti-IIa activity. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity is reduced. The HLGAG can be, e.g., contacted ex vivo or in vivo. Thus, in some embodiments, the method can include administering the *B. thetaiotaomicron* HSGAG lyase polypeptide, or functional fragment thereof, to a subject in an amount effective to neutralize anti-Xa activity and/or anti-IIa activity in the subject, e.g., a subject that has been administered an HLGAG such as heparin or heparan sulfate, e.g., a subject that has been administered heparin or heparan sulfate to inhibit coagulation and/or thrombosis.

In another aspect, the invention features a method of inhibiting angiogenesis in a subject. The method includes administering to the subject an effect amount of a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein, to thereby inhibit angiogenesis. In one embodiment, the subject has a disease or disorder associated with unwanted angiogenesis. Such disorders include, but are not limited to, arthritis (e.g., rheumatoid arthritis), various eye disorders (e.g., diabetic retinopathy, neovascular glaucoma, inflammatory disorders, ocular tumors (e.g., retinoblastoma), retrolental fibroplasias, uveitis as well as disorders associated with choroidal neovascularization and iris neovascularization) and cancer (e.g., tumor growth and metastases).

In another aspect, the invention features a method of inhibiting unwanted cellular proliferation and/or differentation in a subject. The method includes administering to the subject an effect amount of a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein, to thereby inhibit cellular proliferation and/or differentiation. In one embodiment, the subject has cancer.

In another aspect, the invention features a pharmaceutical composition that includes a *B. thetaiotaomicron* HSGAG lyase polypeptide, *B. thetaiotaomicron* HSGAG lyase polypeptides, or functional fragments thereof, e.g., a *B. thetaiotaomicron* HSGAG lyase polypeptide, *B. thetaiotaomicron* HSGAG lyase polypeptides, or functional fragments thereof, described herein, and a pharmaceutically acceptable carrier. In one embodiment, the *B. thetaiotaomicron* HSGAG lyase polypeptide, *B. thetaiotaomicron* HSGAG lyase polypeptides, or functional fragments thereof, is present in an amount effective to neutralize one or more activity of an HLGAG. Preferably, the HLGAG is heparin or heparan sulfate and the *B. thetaiotaomicron* HSGAG lyase polypeptide, or functional fragment thereof, is present in an amount effective to neutralize one or more of anti-Xa activity and anti-IIa activity. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity is reduced. In another embodiment, the *B. thetaiotaomicron* HSGAG lyase polypeptide, or functional fragment thereof, is present in an amount effective to inhibit angiogenesis.

In another aspect, the invention features a kit comprising a composition of *B. thetaiotaomicron* HSGAG lyase polypeptide, *B. thetaiotaomicron* HSGAG lyase polypeptides, or functional fragments thereof. In one embodiment, the kit further includes one or more HLGAG degrading enzyme, e.g., one or more heparinase polypeptide and/or one or more HSGAG lyase polypeptide other than *B. thetaiotaomicron* HSGAG lyase polypeptide. For example, the kit can further comprise one or more of: an unsaturated glucuronyl hydrolase (e.g., *F. heparinum* Δ4,5 glycuronidase; *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase: *B. thetaiotaomicron* 6-O-sulfatase; mucin desulfating enzymes; mammalian N-acetylglucosamine-6-sulfatase; mammalian iduronic acid-2-sulfatase); a N-sulfamidase (e.g., *F. heparinum* N-sulfamidase; mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV, mammalian heparanase); and functional fragments and variants thereof. In one embodiment, the *B. thetaiotaomicron* HSGAG lyase polypeptide, or functional fragment thereof, and one or more of the other HLGAG degrading enzymes are in the same composition. In another embodiment, the *B. thetaiotaomicron* HSGAG lyase polypeptide, or functional fragment thereof, and the other HLGAG degrading enzyme are in different compositions. In another embodiment, the *B. thetaiotaomicron* HSGAG lyase polypeptide, or functional fragment thereof, is in a pharmaceutical composition with a pharmaceutically effective carrier. The kits can further include an HLGAG, e.g., heparin and/or heparan sulfate. In one embodiment, when the kit includes a pharmaceutical composition of a *B. thetaiotaomicron* HSGAG lyase polypeptide, or functional fragment thereof, the HLGAG, e.g., heparin and/or heparan sulfate, is also in a pharmaceutical composition and, e.g., the kit further includes instructional material for neutralizing one or more activity of the HLGAG.

In another aspect, the invention features a nucleic acid molecule which encodes a *B. thetaiotaomicron* HSGAG lyase polypeptides, or functional fragments thereof. In one embodiment, the isolated nucleic acid molecule encodes a polypeptide having the amino acid sequence of SEQ ID NOs:2, 4, 6, 8, 10 or 23. In other embodiments, the invention provides isolated *B. thetaiotaomicron* HSGAG lyase nucleic acid molecules having the nucleotide sequence shown in SEQ ID NOs:1, 3, 5, 7, 9 or 22. In another embodiment, the invention provides nucleic acid molecules that are substantially identical to (e.g., naturally occurring allelic variants) to the nucleotide sequence shown in SEQ ID NOs:1 or 5 and nucleic acid molecules that hybridize under stringent hybridization conditions to a nucleic acid molecule comprising the nucleotide sequence of SEQ ID NOs:1, 3, 5, 7, 9 or 22 wherein the nucleic acid encodes a full length *B. thetaiotaomicron* HSGAG lyase protein, or functional fragments thereof.

In a related aspect, the invention further provides nucleic acid constructs which include a *B. thetaiotaomicron* HSGAG lyase nucleic acid molecule described herein. In certain embodiments, the nucleic acid molecules of the invention are operatively linked to native or heterogonous regulatory sequences. Also included are vectors and host cells containing the *B. thetaiotaomicron* HSGAG lyase nucleic acid molecules of the invention, e.g., vectors and host cells suitable for producing *B. thetaiotaomicron* HSGAG lyase nucleic acid molecules and polypeptides.

In another aspect, the invention features antibodies and antigen-binding fragments thereof, that react with, or more preferably, specifically bind *B. thetaiotaomicron* HSGAG lyase polypeptides.

In another aspect, the invention provides methods of screening for compounds that modulate the expression or activity of the *B. thetaiotaomicron* HSGAG lyase polypeptides or nucleic acids.

Other features and advantages of the invention will be apparent from the following detailed description, and from the claims.

BRIEF DESCRIPTION OF THE DRAWINGS

FIG. 1A depicts a DNA sequence (SEQ ID NO:1) encoding *B. thetaiotaomicron* HSGAG lyase I. Initiating methinione codon (ATG) is underlined and a second, internal methinione codon is doubled unlined. FIG. 1B depicts its predicted amino acid sequence (SEQ ID NO:2) as well as indicating in bold the N-terminal amino acid residues of two variants of *B. thetaiotaomicron* HSGAG lyase I refered to as the M17 variant (SEQ ID NO:4) and the Q26 variant (SEQ ID NO:23).

FIG. 2 depicts a BLAST alignment of *B. thetaiotaomicron* HSGAG lyase I (SEQ ID NO:2) with a heparinase I from *Flavobacterium heparinum* (SEQ ID NO:24) and consensus sequence (SEQ ID NO:26).

FIG. 3A depicts a DNA sequence (SEQ ID NO:3) encoding the M17 variant of *B. thetaiotaomicron* HSGAG lyase I. FIG. 3B depicts its predicted amino acid sequence (SEQ ID NO:4).

FIG. 4A depicts a DNA sequence (SEQ ID NO:22) encoding the Q26 variant of *B. thetaiotaomicron* HSGAG lyase I. FIG. 4B depicts its predicted amino acid sequence (SEQ ID NO:23).

FIG. 5A depicts a DNA sequence (SEQ ID NO:5) encoding *B. thetaiotaomicron* HSGAG lyase II. FIG. 5A also depicts portions of the nucleotide sequence encoding *B. thetaiotaomicron* HSGAG lyase II that are not present in to variants of *B. thetaiotaomicron* HSGAG lyase II, namely the "Q23 variant" (SEQ ID NO:7) the deleted portion indicated by underlining, and the "K169 variant" (SEQ ID NO:9) the deleted portion indicated by shading. FIG. 5B depicts the predicted amino acid sequence *B. thetaiotaomicron* HSGAG lyase II (SEQ ID NO:6) as well as indicating the portions deleted from the amino acid sequence of the Q23 variant (SEQ ID NO:8) and the K169 variant (SEQ ID NO:10).

FIG. 6 depicts a BLAST alignment of *B. thetaiotaomicron* HSGAG lyase II (SEQ ID NO:6) with a heparinase III from *Flavobacterium heparinum* (SEQ ID NO:25)and concensus sequence (SEQ ID NO:27).

DETAILED DESCRIPTION

Overview

Figure 7:
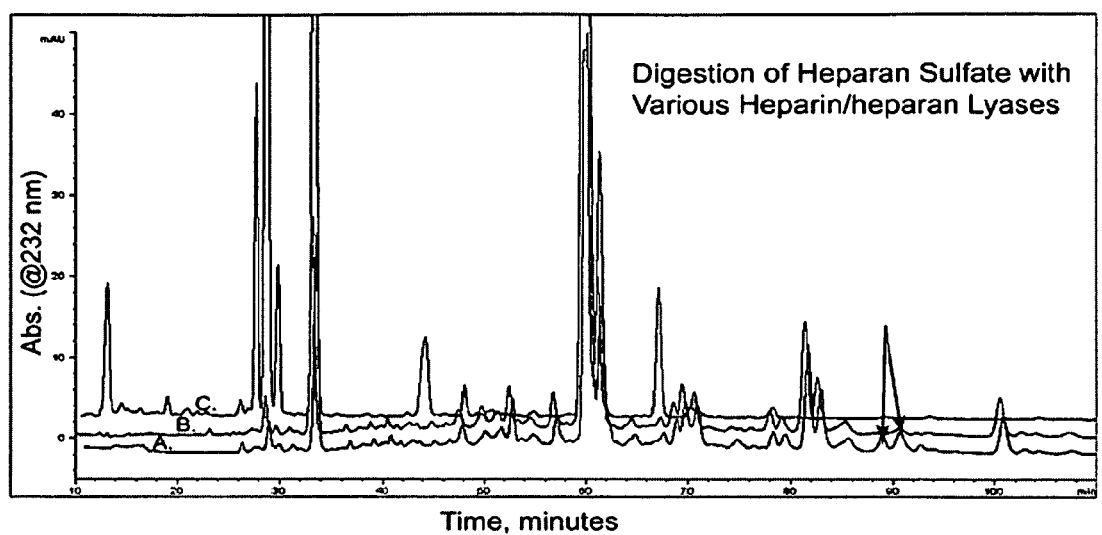
FIG. 7 is a representation of an SAX—HPLC chromatogram. Trace A depicts the digestion products of porcine mucosa treated with recombinant *B. thetaiotaomicron* HSGAG lyase I. Trace B depicts the digestion products of porcine mucosa treated with recombinant *Flavobacterium heparinum* heparinase I. Trace C depicts the digestion products of porcine mucosa treated with recombinant *Flavobacterium heparinum* heparinase II.

This disclosure describes recombinant expression of active *B. thetaiotaomicron* HSGAG lyases from *B. thetaiotaomicron*, that are useful, inter alia, in the modification and characterization of GAGs such as heparin and/or heparan sulfate glycosaminoglycans and derivatives thereof.

For example, the *B. thetaiotaomicron* HSGAG lyases described herein can be a complementary tool to existing chemo-enzymatic methods for cleaving GAGs such as heparin and heparan sulfate polysaccharides in a structure-specific fashion. Structure specific cleavage of a GAG, e.g., heparin and/or heparan sulfate, can be used, e.g., to determine the structure of GAGs in a heterogenous GAG preparation. In addition, cleavage can be used, e.g., to produce lower molecular weight oligosaccharides from the GAG. Thus, the *B. thetaiotaomicron* HSGAG lyases can be used to generate, e.g., heparin- and heparan sulfate-derived oligosaccharides. Such heparin- and heparan sulfate-derived oligosaccharides may have diagnostic, prophylactic and therapeutic potential.

In addition, the *B. thetaiotaomicron* HSGAG lyases described herein may also have prophylactic and therapeutic potential, e.g., in disorders associated with angiogenesis.

The *B. thetaiotaomicron* HSGAG lyases further can be used in the ex vivo and/or in vivo to neutralize an anti-coagulant and/or anti-thrombotic activity of heparin and/or heparan sulfate.

The *B. thetaiotaomicron* heparin lyase sequence (FIG. 1; SEQ ID NO:1), which is approximately 1130 nucleotides long including untranslated regions, contains a predicted methionine-initiated coding sequence of about 1128 nucleotides, including the termination codon (nucleotides indicated as coding of SEQ ID NO:1 in FIG. 1). The coding sequence encodes a 392 amino acid protein (SEQ ID NO:2).

A variant in which the amino terminus begins at the methinione at residue 17 (M17) can also be used to produce recombinant protein. The amino acid sequence and nucleotide sequence encoding the M17 variant of *B. thetaiotaomi-*

*cron* HSGAG lyase I are depicted in FIGS. 3B (SEQ ID NO:4) and 3A (SEQ ID NO:3), respectively.

Another variant in which the amino terminus begins at the glutamine at residue Q26 can also be used to produce recombinant protein. The amino acid sequence and nucleotide sequence encoding the Q26 variant of *B. thetaiotaomicron* HSGAG lyase I are depicted in FIGS. 4B (SEQ ID NO:23) and 4A (SEQ ID NO:22), respectively.

The *B. thetaiotaomicron* HSGAG lyase I protein contains a significant number of structural characteristics in common with heparinase I obtained from *Flavobacterium heparinum.*

The *B. thetaiotaomicron* HSGAG lyase II sequence (FIG. 5; SEQ ID NO:5), which is approximately 2001 nucleotides long including untranslated regions including the termination codon (nucleotides indicated as coding of SEQ ID NO:5 in FIG. 5). The coding sequence encodes a 666 amino acid protein (SEQ ID NO:6).

A variant in which the amino terminus begins at the glutamine at residue 23 (Q23) can also be used to produce recombinant protein. The amino acid sequence and nucleotide sequence encoding the Q23 variant of *B. thetaiotaomicron* HSGAG lyase II are depicted in FIGS. 5B (SEQ ID NO:8) and 5A (SEQ ID NO:7), respectively.

Another variant in which is a deletion beginning at the lysine at residue 169 (K169) and ending at the glutamic acid at residue 186 can also be used to produce recombinant protein. The amino acid sequence and nucleotide sequence encoding the K169 variant of *B. thetaiotaomicron* HSGAG lyase II are depicted in FIG. 5B (SEQ ID NO:10) and 5A (SEQ ID NO:9), respectively.

The *B. thetaiotaomicron* HSGAG lyase II protein contains a significant number of structural characteristics in common with heparinase III obtained from *Flavobacterium heparinum.*

As the *B. thetaiotaomicron* HSGAG lyase polypeptides of the invention may modulate heparin- and/or heparan sulfate-mediated activities, they may be useful in various prophylactic and therapeutic applications as well as for developing novel prophylactic and diagnostic agents for heparin- or heparan sulfate-mediated or related disorders.

As used herein, a "HSGAG lyase activity", "biological activity of HSGAG lyase" or "functional activity of HSGAG lyase", refers to an activity exerted by a *B. thetaiotaomicron* HSGAG lyase protein, polypeptide or nucleic acid molecule in a physiological milieu. For example, a HSGAG lyase activity can be an activity exerted by *B. thetaiotaomicron* HSGAG lyase on e.g., on a HSGAG lyase substrate, e.g., glycosidic linkages in heparin or heparan sulfate. A HSGAG lyase activity can be determined in vivo or in vitro.

The *B. thetaiotaomicron* HSGAG lyase molecules of the present invention are predicted to have similar biological activities to various heparinases obtained from *Flavobacterium heparinum*. For example, the *B. thetaiotaomicron* HSGAG lyase proteins of the present invention can have one or more of the following activities: (1) binds a heparin and/or a heparan sulfate; (2) cleaves one or more glycosidic linkages of a heparin and/or a heparan sulfate; (3) modulates, e.g., increases or reduces, anti-Xa activity and/or anti-IIa activity of a heparin and/or a heparan sulfate; and (4) reduces or eliminates angiogenesis.

In some aspects, the *B. thetaiotaomicron* HSGAG lyase I has biological activity similar to, but not identical with, heparinase I obtained from *Flavobacterium heparinum*. For example, the *B. thetaiotaomicron* HSGAG lyase I can have one or more of the following activities: (1) binds a heparin and/or heparan sulfate; (2) cleaves one or more glycosidic linkages of heparin and/or heparan sulfate, e.g., cleaves one or more glycosidic linkages of sulfated uronic acids, e.g., 2-O and/or 3-O sulfated uronic acids; (3) reduces anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity is reduced.

Thus, the *B. thetaiotaomicron* HSGAG lyase molecules, e.g., the *B. thetaiotaomicron* HSGAG lyase I molecules can act as novel therapeutic agents for controlling heparin-associated disorders. Examples of such disorders include heparin-induced anticoagulation and/or angiogenesis. For example, the *B. thetaiotaomicron* HSGAG lyase molecules, e.g., the *B. thetaiotaomicron* HSGAG lyase I molecules, can be used to reduce or eliminate (e.g., neutralize) one or more anticoagulation properties of a heparin and/or a heparan sulfate, e.g., during or after surgery. In other embodiments, the *B. thetaiotaomicron* HSGAG lyase molecules, e.g., *B. thetaiotaomicron* HSGAG lyase I molecules, can be used to deheparinize blood, e.g., in a bioreactor, e.g., a bioreactor used in heart-lung and/or kidney dialysis.

In some aspects, the *B. thetaiotaomicron* HSGAG lyase II has biological activity similar to, but not identical with, heparinase II obtained from *Flavobacterium heparinum*. For example, the *B. thetaiotaomicron* HSGAG lyase II can have one or more of the following activities: (1) binds a heparin and/or heparan sulfate; (2) cleaves one or more glycosidic linkages of heparin and/or heparan sulfate, e.g., cleaves one or more glycosidic linkages of sulfated and undersulfated uronic acids; (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is increased while anti-IIa activity is maintained or reduced. In other embodiments, anti-IIa activity is increased while anti-Xa activity is maintained or reduced. In other embodiments, anti-Xa activity and anti-IIa activity are reduced.

Thus, such *B. thetaiotaomicron* HSGAG lyase molecules, e.g., *B. thetaiotaomicron* HSGAG lyase II molecules, can be used to prepare a heparin and/or heparan sulfate preparation useful for treatment of coagulation and/or thrombosis. Examples of such disorders include dissolving or inhibiting formation of thromboses, treatment and prevention of conditions resulting from infarction of cardiac and central nervous system vessels, atherosclerosis, thrombosis, myocardial infarction, arrythmias, atrial fibrillation, angina, unstable angina, refractory angina, congestive heart failure, disseminated intravascular coagulation, percutaneous coronary intervention (PCI), coronary artery bypass graft surgery (CABG), reocclusion or restenosis of reperfused coronary arteries, rheumatic fever, stroke, transient ischemic attacks, thrombotic stroke, embolic stroke, deep venous thrombosi, pulmonary embolism, migraine, allergy, asthma, emphysema, adult respiratory stress syndrome (ARDS), cystic fibrosis, neovascularization of the ocular space, osteoporosis, psoriasis, arthritis (rheumatoid or osteogenic), Alzheimer's disease, bone fractures, major surgery/trauma, burns, surgical procedures, transplantation such as bone marrow transplantation, hip replacement, knee replacement, sepsis, septic shock, pregnancy, hereditary disorders such as hemophilias.

In other embodiments, the *B. thetaiotaomicron* HSGAG lyase molecules, e.g., *B. thetaiotaomicron* HSGAG lyase II molecules, can be used to treat or prevent cellular proliferative or differentiative disorders, e.g., by preventing or inhibiting angiogenesis of cells exhibiting or otherwise associated with unwanted proliferation and/or differentiation. Examples of cellular proliferative and/or differentiative disorders include diabetes; arthritis, e.g., rheumatoid arthritis; ocular disorders, e.g., ocular neovascularization, diabetic retinopathy, neovascular glaucoma, retrolental fibroplasia, uevitis, eye disease associated with choroidal neovascularization, eye disorders associated with iris neovascularization; cancer, e.g., carcinoma, sarcoma, metastatic disorders or hematopoietic neoplastic disorders, e.g., leukemias.

The *B. thetaiotaomicron* HSGAG lyase proteins, fragments thereof, and derivatives and other variants of the sequence in SEQ ID NO:2 or SEQ ID NO:6 thereof are collectively referred to as "polypeptides or proteins of the invention" or "*B. thetaiotaomicron* HSGAG lyase polypeptides or proteins". Nucleic acid molecules encoding such polypeptides or proteins are collectively referred to as "nucleic acids of the invention" or "*B. thetaiotaomicron* HSGAG lyase nucleic acids." "*B. thetaiotaomicron* HSGAG lyase molecules" refer to *B. thetaiotaomicron* HSGAG lyase nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. A DNA molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent hybridization conditions are hybridization in 6× sodium chloride/sodium citrate (SSC) at about 45° C., followed by two washes in 0.2×SSC, 0.1% SDS at 65° C. Hybridization conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. Additional examples of hybridization conditions are as follows: 1) low stringency, hybridization in 6×SSC at about 45° C., followed by one or more washes in 0.2×SSC, 0.1% SDS at 55° C.; 2) medium stringency, hybridization in 6×SSC at about 45° C., followed by one or more washes in 0.2×SSC, 0.1% SDS at 60° C.; and preferably, 3) high stringency, hybridization in 6×SSC at about 45° C., followed by one or more washes in 0.2×SSC, 0. 1% SDS at 65° C. Particularly preferred stringency conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1 corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a *B. thetaiotaomicron* HSGAG lyase protein. The gene can optionally further include non-coding sequences, e.g., regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of *B. thetaiotaomicron* HSGAG lyase protein is at least 10% pure. In a preferred embodiment, the preparation of *B. thetaiotaomicron* HSGAG lyase protein has less than about 30%, 20%, 10% and more preferably 5% (by dry weight), of non-*B. thetaiotaomicron* HSGAG lyase protein (also referred to herein as a "contaminating protein"), or of chemical precursors or non-*B. thetaiotaomicron* HSGAG lyase chemicals. When the *B. thetaiotaomicron* HSGAG lyase protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of *B. thetaiotaomicron* HSGAG lyase without abolishing or substantially altering a HSGAG lyase activity. Preferably, the alteration does not substantially alter the HSGAG lyase activity, e.g., the activity is at least 20%, 40%, 60%, 70% or 80% of wild-type. An "essential" amino acid residue is a residue that, when altered from the wild-type sequence of *B. thetaiotaomicron* HSGAG lyase, results in abolishing a HSGAG lyase activity such that less than 20% of the wild-type activity is present. For example, conserved amino acid residues in *B. thetaiotaomicron* HSGAG lyase are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a *B. thetaiotaomicron* HSGAG lyase protein is preferably replaced with another amino acid residue from the same side chain family. Alternatively, in another embodiment, mutations can be introduced randomly along all or part of a *B. thetaiotaomicron* HSGAG lyase coding sequence, such as by saturation mutagenesis, and the resultant mutants can be screened for HSGAG lyase biological activity to identify mutants that retain activity. Following mutagenesis of SEQ ID NO:1 or SEQ ID NO:5, the encoded protein can be expressed recombinantly and the activity of the protein can be determined.

As used herein, a "biologically active portion" of a *B. thetaiotaomicron* HSGAG lyase protein includes a fragment of a *B. thetaiotaomicron* HSGAG lyase protein which participates in an interaction, e.g., an inter-molecular interaction. An inter-molecular interaction can be a binding interaction or an enzymatic interaction (e.g., the interaction can be transient and a covalent bond is formed or broken). An inter-molecular interaction can be between a HSGAG lyase *B. thetaiotaomicron* molecule and a non-*B. thetaiotaomicron* HSGAG lyase molecule, e.g., heparin, heparan sulfate, and fragments thereof. Biologically active portions of a *B. thetaiotaomicron* HSGAG lyase protein include peptides comprising amino acid sequences sufficiently homologous to or derived from the amino acid sequence of the *B. thetaiotaomicron* HSGAG lyase protein, e.g., the amino acid sequence shown in SEQ ID NO:2 and SEQ ID NO:6, which include less amino acids than the full length *B. thetaiotaomicron* HSGAG lyase proteins, and exhibit at least one activity of a HSGAG lyase protein. Typically, biologically active portions comprise a domain or motif with at least one activity of the HSGAG lyase protein, e.g., depolymerization of heparin, heparan sulfate, and fragments thereof (e.g., in a site specific manor); cleavage of a glycosidic linkage of heparin, heparan sulfate, and fragments thereof; reduce or eliminate an anticoagulant activity, e.g., an anticoagulant activity of heparin, heparan sulfate, and fragments thereof. A biologically active portion of a *B. thetaiotaomicron* HSGAG lyase protein can be a polypeptide which is, for example, 10, 25, 50, 100, 200, 300, 400, 500 or more amino acids in length.

Calculations of homology or sequence identity between sequences (the terms are used interchangeably herein) are performed as follows.

To determine the percent identity of two amino acid sequences, or of two nucleic acid sequences,.the sequences are aligned for optimal comparison purposes (e.g., gaps can be introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap needed to be introduced for optimal alignment of the two sequences. For the purposes of determining if a molecule is within a sequence identity or a homology limitation herein, percent identity is determined by the mathematical algorithm of Needleman and Wunsch ((1970) *J. Mol. Biol.* 48:444-453) as implemented in the GAP program of the GCG software package (available at http://www.gcg.com) with the following parameters: a Blossum 62 scoring matrix with a gap penalty of 12, a gap extend penalty of 4, and a frameshift gap penalty of 5.

In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

For the purposes of analyzing a biological sequence with reference to *B. thetaiotaomicron* HSGAG lyase molecules, the following alignment procedures can be used in addition to the aforementioned Needleman and Wunsch algorithm. The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score =100, wordlength=12 to obtain nucleotide sequences homologous to *B. thetaiotaomicron* HSGAG lyase nucleic acid molecules of the invention. BLAST protein searches can be performed with the XBLAST program, score=50, wordlength=3 to obtain amino acid sequences homologous to *B. thetaiotaomicron* HSGAG lyase protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Particular *B. thetaiotaomicron* HSGAG lyase polypeptides of the present invention have an amino acid sequence sufficiently identical to the amino acid sequence of SEQ ID Nos:2, 4, 6, 8, 10 or 23. In the context of an amino acid sequence, the term "sufficiently identical" or "substantially identical" is used herein to refer to a first amino acid that contains a sufficient or, minimum number of amino acid residues that are i) identical to or ii) conservative substitutions of to aligned amino acid residues in a second amino acid sequence such that the first and second amino acid sequences have a common structural fold and/or a common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity are termed sufficiently or substantially identical. In the context of nucleotide sequence, the term "sufficiently identical" or "substantially identical" is used herein to refer to a first nucleic acid sequence that contains a sufficient or minimum number of nucleotides that are identical to aligned nucleotides in a second nucleic acid sequence such that the first and second nucleotide sequences have a common functional activity or encode a common structural polypeptide fold or a common functional polypeptide activity.

The methods taught herein are sometimes described with reference to heparin-like glycoaminoglycans (HLGAGs) but the properties taught herein can be extended to other polysaccharides. As used herein the terms "HLGAG" and "glycosaminoglycans" (GAGs) are used interchangeably to refer to a family of molecules having heparin like structures and properties, generally referred to herein as "heparin". These molecules include but are not limited to low molecular weight heparin (LMWH), unfractioned heparin, biotechnologically prepared heparin, chemically modified heparin, synthetic heparin such as pentasaccharides (e.g., ARIXTRA™), heparin mimetics and heparan sulfate. The term "biotechnological heparin" encompasses heparin that is prepared from natural sources of polysaccharides which have been chemically modified and is described in Razi et al., Bioche. J. Jul. 15, 1995;309 (Pt 2): 465-72. Chemically modified heparin is described in Yates et al., Carbohydrate Res Nov. 20, 1996; 294:15-27, and is known to those of skill in the art. Synthetic heparin is well known to those of skill in the art and is described in Petitou, M. et al., Bioorg Med Chem Lett. Apr. 19, 1999; 9(8):1161-6 and Vlodavsky et al., Int. J. Cancer, 1999, 83:424-431. An example of a synthetic heparin is fondaparinux. Fondaparinux (ARIXTRA™) is a 5 unit synthetic glycoaminoglycan corresponding to the AT-III binding site. Heparan Sulfate refers to a glycoaminoglycan containing a disaccharide repeat unit similar to heparin, but which has more N-acetyl groups and fewer N— and O-sulfate groups. Heparin mimetics are monosaccharides (e.g., sucralfate), oligosaccharides, or polysaccharides having at least one biological activity of heparin (i.e., anticoagulation, inhibition of cancer, treatment of lung disorders, etc.). Preferably these molecules are highly sulfated. Heparin mimetics may be naturally occurring, synthetic or chemically modified. (Barchi, J. J., Curr. Pharm. Des., Mar. 6, 2000 (4):485-501). The term "HLGAG" also encompasses functional variants of the above-described HLGAG molecules. These functional variants have a similar structure but include slight modifications to the structure which allow the molecule to retain most of its biological activity or have increased biological activity.

"LMWH" as used herein refers to a preparation of sulfated glycosaminoglycans (GAGs) having an average molecular weight of less than 8000 Da, with about at least 60% of the oligosaccharide chains of a LMWH preparation having a molecular weight of less than 8000 Da. Several LMWH preparations are commercially available, but, LMWHs can also be prepared from heparin, using e.g., HLGAG degrading enzymes. HLGAG degrading enzymes include but are not limited to heparinase-I, heparinase-II, heparinase-III, heparinase IV, heparanase, D-glucuronidase and L-iduronidase. The three heparinases from *Flavobacterium heparinum* are enzymatic tools that have been used for the generation of LMWH (5,000-8,000 Da) and ultra-low molecular weight heparin (~3,000 Da). In addition, LMWHs can be prepared using, e.g., the *B. thetaiotaomicron* HSGAG lyase polypeptides described herein. Commercially available LMWH include, but are not limited to, enoxaparin (brand name Lovenox; Aventis Pharmaceuticals), dalteparin (Fragmin, Pharmacia and Upjohn), certoparin (Sandobarin, Novartis), ardeparin (Normiflo, Wyeth Lederle), nadroparin (Fraxiparine, Sanofi-Winthrop), parnaparin (Fluxum, Wassermann), reviparin (Clivarin, Knoll A G), and tinzaparin (Innohep, Leo Laboratories, Logiparin, Novo Nordisk). Some preferred forms of LMWH include enoxaparin (Lovenox) and dalteparin (Fragmin). The term "Arixtra" as used herein refers to a composition which includes a synthetic pentasaccharide of methyl O-2-deoxy-6-O-sulfo-2-(sulfoamino)-α-D-glucopyranosyl-(1→4)-O-β-D-glucopyranosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-6-O-sulfo-2-(sulfoamino)-α-D-glucopyranoside, decasodium salt and derivatives thereof. A "synthetic heparin" or "synthetic HLGAG" as used herein refers to HLGAGs are synthesized compounds and are not derived by fragmentation of heparin. Methods of preparing synthetic heparins are provided, for example, in Petitou et al. (1999) Nature 398:417, the contents of which is incorporated herein by reference.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, refers to a mammal organism. In a preferred embodiment, the subject is a human. In another embodiment, the subject is an experimental animal or animal suitable as a disease model. Non-limiting examples of such subjects include mice, rats, and rabbits. The subject can also be a non-human animal, e.g., a horse, cow, goat, or other domestic animal.

Various aspects of the invention are described in further detail below.

Isolated Nucleic Acid Molecules

In one aspect, the invention provides, an isolated or purified, nucleic acid molecule that encodes a *B. thetaiotaomicron* HSGAG lyase polypeptide described herein, e.g., a full length *B. thetaiotaomicron* HSGAG lyase protein or a fragment thereof, e.g., a biologically active portion of *B. thetaiotaomicron* HSGAG lyase protein. Also included is a nucleic acid fragment suitable for use as a hybridization probe, which can be used, e.g., to identify a nucleic acid molecule encoding a polypeptide of the invention, *B. thetaiotaomicron* HSGAG lyase mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1 or SEQ ID NO:5, or a portion of any of these nucleotide sequences. In one embodiment, the nucleic acid molecule includes sequences encoding the *B. thetaiotaomicron* HSGAG lyase protein (i.e., "the coding region" of SEQ ID NO:1 or SEQ ID NO:5), as well as 5' untranslated sequences. Alternatively, the nucleic acid molecule can include no flanking sequences which normally accompany the subject sequence. In another embodiment, an isolated nucleic acid molecule of the invention includes a nucleic acid molecule which is a complement of the nucleotide sequence shown in SEQ ID NO:1 or SEQ ID NO:5, or a portion of any of these nucleotide sequences. In other embodiments, the nucleic acid molecule of the invention is sufficiently complementary to the nucleotide sequence shown in SEQ ID NO:1 or SEQ ID NO:5, such that it can hybridize to the nucleotide sequence shown in SEQ ID NO:1 or SEQ ID NO:5, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:5, or a portion, preferably of the same length, of any of these nucleotide sequences.

A nucleic acid molecule of the invention can include only a portion of the nucleic acid sequence of SEQ ID NO:1 or SEQ ID NO:5. A nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment encoding a "biologically active portion of a B. thetaiotaomicron HSGAG lyase polypeptide" can be prepared by isolating a portion of the nucleotide sequence of SEQ ID NO:1, 3, 5, 7, 9 or 22, which encodes a polypeptide having a HSGAG lyase biological activity (e.g., the biological activities of HSGAG lyase proteins are described herein), expressing the encoded portion of the B. thetaiotaomicron HSGAG lyase protein (e.g., by recombinant expression in vitro) and assessing the activity of the encoded portion of the B. thetaiotaomicron HSGAG lyase protein. A nucleic acid fragment encoding a biologically active portion of a B. thetaiotaomicron HSGAG lyase polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900 or more nucleotides in length and hybridizes under stringent hybridization conditions to a nucleic acid molecule of SEQ ID NO:1, 3, 5, 7, 9 or 22.

The invention encompasses nucleic acid molecules that differ from the nucleotide sequence shown in SEQ ID NO:1, 3, 5, 7, 9 or 22. Such differences can be due to degeneracy of the genetic code (and result in a nucleic acid which encodes the same B. thetaiotaomicron HSGAG lyase proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 4, 6, 8, 10 or 23. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus) and homologs (different locus), or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1, 3, 5, 7, 9 or 23, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Homologs and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:2, 4, 6, 8, 10 or 23, or a fragment of these sequences. Such nucleic acid molecules can readily be identified as being able to hybridize under stringent conditions, to the nucleotide sequence shown in SEQ ID NO 2, SEQ ID NO:6, or a fragment of the sequence. Nucleic acid molecules corresponding to homologs and allelic variants of the B. thetaiotaomicron HSGAG lyase DNAs of the invention can further be isolated by mapping to the same chromosome or locus as the B. thetaiotaomicron HSGAG lyase gene.

Preferred variants include those that are correlated with a HSGAG lyase activity described herein.

Allelic variants of B. thetaiotaomicron HSGAG lyase include both functional and non-functional proteins. Functional allelic variants are naturally occurring amino acid sequence variants of the B. thetaiotaomicron HSGAG lyase protein within a population that maintain one or more HSGAG lyase activity. Functional allelic variants will typically contain only conservative substitution of one or more amino acids of SEQ ID NO:2, or substitution, deletion or insertion of non-critical residues in non-critical regions of the protein. Examples of functional variants include the M17, Q26, Q23 and K169 variants described herein (i.e., SEQ ID NOs: 4, 23, 8 and 10, respectively). Non-functional allelic variants are naturally-occurring amino acid sequence variants of the B. thetaiotaomicron HSGAG lyase protein within a population that do not have one or more of the HSGAG lyase activities described herein. Non-functional allelic variants will typically contain a non-conservative substitution, a deletion, or insertion, or premature truncation of the amino acid sequence of SEQ ID NO:2 or SEQ ID NO:6, or a substitution, insertion, or deletion in critical residues or critical regions of the protein.

Moreover, nucleic acid molecules encoding other B. thetaiotaomicron HSGAG lyase family members and, thus, which have a nucleotide sequence which differs from the B. thetaiotaomicron HSGAG lyase sequences of SEQ ID NO:1 or SEQ ID NO:5 are intended to be within the scope of the invention.

Isolated B. thetaiotaomicron HSGAG Lyase Polypeptides In another aspect, the invention features, isolated B. thetaiotaomicron HSGAG lyase proteins, and fragments thereof, e.g., biologically active portions thereof. B. thetaiotaomicron HSGAG lyase protein can be isolated from cells or tissue sources using standard protein purification techniques. B. thetaiotaomicron HSGAG lyase protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a B. thetaiotaomicron HSGAG lyase polypeptide has one or more of the following characteristics: (1) binds a heparin and/or a heparan sulfate; (2) cleaves one or more glycosidic linkages of a heparin and/or a heparan sulfate; (3) modulates, e.g., increases or reduces, anti-Xa activity and/or anti-IIa activity of a heparin and/or a heparan sulfate; and (4) reduces or eliminates angiogenesis.

In some embodiments, the B. thetaiotaomicron HSGAG lyase is B. thetaiotaomicron HSGAG lyase I and the B. thetaiotaomicron HSGAG lyase I can have one or more of the following activities: (1) binds a heparin and/or heparan sulfate; (2) cleaves one or more glycosidic linkages of heparin and/or heparan sulfate, e.g., cleaves one or more glycosidic linkages of sulfated uronic acids, e.g., 2-O and/or 3-O sulfated uronic acids; (3) reduces anti-Xa activity and/or anti-IIa activity of a heparin and/or a heparan sulfate, e.g., as compared to a reference standard, e:g., the anti-Xa activity and/or anti-IIa activity of a commercially available heparin or heparan sulfate or of the heparin or heparan sulfate prior to cleavage. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity are reduced.

In some embodiments, the B. thetaiotaomicron HSGAG lyase is B. thetaiotaomicron HSGAG lyase II and the B. thetaiotaomicron HSGAG lyase II can have one or more of the following activities: (1) binds a heparin and/or heparan sulfate; (2) cleaves one or more glycosidic linkages of heparin and/or heparan sulfate, e.g., cleaves one or more glycosidic linkages of sulfated and undersulfated uronic acids; (3) increases anti-Xa activity and/or anti-IIa activity of a heparin and/or a heparan sulfate, e.g., as compared to a reference standard, e.g., the anti-Xa activity and/or anti-IIa activity of a commercially available heparin or heparan sulfate or of the heparin or heparan sulfate prior to cleavage. In some embodiments, anti-Xa activity is increased while anti-IIa activity is maintained or reduced. In other embodiments, anti-IIa activity is increased while anti-Xa activity is maintained or reduced. In other embodiments, anti-Xa activity and anti-IIa activity are increased.

In a preferred embodiment, the B. thetaiotaomicron HSGAG lyase protein, or fragment thereof, differs from the corresponding sequence in SEQ ID NO:2, 4, 6, 8, 10 or 23. In one embodiment, it differs by at least one but by less than 15, 10 or 5 amino acid residues. In another, it differs from the corresponding sequence in SEQ ID NO:2, 4, 6, 8, 10 or 23 by at least one residue but less than 20%, 15%, 10% or 5% of the residues in it differ from the corresponding sequence in SEQ ID NO:2, 4, 6, 8, 10 or 23. (If this comparison requires alignment the sequences should be aligned for maximum homology. "Looped" out sequences from deletions or insertions, or mismatches, are considered differences.) The differences are, preferably, differences or changes at a non essential residue or a conservative substitution.

Other embodiments include a protein that contain one or more changes in amino acid sequence, e.g., a change in an amino acid residue which is not essential for activity. Such B. thetaiotaomicron HSGAG lyase proteins differ in amino acid sequence from SEQ ID NO:2, 4, 6, 8, 10 or 23, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2, 4, 6, 8, 10 or 23.

Biologically active portions, in which regions of the protein are deleted, can be prepared by recombinant techniques and evaluated for one or more of the functional activities of a native B. thetaiotaomicron HSGAG lyase protein.

In a preferred embodiment, the B. thetaiotaomicron HSGAG lyase protein has an amino acid sequence shown in SEQ ID NOs:2, 4, 6, 8, 10 or 23. In other embodiments, the B. thetaiotaomicron HSGAG lyase protein is substantially identical to SEQ ID NOs:2, 4, 6, 8, 10 or 23. In yet another embodiment, the B. thetaiotaomicron HSGAG lyase protein is substantially identical to SEQ ID NOs:2, 4, 6, 8, 10 or 23 and retains the functional activity of the protein of SEQ ID NO:2, 4, 6, 8, 10 or 23, as described in detail in the subsections above.

In another aspect, the invention provides B. thetaiotaomicron HSGAG lyase chimeric or fusion proteins. As used herein, a B. thetaiotaomicron HSGAG lyase "chimeric protein" or "fusion protein" includes a B. thetaiotaomicron HSGAG lyase polypeptide linked to a non-B. thetaiotaomicron HSGAG lyase polypeptide. A "non-B. thetaiotaomicron HSGAG lyase polypeptide" refers to a polypeptide having an amino acid sequence corresponding to a protein which is not substantially homologous to the B. thetaiotaomicron HSGAG lyase protein, e.g., a protein which is different from the B. thetaiotaomicron HSGAG lyase protein and which is derived from the same or a different organism. The B. thetaiotaomicron HSGAG lyase polypeptide of the fusion protein can correspond to all or a portion e.g., a fragment described herein, of a B. thetaiotaomicron HSGAG lyase amino acid sequence. In a preferred embodiment, a B. thetaiotaomicron HSGAG lyase fusion protein includes at least one (or two) biologically active portion of a B. thetaiotaomicron HSGAG lyase protein. The non-B. thetaiotaomicron HSGAG lyase polypeptide can be fused to the N-terminus or C-terminus of the B. thetaiotaomicron HSGAG lyase polypeptide.

The fusion protein can include a moiety which has a high affinity for a ligand. For example, the fusion protein can be a GST-B. thetaiotaomicron HSGAG lyase fusion protein in which the B. thetaiotaomicron HSGAG lyase sequences are fused to the C-terminus of the GST sequences. Such fusion proteins can facilitate the purification of recombinant B. thetaiotaomicron HSGAG lyase. Alternatively, the fusion protein can be a B. thetaiotaomicron HSGAG lyase protein containing a heterologous signal sequence at its N-terminus. In certain host cells (e.g., mammalian host cells), expression and/or secretion of B. thetaiotaomicron HSGAG lyase can be increased through use of a heterologous signal sequence.

Moreover, the B. thetaiotaomicron HSGAG lyase-fusion proteins of the invention can be used as immunogens to produce anti-B. thetaiotaomicron HSGAG lyase antibodies in a subject, to purify B. thetaiotaomicron HSGAG lyase ligands and in screening assays to identify molecules which inhibit the interaction of B. thetaiotaomicron HSGAG lyase with a B. thetaiotaomicron HSGAG lyase substrate.

Expression vectors are commercially available that already encode a fusion moiety (e.g., a GST polypeptide). A B. thetaiotaomicron HSGAG lyase-encoding nucleic acid can be cloned into such an expression vector such that the fusion moiety is linked in-frame to the *B. thetaiotaomicron* HSGAG lyase protein.

In another aspect, the invention also features a variant of a *B. thetaiotaomicron* HSGAG lyase polypeptide, e.g., which functions as an agonist (mimetics). Variants of the *B. thetaiotaomicron* HSGAG lyase proteins can be generated by mutagenesis, e.g., discrete point mutation, the insertion or deletion of sequences or the truncation of a *B. thetaiotaomicron* HSGAG lyase protein. An agonist of the *B. thetaiotaomicron* HSGAG lyase proteins can retain substantially the same, or a subset, of the biological activities of the naturally occurring form of a *B. thetaiotaomicron* HSGAG lyase protein.

Variants of a *B. thetaiotaomicron* HSGAG lyase protein can be identified by screening combinatorial libraries of mutants, e.g., truncation mutants, of a *B. thetaiotaomicron* HSGAG lyase protein for agonist activity. Variants of a *B. thetaiotaomicron* HSGAG lyase I include the M17 variant as shown in SEQ ID NO:4 and the Q26 variant as shown in SEQ ID NO:23. Variants of a *B. thetaiotaomicron* HSGAG lyase II include the Q23 variant as shown in SEQ ID NO:8 and the K169 variant as shown in SEQ ID NO:10.

Libraries of fragments e.g., N terminal, C terminal, or internal fragments, of a *B. thetaiotaomicron* HSGAG lyase protein coding sequence can be used to generate a variegated population of fragments for screening and subsequent selection of variants of a *B. thetaiotaomicron* HSGAG lyase protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of *B. thetaiotaomicron* HSGAG lyase proteins. Recursive ensemble mutagenesis (REM), a new technique which enhances the frequency of functional mutants in the libraries, can be used in combination with the screening assays to identify *B. thetaiotaomicron* HSGAG lyase variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated *B. thetaiotaomicron* HSGAG lyase library. For example, a library of expression vectors can be transfected into a cell line, e.g., a cell line, which ordinarily responds to *B. thetaiotaomicron* HSGAG lyase in a substrate-dependent manner. The transfected cells are then contacted with *B. thetaiotaomicron* HSGAG lyase and the effect of the expression of the mutant on the activity of the *B. thetaiotaomicron* HSGAG lyase substrate can be detected, e.g., by measuring cleavage of heparin or heparan sulfate. Plasmid DNA can then be recovered from the cells which score for inhibition, or alternatively, potentiation of signaling by the *B. thetaiotaomicron* HSGAG lyase substrate, and the individual clones further characterized.

In another aspect, the invention features a method of making a fragment or analog of a naturally occurring *B. thetaiotaomicron* HSGAG lyase polypeptide. The method includes: altering the sequence, e.g., by substitution or deletion of one or more residues, of a *B. thetaiotaomicron* HSGAG lyase polypeptide, e.g., altering the sequence of a non-conserved region, or a domain or residue described herein, and testing the altered polypeptide for the desired activity, e.g., as described above.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a *B. thetaiotaomicron* HSGAG lyase nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., *B. thetaiotaomicron* HSGAG lyase proteins, mutant forms of *B. thetaiotaomicron* HSGAG lyase proteins, fusion proteins, and the like).

The recombinant expression vectors of the invention can be designed for expression of *B. thetaiotaomicron* HSGAG lyase proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.)

which fuse glutathione S-transferase (GST), maltose E binding protein, or protein A, respectively, to the target recombinant protein.

Purified fusion proteins can be used in *B. thetaiotaomicron* HSGAG lyase activity assays, (e.g., direct assays or competitive assays described in detail below), or to generate antibodies specific for *B. thetaiotaomicron* HSGAG lyase proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The *B. thetaiotaomicron* HSGAG lyase expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In still another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1-987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a *B. thetaiotaomicron* HSGAG lyase nucleic acid molecule within a recombinant expression vector or a *B. thetaiotaomicron* HSGAG lyase nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a *B. thetaiotaomicron* HSGAG lyase protein can be expressed in bacterial cells (such as *E. coli*), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a *B. thetaiotaomicron* HSGAG lyase protein. Accordingly, the invention further provides methods for producing a *B. thetaiotaomicron* HSGAG lyase protein using the host cells of the invention. In one embodiment, the method includes culturing the host cell of the invention (into which a recombinant expression vector encoding a *B. thetaiotaomicron* HSGAG lyase protein has been introduced) in a suitable medium such that a *B. thetaiotaomicron* HSGAG lyase protein is produced. In another embodiment, the method further includes isolating a *B. thetaiotaomicron* HSGAG lyase protein from the medium or the host cell.

In another aspect, the invention features, a cell or purified preparation of cells which include a *B. thetaiotaomicron* HSGAG lyase transgene, or which otherwise misexpress *B. thetaiotaomicron* HSGAG lyase. The cell preparation can consist of human or non-human cells, e.g., rodent cells, e.g., mouse or rat cells, rabbit cells, or pig cells. In preferred embodiments, the cell or cells include a *B. thetaiotaomicron* HSGAG lyase transgene, e.g., a heterologous form of a *B. thetaiotaomicron* HSGAG lyase, e.g., a gene derived from humans (in the case of a non-human cell). The *B. thetaiotaomicron* HSGAG lyase transgene can be misexpressed, e.g., overexpressed or underexpressed. In other preferred embodiments, the cell or cells include a gene that mis-expresses an endogenous *B. thetaiotaomicron* HSGAG lyase, e.g., a gene the expression of which is disrupted, e.g., a knockout. Such cells can serve as a model for studying disorders that are related to mutated or mis-expressed *B. thetaiotaomicron* HSGAG lyase alleles or for use in drug screening.

In another aspect, the invention features, a human cell, e.g., a hematopoietic stem cell, transformed with nucleic acid which encodes a subject *B. thetaiotaomicron* HSGAG lyase polypeptide.

Also provided are cells in which a *B. thetaiotaomicron* HSGAG lyase is under the control of a regulatory sequence that does not normally control the expression of the endogenous *B. thetaiotaomicron* HSGAG lyase gene. The expression characteristics of an endogenous gene within a cell, e.g., a cell line or microorganism, can be modified by inserting a heterologous DNA regulatory element into the genome of the cell such that the inserted regulatory element is operably linked to the endogenous *B. thetaiotaomicron* HSGAG lyase gene. For example, an endogenous *B. thetaiotaomicron* HSGAG lyase gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Uses

As described herein, the *B. thetaiotaomicron* HSGAG lyase molecules of the invention are useful in many applications including, but not limited to: 1) characterization of GAGs such as heparins and heparan sulfates in terms of chemical composition (di-, tri-, tetra-, penta-, hexa-, octa-, and/or deca-oligosaccharides); 2) characterization of a pharmaceutical formulation of GAGs such as a formulation of heparin or a heparan sulfate; 3) fractionation of a GAG such as a heparin and a heparan sulfate into both its chemical constituents as well as into smaller fragments of defined length, sequence, and potential bioactivities; 4) in vitro neutralization of the anticoagulant activity (anti-Xa) of a heparin or a heparan sulfate; 5) identification of the presence and purity of a particular GAG such as a heparin or a heparan sulfate in a sample; 6) determination of the composition of a GAG in a sample; 7) determination of the sequence of di-, tetra-, hexa-, octa- and deca-saccharide units in a particular heparin or heparan sulfate; 8) use as an additional analytic tool for chemical analysis using techniques such as mass spectrometry, NMR spectroscopy, gel electrophoresis, capillary electrophoresis, HPLC, and ion-pair HPLC; 9) for cleaving a particular GAG such as a heparin or heparan sulfate that comprises at least two disaccharide units; 10) for inhibiting angiogenesis, e.g., through administration to a subject in need thereof an effective amount of a composition (e.g., a pharmaceutical composition) containing *B. thetaiotaomicron* HSGAG lyase molecules; 11) for treating cancer through the administration to a subject a composition (e.g., a pharmaceutical composition) containing *B. thetaiotaomicron* HSGAG lyase molecules; 12) inhibiting cellular proliferation through the administration to a subject in need thereof an effective amount of a composition (e.g., a pharmaceutical composition) containing *B. thetaiotaomicron* HSGAG lyase molecules for inhibiting cellular proliferation; 13) for ex vivo neutralization of the anti-Xa activity of a preparation (e.g., a pharmaceutical preparation) of a heparin or a heparan sulfate previously administered to a subject for the inhibition of coagulation; 14) for in vivo neutralization of the anti-Xa activity of preparation (e.g., a pharmaceutical preparation) of a heparin or a heparan sulfate through administration to a subject in need of such neutralization (e.g., a subject to whom a pharmaceutical preparation of a heparin or a heparan sulfate had previously been administered); 15) for ex vivo neutralization of the anti-IIa activity of a preparation (e.g., pharmaceutical preparation) of a heparin or heparan sulfate previously administered to a subject for the inhibition of thrombosis; or 16) for in vivo neutralization of the anti-IIa activity of preparation (e.g., a pharmaceutical preparation) of a heparin or a heparan sulfate through administration to a subject in need in need of such neutralization (e.g., a subject to whom a pharmaceutical preparation of a heparin or heparan sulfate had previously been administered).

Characterization and Sequencing of GAGs

Methods described herein can be used, e.g., for analyzing polysaccharides such as GAGs, (e.g., a mixed population of polysaccharides), e.g., to define the structural signature and/or activity of a polysaccharides (e.g., a mixed population of polysaccharides), by contacting the polysaccharide with a *B. thetaiotaomicron* HSGAG lyase molecule. A structural signature, as used herein, refers to information regarding, e.g., the identity and number the mono- and di-saccharide building blocks of a polysaccharide, information regarding the physiochemical properties such as the overall charge (also referred to as the "net charge" or "total charge"), charge density, molecular size, charge to mass ratio and the presence of iduronic and/or glucuronic acid content as well as the relationships between the mono- and di-saccharide building blocks, and active sites associated with these building blocks, inter alia. The structural signature can be provided by determining one or more primary outputs that include the following: the presence or the amount of one or more component saccharides or disaccharides; as used herein, "component saccharides" refers to the saccharides that make up the polysaccharide. Component saccharides can include monosaccharides, disaccharides, trisaccharides, etc., and can also include sugars normally found in nature as well as non-natural and modified sugars, e.g., that result due to production, processing and/or purification; the presence or the amount of one or more block components, wherein a "block component" is made up of more than one saccharide or polysaccharide; and the presence or amount of one or more modified saccharides, wherein a modified saccharide is one present in a starting material used to make a preparation but which is altered in the production of the preparation, e.g., a saccharide modified by cleavage. "Sequence" with respect to polysaccharides refers to the linear arrangement of covalently linked component saccharides, and can be determined by methods known in the art, e.g., the methods disclosed herein and in PCT Publication Nos: WO 00/65521, WO 02/23190, and WO 04/055491; U.S. Publication Nos: 20030191587 and 20040197933; Venkataraman (1999); Shriver et al. (2000a); Shriver et al. (2000b); and Keiser et al. (2001); the entire teachings of which are incorporated herein by reference. "Positioning of the active site" refers to a correlation between a certain component polysaccharide and a given activity.

In one embodiment, the invention provides, methods of evaluating a polysaccharide mixture, e.g., a heterogeneous population of HLGAGs, by evaluating one or more parameters related to a structural signature species described herein. Such parameters can include the presence, size distribution, or quantity of a structural signature disclosed herein. The structural signature can be one or more of the following:

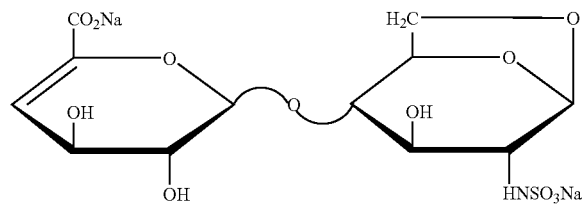
disaccharide 1
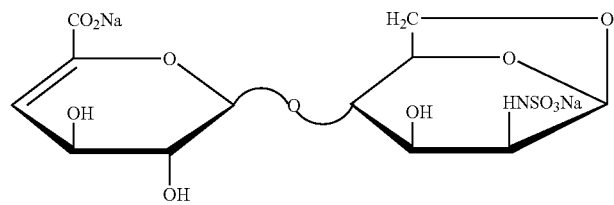
disaccharide 2
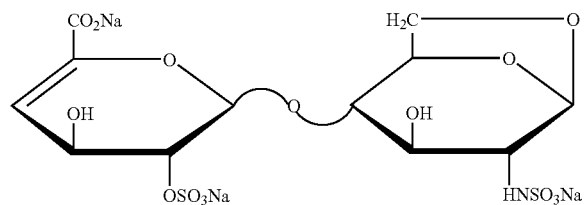
disaccharide 3
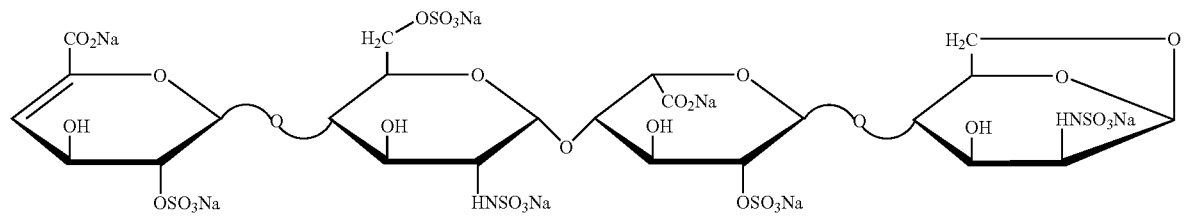
tetrasaccharide 1
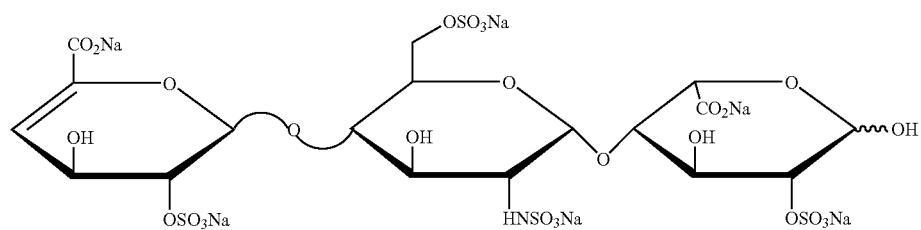
trisaccharide 1
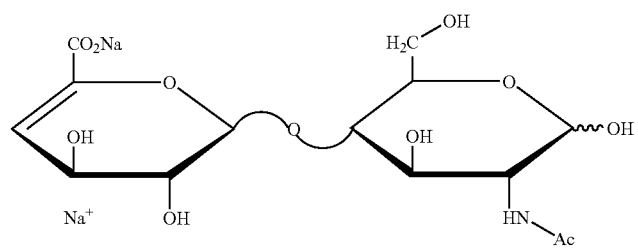
ΔIVa -continued
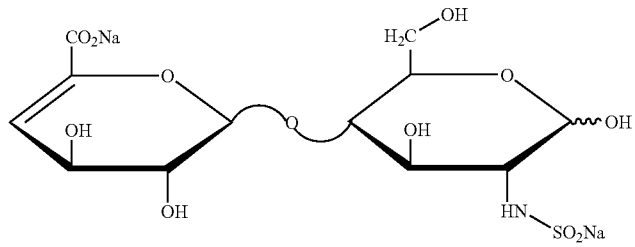
ΔIVs
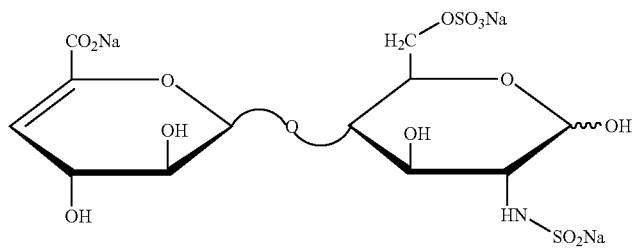
ΔIIs$_{gal}$
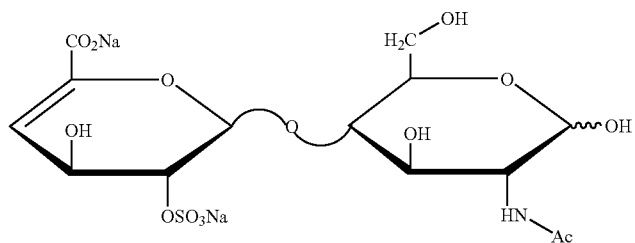
ΔIIIa
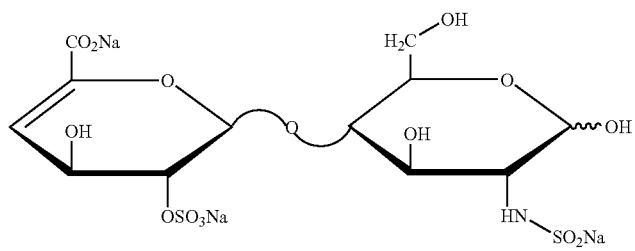
ΔIIIS
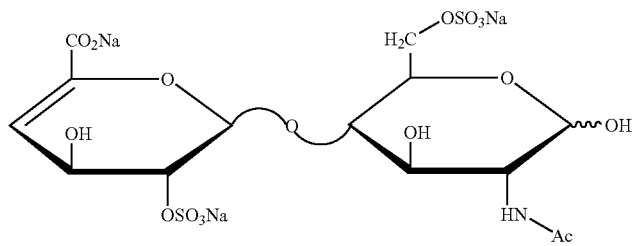
ΔIa
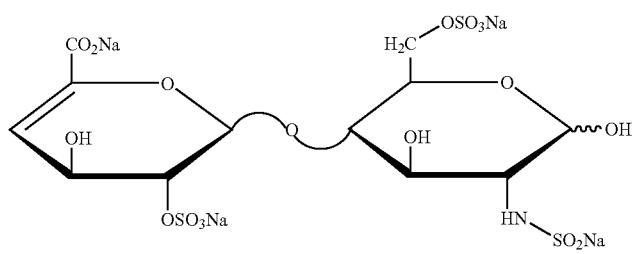

-continued
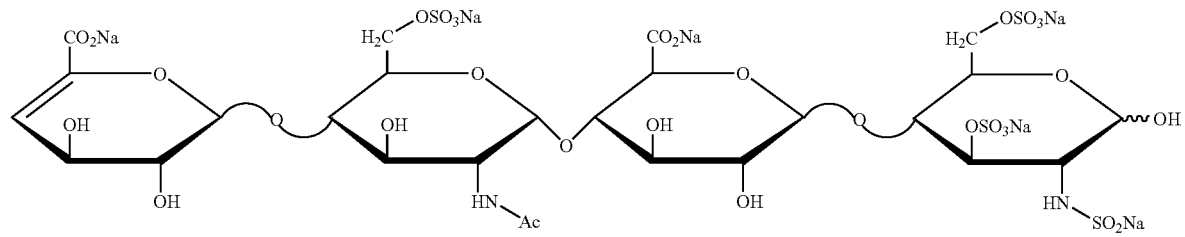
Δ UA-GlcNAc-GlcA-GlcNS(3,6S) or Δ IIa-IIs$_{glu}$
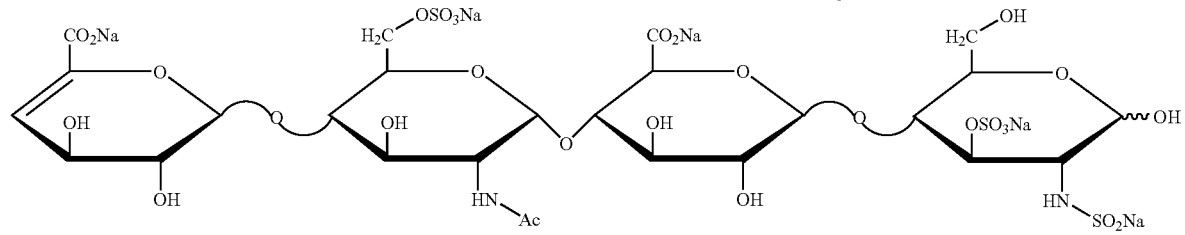
Δ UA-GlcNAc-GlcA-GlcNS(3S) or Δ IIa-IVs$_{glu}$
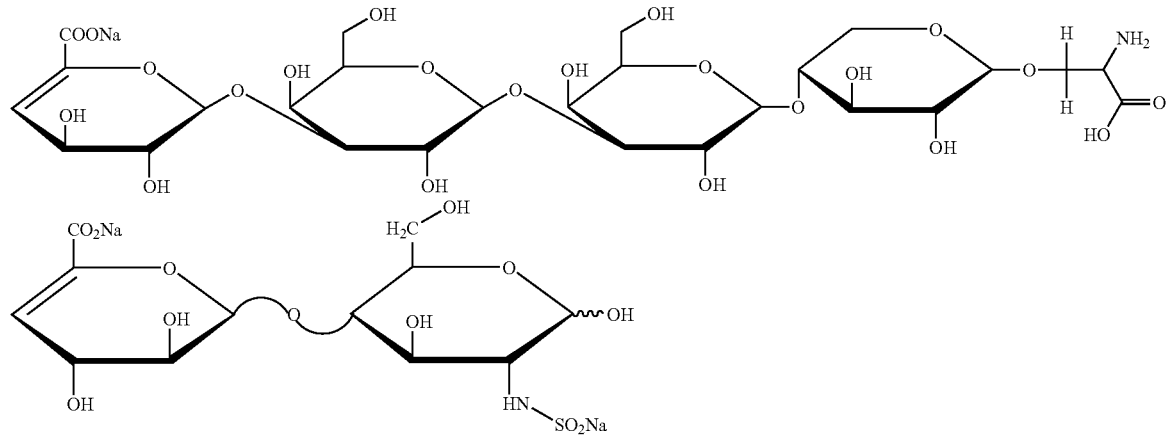
ΔIVs$_{gal}$
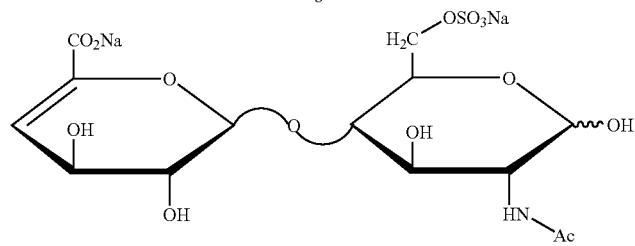
ΔIIa
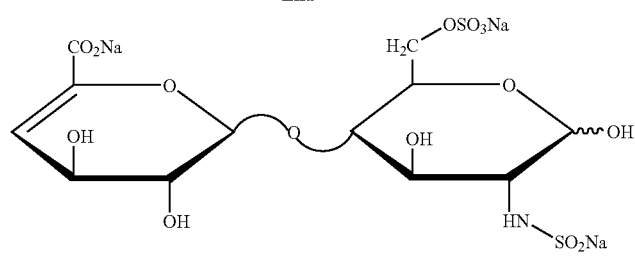
ΔIIs In a preferred embodiment, the structural signature is determined by one or more methods chosen from the group consisting of MALDI-MS, ESI-MS, CE, HPLC, FPLC, fluorometry, ELISA, chromogenic assays such as reverse phase column chromatography (e.g., HPLC), colorimetric assays, NMR and other spectroscopic techniques.

The polysaccharide composition is digested, incompletely or completely digested, with one or more *B. thetaiotaomicron* HSGAG lyase molecule. The composition can further be digested with one or more HLGAG degrading enzyme. Examples of other HLGAG degrading enzymes include: heparinase I, heparinase II, heparinase III, heparinase IV, heparanase, D-glucuronidase, L-iduronidase and functionally active variants and fragments thereof. Various HLGAG degrading enzymes, and variants and fragments thereof, are known and described, e.g., in U.S. Pat. Nos: 5,569,600; 5,389, 539; 5,830,726; 5,714,376; 5,919,693; 5,681,733 and 6,869, 789; and U.S. Patent Publications Nos: 20030099628; 20030303301; and 20010565375, the contents of which are incorporated herein by reference.

The methods described herein can further include: providing or determining a first structural signature by contacting a batch of a polysaccharide (e.g., a heterogenous population of polysaccharides) with a *B. thetaiotaomicron* HSGAG lyase molecule or molecules; providing or determining a second structural signature of a different batch of a polysaccharide (e.g., a heterogenous population of polysaccharides) by contacting the batch with a *B. thetaiotaomicron* HSGAG lyase molecule or molecules; and comparing the first and second structural determinations to determine if one or more of the batches has a structural determination associated with a particular property. The methods can further include selecting or discarding a batch of the polysaccharide depending on its structural determination.

In other embodiments, a batch of a polysaccharide (e.g., a heterogenous population of polysaccharides) can be analyzed by comparing one or more structural signature of the polysaccharide obtained by contacting the polysaccharide with one or more *B. thetaiotaomicron* HSGAG lyase molecules to a reference standard. The reference standard can be, e.g., a preselected range or level and/or the absence or presence of a structural signature present in a mixed population of polysaccharides, e.g., a commercially available population of polysaccharides such as enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™), that has been digested with the *B. thetaiotaomicron* HSGAG lyase molecule or molecules.

The *B. thetaiotaomicron* HSGAG lyase molecules can also be used to determine a reference standard for a drug by analyzing a composition contacted with a *B. thetaiotaomicron* HSGAG lyase molecule or molecules and determining the bioequivalence and/or bioavailability of one or more of the components in the mixture. As used herein, "bioequivalence" means "the absence of a significant difference in the rate and extent to which an active ingredient or active moiety in pharmaceutical equivalents or pharmaceutical alternatives becomes available at the site of drug action when administered at the same molar dose under similar conditions."

Production of Fractionated HLGAG Preparations

The *B. thetaiotaomicron* HSGAG lyase molecules described herein can be used to produce polysaccharides (e.g., fractionated heparin or heparan sulfate), e.g., having desired properties, e.g., desired activities and/or reduced undesired properties, e.g., undesired side effects. As used herein, "desired activities" refers to those activities that are beneficial for a given indication, e.g., a positive patient reaction as defined herein, inter alia. An "undesirable activity" may include those activities that are not beneficial for a given indication, e.g., a negative patient reaction, as defined herein, inter alia. A given activity may be a desired activity for one indication, and an undesired activity for another, such as anti-IIa activity, which while undesirable for certain indications, is desirable in others, notably acute or trauma situations. Thus, the invention relates to methods for designing heparins, LMWHs or synthetic heparins with ideal product profiles including, but not limited to such features as high activity, e.g., high anti-Xa and/or anti-IIa activity, reduced activity, e.g., reduced anti-Xa and/or anti-IIa activity, well characterized, neutralizable, lower side effects including reduced HIT, attractive pharmacokinetics, and/or reduced PF4 binding.

Fractionated heparins can be designed, e.g., by contacting composition that includes a mixed population of polysaccharides, such as glycosaminoglycans (GAGs), HLGAGs, UFH, FH, LMWHs, or synthetic heparins including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™) with a *B. thetaiotaomicron* HSGAG lyase.

In some embodiments, a fractionated heparin preparation having reduced anti-Xa and/or anti-IIa activity is prepared by contacting a heparin with a *B. thetaiotaomicron* HSGAG lyase I molecule. In some embodiments, anti-Xa activity is reduced while anti-IIa activity is maintained or increased. In other embodiments, anti-IIa activity is reduced while anti-Xa activity is maintained or enhanced. In other embodiments, anti-Xa activity and anti-IIa activity are reduced. Heparins having reduced anti-Xa and/or anti-IIa activity can be used, e.g., as a carrier to deliver an agent, e.g., a diagnostic, prophylactic or therapeutic agent. The heparin molecule can be linked to the agent. Active agents can include a therapeutic or prophylactic polypeptide, nucleic acid, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. The therapeutic or prophylactic polypeptide can be an active derivative or fragment of such polypeptides. The active agent can also be, but is not limited to one or more of: parathyroid hormone and derivatives and fragments thereof, erythropoietin, epoetin beta, gene activated erythropoietin, second generation EPO, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, dornase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, sargramostim, lenograstim, molgramostim, mirimostim, nartograstim, oprelvekin, peptide tyrosin-tyrosin (PYY), apolipoprotein A-IV, leptin, melanocortin, amylin, orexin, adiponectin, and ghrelin. In one embodiment, the active agent is an active polypeptide, e.g., a therapeutic or prophylactic polypeptide, and the polypeptide has a molecular weight of less than 150 kDa, more preferably less than 100 kDa, and more preferably less than 50 kDa. In one embodiment, the active agent is an active polypeptide, e.g., a therapeutic or prophylactic polypeptide, and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon. In other embodiments, the heparin molecule is linked to an inactive agent. Examples of inactive agents include biological probes or contrast agents for imaging. In another embodiment, the active agent can be a small molecule drug, e.g., a small molecule drug currently available for therapeutic, diagnostic, or prophylactic use, or a drug in development. In some embodiments, the active agent is linked to one or more heparin molecules in the formulation. As an example, small molecule drugs, and protein-based drugs may be linked to heparin molecule for delivery via known chemistries such as EDC, $CNBH_4$/DMSO/Acetic Acid, etc.

The invention also relates to fractionated heparin preparations having increased anti-Xa and/or anti-IIa activity prepared by contacting a heparin with a B. thetaiotaomicron HSGAG lyase II molecule. Such preparation can be used, e.g., to treat or prevent a disease associated with coagulation, such as thrombosis, cardiovascular disease, vascular conditions or atrial fibrillation; migraine, atherosclerosis; an inflammatory disorder, such as autoimmune disease or atopic disorders; obesity or excess adipose, an allergy; a respiratory disorder, such as asthma, emphysema, adult respiratory distress syndrome (ARDS), cystic fibrosis, or lung reperfusion injury; a cancer or metastatic disorder, e.g., lipomas; diabetes; an angiogenic disorder, such as neovascular disorders of the eye, osteoporosis, psoriasis, arthritis, Alzheimer's, a subject to undergo, undergoing or having undergone surgical procedure, organ transplant, orthopedic surgery, treatment for a fracture, e.g., a hip fracture, hip replacement, knee replacement, percutaneous coronary intervention (PCI), stent placement, angioplasty, coronary artery bypass graft surgery (CABG).

Pharmaceutical Compositions

The B. thetaiotaomicron HSGAG lyase molecules, as well as heparin molecules prepared by cleavage with the B. thetaiotaomicron HSGAG lyase molecules can be incorporated into pharmaceutical compositions. Such compositions typically include a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Alternatively, the pharmaceutical composition can be used to treat a sample (e.g., blood in a bioreactor, e.g., to deheparinize blood) before the sample is introduced into a subject.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a subject, including but not limited to the severity of the disease or disorder, previous treatments, the general health and/or age of the subject, and other diseases present.

The pharmaceutical compositions can be included in a container, pack, or dispenser together with instructions for administration.

Therapeutic Applications

The *B. thetaiotaomicron* HSGAG lyase molecules can act as novel diagnostic and therapeutic agents for controlling one or more of cellular proliferative and/or differentiative disorders, e.g., by preventing or inhibiting angiogenesis of cells otherwise exhibiting or otherwise associated with unwanted proliferation and/or differentiation. Examples of cellular and/or differentiative disorders include: diabetes; arthritis, e.g., rheumatoid arthritis; ocular disorders, e.g., ocular neovascularization, diabetic retinopathy, neovascular glaucoma, retinal fibroplasias, uevitis, eye disorders associated with iris neovasculatization; and cancer, e.g., carcinoma, sarcoma, metastatic disorders or hematopoietic neoplastic disorders, e.g., leukemias.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

In another embodiment, the *B. thetaiotaomicron* HSGAG lyase molecules, e.g., the *B. thetaiotaomicron* HSGAG lyase I molecules, can act as prophylactic or therapeutic agents for controling heparin-associated disorders. Examples of such disorders include, but are not limited to, heparin-induced anticoagulation and/or angiogenesis. Thus, the *B. thetaiotaomicron* HSGAG lyase molecules, e.g., the *B. thetaiotaomicron* HSGAG lyase I molecules, can be used to reduce or eliminate (e.g., neutralize) one or more anticoagulation and/or antithrombotic properties of heparin and/or heparan sulfate, e.g., during or after surgery. In other embodiments, the *B. thetaiotaomicron* HSGAG lyase molecules, e.g., the *B. thetaiotaomicron* HSGAG lyase I molecules, can be used to deheparinized blood, e.g., in a bioreactor, e.g., a bioreactor used in heart-lung and/or kidney dialysis.

The *B. thetaiotaomicron* HSGAG lyase molecules described herein can also be used to design fractionated HLGAG preparations, e.g., heparin and/or heparan sulfate preparations. Such fractionated HLGAG preparations may have many therapeutic utilities. For instance, it is known that HLGAG compositions are useful for preventing and treating dementia, such as Alzheimer's disease, coagulation, angiogenesis, thrombotic disorders, cardiovascular disease, vascular conditions, atherosclerosis, respiratory disorders, circulatory shock and related disorders, as well as inhibiting cancer cell growth and metastasis. Each of these disorders is well-known in the art and is described, for instance, in *Harrison's Principles of Internal Medicine* (McGraw Hill, Inc., New York), which is incorporated by reference. The use of HLGAG compositions in various therapeutic methods is described and summarized in Huang, J. and Shimamura, A., Coagulation Disorders, 12, 1251-1281 (1998).

The fractionated HLGAG preparations can be used, e.g., to treat or prevent a disorder where increased presence of active FGF, e.g., aFGF and/or bFGF, is desirable.

The HLGAG preparations are useful for treating or preventing disorders associated with coagulation. When an imbalance in the coagulation pathway shifts towards excessive coagulation, the result is the development of thrombotic tendencies, which are often manifested as heart attacks, strokes, deep venous thrombosis, acute coronary syndromes (ACS) such as unstable angina, and myocardial infarcts. A "disease associated with coagulation" as used herein refers to a condition characterized by local inflammation which can result from an interruption or reduction in the blood supply to a tissue which may occur, for instance, as a result of blockage of a blood vessel responsible for supplying blood to the tissue such as is seen for myocardial or cerebral infarction or peripheral vascular disease, or as a result of emboli formation associated with conditions such as atrial fibrillation or deep venous thrombosis. Coagulation disorders include, but are not limited to, cardiovascular disease and vascular conditions such as cerebral ischemia. It is particularly useful to treat disorders such as myocardial infarction and ACS with, e.g., a polysaccharide by pulmonary delivery because of the fast absorption and action of this delivery system.

The fractionated HLGAG preparations are useful for treating cardiovascular disease. Cardiovascular diseases include, but are not limited to, acute myocardial infarction, ACS, e.g., unstable angina, and atrial fibrillation. Myocardial infarction is a disease state which sometimes occurs with an abrupt decrease in coronary blood flow that follows a thrombotic occlusion of a coronary artery previously narrowed by atherosclerosis. Such injury may be produced or facilitated by factors such as cigarette smoking, hypertension, and lipid accumulation. Acute angina is due to transient myocardial ischemia. This disorder is usually associated with a heaviness, pressure, squeezing, smothering, or choking feeling below the sternum. Episodes are usually caused by exertion or emotion, but can occur at rest.

Atrial fibrillation is a common form of arrhythmia generally arising as a result of emotional stress or following surgery, exercise, or acute alcoholic intoxication. Persistent forms of atrial fibrillation generally occur in patients with cardiovascular disease. Atrial fibrillation is characterized by disorganized atrial activity without discrete P waves on the surface ECG. This disorganized activity can lead to improper blood flow in the atrium and thrombus formation. These thrombi can embolize, resulting in cerebral ischemia and other disorders.

Persons undergoing surgery, anesthesia and extended periods of bed rest or other inactivity are often susceptible to a condition known as deep venous thrombosis, or DVT, which is a clotting of venous blood in the lower extremities and/or pelvis. This clotting occurs due to the absence of muscular activity in the lower extremities required to pump the venous blood (stasis), local vascular injury or a hypercoaguble state. The condition can be life-threatening if a blood clot migrates to the lung, resulting in a "pulmonary embolus" or otherwise interferes with cardiovascular circulation. One method of treatment involves administration of an anti-coagulant.

The fractionated HLGAG preparations can be used for the treatment of cardiovascular disorders alone or in combination with other therapeutic agents for reducing the risk of a cardiovascular disease or for treating the cardiovascular disease. Other therapeutic agents include, but are not limited to, anti-inflammatory agents, anti-thrombotic agents, anti-platelet agents, fibrinolytic agents, lipid reducing agents, direct thrombin inhibitors, anti-Xa inhibitors, anti-IIa inhibitors, glycoprotein IIb/IIIa receptor inhibitors and direct thrombin inhibitors such as hirudin, hirugen, Angiomax, agatroban, PPACK, thrombin aptamers.

The HLGAG preparations are also useful for treating vascular conditions. Vascular conditions include, but are not limited to, disorders such as deep venous thrombosis, peripheral vascular disease, cerebral ischemia, including stroke, and pulmonary embolism. A cerebral ischemic attack or cerebral ischemia is a form of ischemic condition in which the blood supply to the brain is blocked. This interruption or reduction in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The HLGAG preparations are useful for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption or reduction in blood flow to the brain resulting from either a thrombus or embolism. A stroke causes a loss of neurons typically resulting in a neurologic deficit that may improve but that does not entirely resolve.

Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The rapid absorption of HLGAGs, such as UFH or LMWH, after inhalation can be very valuable in the treatment of venous thromboembolism. Intravenous administration of UFH has been used widely for treatment of venous thromboembolism in combination with oral warfarin. Due to the improved efficacy and reduced risks, however, LMWHs have been increasingly used as an alternative to intravenous UFH in treatment of venous thromboembolism. It has been established that efficacy of heparin therapy depends on achieving critical therapeutic levels (e.g., of values of anti-factor Xa or anti-factor IIa activity) within the first 24 hours of treatment. Intrapulmonary delivery of heparin particles to achieve rapid therapeutic levels of heparin in the early stage of thromboembolism, could also be combined with other routes of administration of LMWHs or heparin for prolonged antithrombotic/anticoagulant effect such as oral administration.

The HLGAG preparations can also be used to treat acute thromboembolic stroke. An acute stroke is a medical syndrome involving neurological injury resulting from an ischemic event, which is an interruption or reduction in the blood supply to the brain.

An effective amount of a HLGAG preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment described herein. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The pharmaceutical HLGAG preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, warfarin, Coumadin, dicumarol, phenprocoumon, acenocoumarol, ethyl biscoumacetate, and indandione derivatives. "Direct thrombin inhibitors" include hirudin, hirugen, Angiomax, agatroban, PPACK, thrombin aptamers. Antiplatelet agents inhibit platelet aggregation and are often used to prevent thromboembolic stroke in patients who have experienced a transient ischemic attack or stroke. Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v.25 (7 suppl), p. 10S-17S(1995)).

Pulmonary embolism as used herein refers to a disorder associated with the entrapment of a blood clot in the lumen of a pulmonary artery, causing severe respiratory dysfunction. Pulmonary emboli often originate in the veins of the lower extremities where clots form in the deep leg veins and then travel to lungs via the venous circulation. Thus, pulmonary embolism often arises as a complication of deep venous thrombosis in the lower extremity veins. Symptoms of pulmonary embolism include acute onset of shortness of breath, chest pain (worse with breathing), and rapid heart rate and respiratory rate. Some individuals may experience haemoptysis.

The HLGAG preparations and methods are also useful for treating or preventing atherosclerosis. Heparin has been shown to be beneficial in prevention of atherosclerosis in various experimental models. Due to the more direct access to the endothelium of the vascular system, inhaled heparin can be useful in prevention of atherosclerosis. Atherosclerosis is one form of arteriosclerosis that is believed to be the cause of most coronary artery disease, aortic aneurysm and atrial disease of the lower extremities, as well as contributing to cerebrovascular disease.

Due to its fast absorption and variable elimination rate, HLGAG with or without excipients can be used as an alternative for the intravenous heparin for surgical and dialysis procedures. For example, HLGAG particles can be inhaled prior to surgery by volunteer inhalation or passively inhaled via trachea tube during the anesthesia prior to or during the surgery. Surgical patients, especially those over the age of 40 years have an increased risk of developing deep venous thrombosis. Thus, the use of HLGAG particles for preventing the development of thrombosis associated with surgical procedures is contemplated. In addition to general surgical procedures such as percutaneous intervention (e.g., percutaneous coronary intervention (PCI)), PCTA, stents and other similar approaches, hip or knee replacement, cardiac-pulmonary by-pass surgery, coronary revascularization surgery, orthopedic surgery, and prosthesis replacement surgery, the methods are also useful in subjects undergoing a tissue or organ transplantation procedure or treatment for fractures such as hip fractures.

In addition, pulmonary inhalation of heparin is valuable in treatment of respiratory diseases such as cystic fibrosis, asthma, allergy, emphysema, adult respiratory distress syndrome (ARDS), lung reperfusion injury, and ischemia-reperfusion injury of the lung, kidney, heart, and gut, and lung tumor growth and metastasis.

Cystic fibrosis is a chronic progressive disease affecting the respiratory system. One serious consequence of cystic fibrosis is *Pseudomonas aeruginosa* lung infection, which by itself accounts for almost 90% of the morbidity and mortality in cystic fibrosis. Therapeutics for treating cystic fibrosis include antimicrobials for treating the pathogenic infection.

Heparin is also a well established inhibitor of elastase and tumor growth and metastasis. The aerosolized heparin particles are capable of inhibiting elastase induced lung injury in an acute lung emphysema model. Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Heparin is capable of inhibiting this elastase induced injury. Adult respiratory distress syndrome is a term which encompasses many acute defuse infiltrative lung lesions of diverse ideologies which are accompanied by severe atrial hypoxemia. One of the most frequent causes of ARDS is sepsis. Inflammatory diseases include but are not limited to autoimmune diseases and atopic disorders. Other types of inflammatory diseases which are treatable with HLGAGs are refractory ulcerative colitis, Chrohn's disease, multiple sclerosis, autoimmune disease, non-specific ulcerative colitis and interstitial cystitis.

In one embodiment, the HLGAG preparations are used for inhibiting angiogenesis. An effective amount for inhibiting angiogenesis of the HLGAG preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in the generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of HLGAG preparation which is sufficient to diminish the number of blood vessels growing into a tumor. This amount can be assessed in an animal model of tumors and angiogenesis, many of which are known in the art. Angiogenic disorders include, but are not limited to, neovascular disorders of the eye, osteoporosis, psoriasis, arthritis, cancer and cardiovascular disorders.

The HLGAG preparations are also useful for inhibiting neovascularization associated with eye disease. In another embodiment, the HLGAG preparation is administered to treat psoriasis. Psoriasis is a common dermatologic disease caused by chronic inflammation.

HLGAG containing compositions, may also inhibit cancer cell growth and metastasis. Thus the methods are useful for treating and/or preventing tumor cell proliferation or metastasis in a subject. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; leukemias, lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

A subject in need of cancer treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

OTHER EMBODIMENTS

This invention is further illustrated by the following examples that should not be construed as limiting. The contents of all references, patents and published patent applications cited throughout this application are incorporated herein by reference.

EXAMPLES

Example 1

Cloning and Recombinant Expression of *B. thetaiotaomicron* HSGAG Lyase I

The *B. thetaiotaomicron* HSGAG lyase I sequence (FIG. 1; SEQ ID NO:1), which is approximately 1130 nucleotides long contains a predicted methionine-initiated coding sequence of about 1128 nucleotides, including the termination codon (SEQ ID NO:1 in FIG. 1A). The coding sequence encodes a 376 amino acid protein (SEQ ID NO:2 in FIG. 1B).

The *B. thetaiotaomicron* HSGAG lyase sequence is structurally similar to the *F. heparinum* heparinase I sequence. A comparison of the amino acid sequences of the two lyases is shown in FIG. 2.

The *B. thetaiotaomicron* HSGAG lyase gene was cloned by PCR using genomic DNA from *B. thetaiotaomicron* obtained from the American Type Culture Collection (ATCC), catalog no. 29148D. DNA oligonucleotide primers for M17 variant were synthesized by Integrated DNA technologies, Inc. (IDT) according to the following nucleotide sequences: 1) 5' CATATGCTGACTGCTCAGAC-TAAAAATAC 3' (forward primer) (SEQ ID NO:11); 2) 5' CTCGAGTTATCTTTCCGAATATCCTGCGAGAT 3' (reverse primer) (SEQ ID NO:12). Primers were designed to introduce NdeI and XhoI endonuclease restriction sites at the 5' and 3' ends, respectively. The resulting gene sequence was cloned into pET28a bacterial expression plasmid (EMD Biosciences) as an NdeI-XhoI fragment for subsequent recombinant expression into *E. coli* strain BL21 (DE3), as an engineered fusion protein containing the sequence MGSSHHHHHHSSGLVPRGSH (SEQ ID NO:13) fused to the amino terminus of the *B. thetaiotaomicron* HSGAG lyase beginning at the methionine at position 17 (M17).

A *B. thetaiotaomicron* HSGAG lyase variant with a modified amino terminus that begins at position glutamine 26 (Q26) of the protein sequence listed in SEQ ID NO:2, was cloned into pET28a for recombinant expression as a fusion protein. The amino acid sequence and nucleic acid sequence encoding the Q26 variant are provided in SEQ ID NOs: 4 and 3, respectively DNA oligonucleotide primers for Q26 variant were synthesized by Integrated DNA technologies, Inc. (IDT) according to the following nucleotide sequences: 1) 5' CAT ATG CAA ACA CTG ATG CCA CTC ACC GAA 3' (forward primer) (SEQ ID NO:24) and 5' CTCGAGTTATCTTTC-CGAATATCCTGCGAGAT 3' (reverse primer) (SEQ ID NO:12).

Both the full length, M17, and Q26 *B. thetaiotaomicron* HSGAG lyase fusion proteins were recombinantly expressed in *E. coli*, yielding soluble, highly active enzyme that was fully capable of cleaving heparin and heparan sulfate (see Example 2 below). [Sequence verified plasmid pET28 containing either the M17 coding sequence or Q26 coding sequence was transformed into BL21 (DE3). 2 liter cultures were grown at room temperature (~20° C.) in LB media supplemented with 40 µg/mL kanamycin. Protein expression was induced with 500 µM IPTG added at an $A_{600}$ of 1.0. Induced cultures were allowed to grow for 15-18 hours at room temperature.

Recombinant *B. thetaiotaomicron* HSGAG lyase purification. Bacterial cells were harvested by centrifugation at 6000×g for 15 minutes and resuspended in 30 mL of binding buffer (50 mM $Na_2HPO_4$, pH 7.9, 0.5 M NaCl, and 5 mM imidazole). Lysis was initiated by the addition of 0.1 mg/mL lysozyme (20 minutes at room temperature) followed by intermittent sonication in an ice-water bath using a Misonex XL sonicator at 40-50% output. The crude lysate was fractionated by low-speed centrifugation (20,000×g; 4° C.; 30 minutes) and the supernatant was filtered through a 0.45 micron filter. The 6x-His recombinant *B. thetaiotaomicron* HSGAG lyase was purified by $Ni^{+2}$ chelation chromatography on a 5 mL Hi-Trap column (GE Healthcare,) pre-charged with 200 mM $NiSO_4$ and subsequently equilibrated with binding buffer. The column was run at a flow rate of approximately 3 ml/minute that included an intermediate wash step with 50 mM imidazole. The lyase enzyme was eluted from the column in 5 mL fractions using high imidazole elution buffer (50 mM $Na_2HPO_4$, pH 7.9, 0.5 M NaCl, and 250 mM imidazole).

The resulting peak was buffer exchanged on a Sephadex G-25 column equilibrated with 20 mM $Na_2HPO_4$, pH 6.8, 150 mM NaCl.

Protein concentrations were determined by the Bio-Rad protein assay and confirmed by UV spectroscopy. Protein purity was assessed by SDS-PAGE followed by Coomassie Brilliant Blue staining and/or Sypro Ruby Red.

Example 2

Distinct Heparan Sulfate Substrate Specificities of *B. thetaiotaomicron* HSGAG Lyase I and *F. heparinum* Heparinases I and II The cleavage patterns and thereby the substrate specificities of recombinant *B. thetaiotaomicron* HSGAG lyase I and *F. heparinum* heparinases I and II were compared using heparan sulfate as a substrate. 200 µg of "HI" heparan sulfate (Celsus Labs) from porcine intestinal mucosa was digested with recombinant *B. thetaiotaomicron* HSGAG lyase I under conditions favorable to ensure a complete digestion. The HI was contacted with about 50 µg *B-thetaiotaomicron* HSGAG lyase I, 50 mM sodium phosphate, 100 mM NaCl, pH 8.0 at 37° C. for 18 hours. The lyase digestion products were analyzed by HPLC using strong anion chromatography (SAX—HPLC). SAX—HPLC conditions were as follows: 50 µg samples was injected at 1 mg/ml into a 4×250 mm CarboPac PA1 analytical scale comlumn (Dionex Corporation). The flow rate was 1 ml/min. The mobile phase was 0.2M to 2 M NaCl in water, pH 3.5, gradient over 120 minutes. The column was preequilibrated with 0.2 M NaCl for 10 minutes. The results are shown in FIG. 6 as trace A. FIG. 6 trace B shows the results of the same experiment except that *F. heparinum* heparinase I was used to digest the heparan sulfate. Briefly, The HI was contacted with about 50 µg *F. heparinum* heparinase I, 25 mM sodium acetate, 1 mM calcium acetate, 5% glycine, pH 7.0 at 30° C. for 18 hours. This digestion profile is very similar to the profile in trace A, except that novel peaks are present in trace A (depicted by arrows) that are not present in trace B, demonstrating that the lyases have different substrate specificities. FIG. 6 trace C shows the results of the same experiment except that *F. heparinum* heparinase II was used to digest the heparan sulfate. Briefly, The HI was contacted with about 50 µg *F. heparinum* heparinase II, 25 mM sodium acetate, 1 mM calcium acetate, pH 7.0 at 37° C. for 18 hours. In this case, the digestion profile is very much distinct from A (*B. thetaiotaomicron* HSGAG lyase ) and B (*F. heparinum* heparinase I). These data demonstrate that the *B. thetaiotaomicron* HSGAG lyase substrate specificity is distinct from the specificities of *F. heparinum* heparinases I and II, but is more "heparin like" (e.g., more similar to *F. heparinum* heparinase I) than "heparan sulfate-like" (e.g., it is less like *F. heparinum* heparinase II).

Example 3

Figure 8:
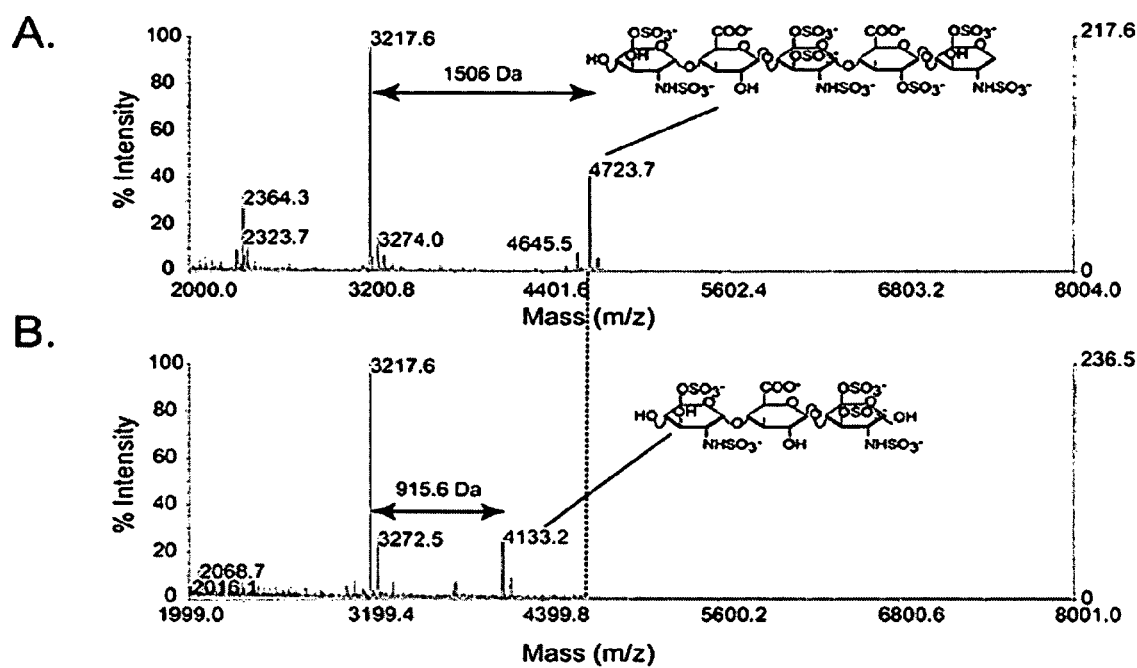
FIG. 8 is a representation of a MALDI-MS mass spectrum. Panel A depicts the peaks of untreated ATIII pentasaccharide ARIXTRA®, the structure of which is also shown. Panel B depicts the peaks produced after ARIXTRA® was digested with recombinant *B. thetaiotaomicron* HSGAG lyase I. A pentasulfated trisaccharide product, the structure of which is shown, results after digestion.

Depolymerization and Neutralization of ARIXTRA® by *B. thetaiotaomicron* HSGAG Lyase I Recombinant *B. thetaiotaomicron* HSGAG lyase I can cleave and thereby neutralize the ATIII pentasaccharide ARIXTRA® into a pentasulfated trisaccharide and an unsaturated disulfated disaccharide. ARIXTRA® is an anti-thrombotic drug that acts as a selective inhibitor of Factor Xa, a component of the coagulation cascade. Depolymerization of ARIXTRA® is unequivocally demonstrated by matrix assisted laser desorption ionization mass spectrometry (MALDI-MS) (FIG. 8). Panel A shows the scan of ARIX-TRA® in the absence of a lyase. The structure of ARIX-TRA® is also shown. Panel B shows the scan after cleavage of ARIXTRA® with B. thetaiotaomicron HSGAG lyase. Briefly, 1 mg/ml ARIXTRA® in a 20 μL reaction volume was treated with 5 μg B. thetaiotaomicron HSGAG lyase I, 25 mM sodium acetate, 1 mM calcium acetate, pH 7.0 at 37° C. for 2 hours. Note the disappearance in panel B of mass 4723.7 Da (net mass=1506 Da) present in panel A with concomitant appearance of mass 4133.2 Da (net mass=915.6 Da). The latter mass represents the pentasulfated trisaccharide cleavage product. In cleaving Arixtra into two smaller fragments, the drug's anti-Xa activity is effectively neutralized by the B. thetaiotaomicron HSGAG lyase.

Example 4

Cloning and Recombinant Expression of B. thetaiotaomicron HSGAG Lyase II

The complete coding sequence of a B. thetaiotaomicron heparin/heparan sulfate lyase II (herein described as "full-length gene") as well as the two variants described herein were cloned by PCR using genomic DNA from Bacteroides thetaiotaomicron as obtained from American Type Culture Collection (ATCC), catalog no. 29148D. DNA oligonucleotide primers were synthesized by Integrated DNA technologies (IDT), Inc. according to the following nucleotide sequences: 1) For the full-length gene: 5' CAT ATG AAT AAA ACC CTG AAA TAT ATC GTC CTG 3' (forward primer) (SEQ ID NO:14), 5' CTC GAG TTA TAA TTT ATA TTT TAA TGA CTG TTT CTT GC 3' (reverse primer) (SEQ ID NO:15); 2) Gene encoding variant No. 1 (amino terminal truncation to remove putative signal sequence): 5' CAT ATG CAA GAG TTG AAA AGC GAG GTA TTC TCG 3' (forward primer) (SEQ ID NO:16), 5' CTC GAG TTA TAA TTT ATA TTT TAA TGA CTG TTT CTT GC 3' (note: same reverse primer listed above as for full-length gene) (SEQ ID NO:15). Primers were designed to introduce Nde 1 and Xho 1 endonuclease restriction sites at the 5' and 3' ends, respectively. Cloning of described gene sequence into pET28b bacterial expression plasmid (EMD Biosciences) as an Nde 1-Xho 1 fragment for subsequent recombinant expression into E. coli strain BL21 (DE3) as engineered fusion protein containing the sequence MGSSHHHHHHSSGLVPRGSH-MNKTLKY . . . KVNGKKQSLKYKL (SEQ ID NO:17) or MGSSHHHHHHSSGLVPRGSHMQELKSEVF . . . KVNGKKQSLKYKL (SEQ ID NO:18) for the full-length gene and variant 1 (the Q23 variant, SEQ ID NO:8), respectively (Bacteroides thetaiotaomicron HSGAG lyase sequence is denoted in bold). See FIG. 4 for complete sequence.

Another variant, the K169 variant (SEQ ID NO:10) represents an engineered deletion of 18 contiguous amino acids comprising an internal region within the protein and possessing the following linear sequence: KMDKKEYELVS-DGKIKGE. (SEQ ID NO:19) Deletion of this region in the gene sequence (FIG. 4A) and in the corresponding protein sequence (FIG. 4B) is noted by grey shading. Deletion of this region at the DNA level was accomplished by PCR-based mutagenesis using the Quick-change kit (Stratagene) in accordance with the manufacturer's instructions. Mutagenesis primers used to make this deletion at the gene (DNA) level were of the following sequence: 5' GG ATT AAA AAG AAT CCG TTG GTG GAA AAT GTA CGT TTC GC 3' (SEQ ID NO:20) and 5' CC TAA TTT TTC TTA GGC AAC CAC CTT TTA CAT GCA AAG CG 3' (SEQ ID NO:21) corresponding to the sense and anti-sense strands, respectively. Recombinant expression of this described gene variant in E. coli likewise based on the pET-based expression for recombinant expression was also achieved.

Preliminary biochemical characterization of this variant indicates that deletion of described amino acids is not deleterious to the soluble expression of the enzyme nor to its ability to cleave both heparin and heparan sulfate. It does suggest, however a potential difference in the substrate specificity of this enzyme variant relative to the full-length protein.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of specifically cleaving a heparin or a heparan sulfate, comprising:
   selecting an isolated *B. thetaiotaomicron* HSGAG lyase polypeptide I, or a functional fragment thereof, that cleaves a heparin or a heparan sulfate such that the *B. thetaiotaomicron* HSGAG lyase polypeptide, or a functional fragment thereof, cleaves a glycosidic linkage between a glucosamine having a sulfate at position 3 and a sulfated uronic acid of the heparin or heparan sulfate, wherein the *B. thetaiotaomicron* HSGAG lyase I polypeptide, or a functional fragment thereof, comprises
   a) an amino acid sequence which is at least 90% identical to the amino acid sequence of SEQ ID NO:2;
   b) the amino acid sequence of SEQ ID NO:2, 4 or 23; and
   c) an amino acid sequence which differs by at least 1 amino acid but not more than 15 amino acids from the amino acid sequence of SEQ ID NO:2, and
   contacting the heparin or the heparan sulfate, to thereby cleave the heparin or heparan sulfate.

2. The method of claim 1, further comprising contacting the heparin or heparan sulfate with an isolated *B. thetaiotaomicron* HSGAG lyase II polypeptide, or functional fragment thereof.

3. The method of claim 1, wherein the *B. thetaiotaomicron* HSGAG lyase I polypeptide, or functional fragment thereof, is encoded by a nucleotide sequence selected from the group consisting of:
   a) a nucleic acid molecule comprising a fragment of at least 800 nucleotides of the nucleotide sequence of SEQ ID NO: 1, 3 or 22;
   b) a nucleic acid molecule which encodes a polypeptide comprising the amino acid sequence of SEQ ID NO:2, 4 or 23; and
   c) a nucleic acid molecule which encodes a fragment of a polypeptide comprising the amino acid sequence of SEQ ID NO:2, 4 or 23, wherein the fragment comprises at least 300 contiguous amino acids of SEQ ID NO:2, 4 or 23.

4. The method of claim 1 or 2, wherein the *B. thetaiotaomicron* HSGAG lyase I cleaves a heparin at one or more glycosidic linkages of 2-O sulfated uronic acids.

5. The method of claim 2, wherein the *B. thetaiotaomicron* HSGAG lyase II cleaves a heparin at one or more glycosidic linkages of sulfated or undersulfated uronic acids.

6. The method of claim 1, wherein the heparin or heparan sulfate is cleaved into di-, tri-, tetra-, penta-, hexa-, octa-, and/or deca- saccharides.

7. The method of claim 1, further comprising determining the sequence of the cleaved heparin or heparan sulfate.

8. The method of claim 7, further comprising contacting the heparin or heparan sulfate with one or more HLGAG degrading enzyme other than the *B. thetaiotaomicron* HSGAG lyase I polypeptide.

9. The method of claim 8, wherein the HLGAG degrading enzyme is selected from *Flavobacterium heparinum* heparinase I, *Flavobacterium heparinum* heparinase II, *Flavobacterium heparinum* heparinase III, *Flavobacterium heparinum* heparinase IV, heparanase, sulfatase, delta 4,5 glucuronidase and functional fragments thereof.

* * * * *

SEQUENCE LISTING

<160> NUMBER OF SEQ ID NOS: 27

<210> SEQ ID NO 1
<211> LENGTH: 1251
<212> TYPE: DNA
<213> ORGANISM: Bacteroides thetaiotaomicron

<400> SEQUENCE: 1

```
gacaaacgaa aggcagccgt aagggttgcc tttcgtattt ttgcaccgtc gataaactta        60
ataccggata gaatgaaaaa atacattttg gttatttata tgatggcggc aggatgcacg       120
atgctgactg ctcagactaa aaatacgcaa acactgatgc cactcaccga acgggtaaac       180
gtacaggctg actctgcacg tatcaaccag attattgacg gttgctgggt agctgtcggg       240
acgaataaac ctcatgccat tcagcgtgat tttaccaacc tgtttgatgg caagccctcc       300
```

-continued

```
tatcgctttg aactcaaaac tgaagacaat acactggaag gttatgcgaa aggagaaacg      360
aaaggacgtg ccgagttttc atattgctat gcaacttccg acgatttcag gggattacct      420
gccgacgttt atcagaaagc acagatcaca aagacagttt atcatcacgg aagggagct       480 tgtccgcaag gaagttcccg cgactatgag ttttcggttt atattccttc ttctttagac      540
agcaatgtct ccaccatctt tgcccaatgg cacggaatgc ccgaccggac gctggtccag      600
actcctcagg gcgaggtgaa gaaactgact gttgacgaat tgtagaact ggaaaaaacg       660 accttcttca aaagaatgt cggacacgaa aaagtggcca gactggataa acaaggtaat       720
ccggtgaaag ataaaatgg aaaacctgta tataaggcag aaaacccaa cggatggttg        780 gttgaacagg gaggataccc gccattggca ttcggatttt ccggaggact gttttatatc      840
aaagcaaact ccgaccgtaa atggctgaca gacaaagatg accgttgcaa tgcaaacccg      900
ggaaagacgc ccgttatgaa accgctgact tctgaataca aggcatccac cattgcctac      960
aaattacctt ttgccgattt cccgaaagac tgctggatta cttccgtgt ccatatcgac      1020 tggacggtct atggcaagga agcggaaacg attgtgaaac cgggcatgct ggatgtacgg     1080
atggattatc aggagcaagg taagaaagtg agcaaacaca ttgtcgataa tgagaagatt     1140
ctgattggac gtaacgacga agacgggtat tactttaagt tcggaattta ccgcgtaggt     1200
gatagtaccg ttcccgtttg ctacaatctc gcaggatatt cggaaagata a             1251
```

<210> SEQ ID NO 2
<211> LENGTH: 392
<212> TYPE: PRT
<213> ORGANISM: Bacteroides thetaiotaomicron

<400> SEQUENCE: 2

```
Met Lys Lys Tyr Ile Leu Val Ile Tyr Met Met Ala Ala Gly Cys Thr
  1               5                  10                  15

Met Leu Thr Ala Gln Thr Lys Asn Thr Gln Thr Leu Met Pro Leu Thr
             20                  25                  30

Glu Arg Val Asn Val Gln Ala Asp Ser Ala Arg Ile Asn Gln Ile Ile
         35                  40                  45

Asp Gly Cys Trp Val Ala Val Gly Thr Asn Lys Pro His Ala Ile Gln
     50                  55                  60

Arg Asp Phe Thr Asn Leu Phe Asp Gly Lys Pro Ser Tyr Arg Phe Glu
 65                  70                  75                  80

Leu Lys Thr Glu Asp Asn Thr Leu Glu Gly Tyr Ala Lys Gly Glu Thr
                 85                  90                  95

Lys Gly Arg Ala Glu Phe Ser Tyr Cys Tyr Ala Thr Ser Asp Asp Phe
            100                 105                 110

Arg Gly Leu Pro Ala Asp Val Tyr Gln Lys Ala Gln Ile Thr Lys Thr
        115                 120                 125

Val Tyr His His Gly Lys Gly Ala Cys Pro Gln Gly Ser Ser Arg Asp
    130                 135                 140

Tyr Glu Phe Ser Val Tyr Ile Pro Ser Ser Leu Asp Ser Asn Val Ser
145                 150                 155                 160

Thr Ile Phe Ala Gln Trp His Gly Met Pro Asp Arg Thr Leu Val Gln
                165                 170                 175

Thr Pro Gln Gly Glu Val Lys Lys Leu Thr Val Asp Glu Phe Val Glu
            180                 185                 190

Leu Glu Lys Thr Thr Phe Phe Lys Lys Asn Val Gly His Glu Lys Val
        195                 200                 205
```

-continued

```
Ala Arg Leu Asp Lys Gln Gly Asn Pro Val Lys Asp Lys Asn Gly Lys
    210                 215                 220
Pro Val Tyr Lys Ala Gly Lys Pro Asn Gly Trp Leu Val Glu Gln Gly
225                 230                 235                 240
Gly Tyr Pro Pro Leu Ala Phe Gly Phe Ser Gly Gly Leu Phe Tyr Ile
                245                 250                 255
Lys Ala Asn Ser Asp Arg Lys Trp Leu Thr Asp Lys Asp Asp Arg Cys
                260                 265                 270
Asn Ala Asn Pro Gly Lys Thr Pro Val Met Lys Pro Leu Thr Ser Glu
            275                 280                 285
Tyr Lys Ala Ser Thr Ile Ala Tyr Lys Leu Pro Phe Ala Asp Phe Pro
    290                 295                 300
Lys Asp Cys Trp Ile Thr Phe Arg Val His Ile Asp Trp Thr Val Tyr
305                 310                 315                 320
Gly Lys Glu Ala Glu Thr Ile Val Lys Pro Gly Met Leu Asp Val Arg
                325                 330                 335
Met Asp Tyr Gln Glu Gln Gly Lys Lys Val Ser Lys His Ile Val Asp
                340                 345                 350
Asn Glu Lys Ile Leu Ile Gly Arg Asn Asp Glu Asp Gly Tyr Tyr Phe
            355                 360                 365
Lys Phe Gly Ile Tyr Arg Val Gly Asp Ser Thr Val Pro Val Cys Tyr
    370                 375                 380
Asn Leu Ala Gly Tyr Ser Glu Arg
385                 390

<210> SEQ ID NO 3
<211> LENGTH: 1179
<212> TYPE: DNA
<213> ORGANISM: Bacteroides thetaiotaomicron

<400> SEQUENCE: 3
atgaaaaaat acattttggt tatttatatg atggcggcag atgcacgat gctgactgct          60 cagactaaaa atacgcaaac actgatgcca ctcaccgaac gggtaaacgt acaggctgac         120
tctgcacgta tcaaccagat tattgacggt tgctgggtag ctgtcgggac gaataaacct         180
catgccattc agcgtgattt taccaacctg tttgatggca agccctccta tcgctttgaa         240
ctcaaaactg aagacaatac actggaaggt tatgcgaaag gagaaacgaa aggacgtgcc         300
gagttttcat attgctatgc aacttccgac gatttcaggg gattacctgc cgacgtttat         360
cagaaagcac agatcacaaa gacagtttat catcacggga agggagcttg tccgcaagga         420
agttcccgcg actatgagtt ttcggtttat attccttctt ctttagacag caatgtctcc         480
accatctttg cccaatggca cggaatgccc gaccggacgc tggtccagac tcctcagggc         540
gaggtgaaga aactgactgt tgacgaattt gtagaactgg aaaaaacgac cttcttcaaa         600
aagaatgtcg gacacgaaaa agtggccaga ctggataaac aaggtaatcc ggtgaaagat         660
aaaaatggaa aacctgtata taaggcagga aaacccaacg gatggttggt tgaacaggga         720
ggatacccgc cattggcatt cggattttcc ggaggactgt tttatatcaa agcaaactcc         780
gaccgtaaat ggctgacaga caaagatgac cgttgcaatg caaacccggg aaagacgccc         840
gttatgaaac gctgacttc tgaatacaag gcatccacca ttgcctacaa attacctttt         900
gccgatttcc cgaaagactg ctggattact ttccgtgtcc atatcgactg gacggtctat         960
ggcaaggaag cggaaacgat tgtgaaaccg gcatgctgg atgtacggat ggattatcag        1020
gagcaaggta gaaaagtgag caaacacatt gtcgataatg agaagattct gattggacgt        1080
```

```
aacgacgaag acgggtatta ctttaagttc ggaatttacc gcgtaggtga tagtaccgtt    1140
cccgtttgct acaatctcgc aggatattcg gaaagataa                            1179
```

<210> SEQ ID NO 4
<211> LENGTH: 376
<212> TYPE: PRT
<213> ORGANISM: Bacteroides thetaiotaomicron

<400> SEQUENCE: 4

```
Met Leu Thr Ala Gln Thr Lys Asn Thr Gln Thr Leu Met Pro Leu Thr
  1               5                  10                  15

Glu Arg Val Asn Val Gln Ala Asp Ser Ala Arg Ile Asn Gln Ile Ile
             20                  25                  30

Asp Gly Cys Trp Val Ala Val Gly Thr Asn Lys Pro His Ala Ile Gln
         35                  40                  45

Arg Asp Phe Thr Asn Leu Phe Asp Gly Lys Pro Ser Tyr Arg Phe Glu
     50                  55                  60

Leu Lys Thr Glu Asp Asn Thr Leu Glu Gly Tyr Ala Lys Gly Glu Thr
 65                  70                  75                  80

Lys Gly Arg Ala Glu Phe Ser Tyr Cys Tyr Ala Thr Ser Asp Asp Phe
                 85                  90                  95

Arg Gly Leu Pro Ala Asp Val Tyr Gln Lys Ala Gln Ile Thr Lys Thr
            100                 105                 110

Val Tyr His His Gly Lys Gly Ala Cys Pro Gln Gly Ser Ser Arg Asp
        115                 120                 125

Tyr Glu Phe Ser Val Tyr Ile Pro Ser Ser Leu Asp Ser Asn Val Ser
    130                 135                 140

Thr Ile Phe Ala Gln Trp His Gly Met Pro Asp Arg Thr Leu Val Gln
145                 150                 155                 160

Thr Pro Gln Gly Glu Val Lys Lys Leu Thr Val Asp Glu Phe Val Glu
                165                 170                 175

Leu Glu Lys Thr Thr Phe Phe Lys Lys Asn Val Gly His Glu Lys Val
            180                 185                 190

Ala Arg Leu Asp Lys Gln Gly Asn Pro Val Lys Asp Lys Asn Gly Lys
        195                 200                 205

Pro Val Tyr Lys Ala Gly Lys Pro Asn Gly Trp Leu Val Glu Gln Gly
    210                 215                 220

Gly Tyr Pro Pro Leu Ala Phe Gly Phe Ser Gly Gly Leu Phe Tyr Ile
225                 230                 235                 240

Lys Ala Asn Ser Asp Arg Lys Trp Leu Thr Asp Lys Asp Arg Cys
                245                 250                 255

Asn Ala Asn Pro Gly Lys Thr Pro Val Met Lys Pro Leu Thr Ser Glu
            260                 265                 270

Tyr Lys Ala Ser Thr Ile Ala Tyr Lys Leu Pro Phe Ala Asp Phe Pro
        275                 280                 285

Lys Asp Cys Trp Ile Thr Phe Arg Val His Ile Asp Trp Thr Val Tyr
    290                 295                 300

Gly Lys Glu Ala Glu Thr Ile Val Lys Pro Gly Met Leu Asp Val Arg
305                 310                 315                 320

Met Asp Tyr Gln Glu Gln Gly Lys Lys Val Ser Lys His Ile Val Asp
                325                 330                 335

Asn Glu Lys Ile Leu Ile Gly Arg Asn Asp Glu Asp Gly Tyr Tyr Phe
            340                 345                 350
```

```
                Lys Phe Gly Ile Tyr Arg Val Gly Asp Ser Thr Val Pro Val Cys Tyr
                        355                 360                 365

Asn Leu Ala Gly Tyr Ser Glu Arg
                        370                 375

<210> SEQ ID NO 5
<211> LENGTH: 2001
<212> TYPE: DNA
<213> ORGANISM: Bacteroides thetaiotaomicron

<400> SEQUENCE: 5
atgaataaaa ccctgaaata tatcgtcctg ctgacatttg cttgtttcgt aggcaaaggc      60
tatgcccaag agttgaaaag cgaggtattc tcgcttctca acctggacta ccccggattg     120
gagaaagtaa aagccttaca tcaggaaggc aaagatgagg atgccgcaaa agcactgctc     180
gactactacc gtgcacgtac gaatgtgaag acgccggata ttaatctgaa aaagatcact     240
atcggcaaaa aagaacagca atgggcggat gacggattga agcatacatt ctttgttcac     300
aaaggctatc agccttctta caactacgga gaagatatca actggcaata ctggccggtg     360
aaagacaatg aactccgctg gcagttgcac cgtcataaat ggtttactcc gatgggtaag     420
gcataccgtg tatcgggtga cgagaaatat gccaaagaat gggcatacca atacatcgac     480
tggattaaaa agaatccgtt ggtgaagatg acaagaaag aatacgaact ggtaagtgac      540
ggtaagatta aaggcgaagt ggaaaatgta cgtttcgcat ggcgtccgct ggaagtcagt     600
aatcgtctgc aggatcagac tacccagttc cagttgttcc tcccctctcc ttctttcact     660
ccggatttcc tgactgaatt tctggtgaac tatcataaac atgccgtaca tattctggct     720
aattactctg atcagggtaa tcacttgttg ttcgaagccc agcgtatgat ttatgcaggt     780
gcattcttcc cggaatttaa agaagctccg gcctggagaa aaagcggtat cgacattctg     840
aaccgtgaag taaacgtaca ggtttacaac gatggcggcc agtttgaact tgacccgcat     900
tatcatcttg ctgctatcaa tatcttctgc aaggcattgg gtatcgcgga tgttaacgga     960
ttccgtaatg agttcccaca ggaatatctg gatactatcg aaaagatgat catgttctat    1020
gccaatattt ctttcccgga ttacacaaat ccgtgtttca gtgatgctaa atcacagaa    1080 aagaaagaaa tgctgaagaa ctatcgtgca tggagcaaac tgttcccgaa aaacgaaact    1140
atcaagtatt tggcaacaga cggcaaagaa ggcgcgttac ccgattatat gtcgaaaggt    1200
ttcctgaaat caggttttct tgtgttccgc aattcctggg aatggatgc tacacaaatg    1260 gtagtaaaag ccggtccgaa aggttctgg cactgtcagc cggataacgg tactttcgaa     1320
atgtggttta cggcaagaa cctgttccca gactccggtt cgtatgtgta tgccggtgaa    1380
ggcgaagtga tggaacaacg caactggcat cgtcagactt ccgtacacaa caccgtgact    1440
ctggacaata gaatctggaa acaaccgaa tctgttacta aactgtggca gccggaaggc    1500
aatatccaga ccttggttac agaaaaccca agctacaaga acttcaagca ccgccgttcg    1560
gtcttcttcg tagacaatac ctactttgtc attgtagatg aagtatcagg cagcgccaaa    1620
ggttctgtca acctgcacta tcagatgccg aaaggtgaga tagccaacag ccgtgaagac    1680
atgacattcc tgactcaatt cgaagatgga agcaacatga acttcaatg cttcggccct    1740 gaaggcatga gcatgaaaaa agagccggga tggtgttcta ctgcatatcg caagcgctac    1800
aaacgtatga atgtttcatt caacgtaaag aaagacaatg agaatgcggt acgttacatc    1860
acagttattt acccagtcaa gaagagcgca gatgccccta aatttgacgc taagttcaag    1920 aacaaaaacgt tcgatgaaaa cggactggaa atagaagtga agtaaacgg caagaaacag    1980
```
tcattaaaat ataaattata a                                                      2001

<210> SEQ ID NO 6
<211> LENGTH: 666
<212> TYPE: PRT
<213> ORGANISM: Bacteroides thetaiotaomicron

<400> SEQUENCE: 6

Met Asn Lys Thr Leu Lys Tyr Ile Val Leu Thr Phe Ala Cys Phe
1               5                   10                  15

Val Gly Lys Gly Tyr Ala Gln Glu Leu Lys Ser Glu Val Phe Ser Leu
            20                  25                  30

Leu Asn Leu Asp Tyr Pro Gly Leu Glu Lys Val Lys Ala Leu His Gln
        35                  40                  45

Glu Gly Lys Asp Glu Asp Ala Ala Lys Ala Leu Leu Asp Tyr Tyr Arg
    50                  55                  60

Ala Arg Thr Asn Val Lys Thr Pro Asp Ile Asn Leu Lys Lys Ile Thr
65                  70                  75                  80

Ile Gly Lys Glu Glu Gln Gln Trp Ala Asp Asp Gly Leu Lys His Thr
                85                  90                  95

Phe Phe Val His Lys Gly Tyr Gln Pro Ser Tyr Asn Tyr Gly Glu Asp
            100                 105                 110

Ile Asn Trp Gln Tyr Trp Pro Val Lys Asp Asn Glu Leu Arg Trp Gln
        115                 120                 125

Leu His Arg His Lys Trp Phe Thr Pro Met Gly Lys Ala Tyr Arg Val
    130                 135                 140

Ser Gly Asp Glu Lys Tyr Ala Lys Glu Trp Ala Tyr Gln Tyr Ile Asp
145                 150                 155                 160

Trp Ile Lys Lys Asn Pro Leu Val Lys Met Asp Lys Lys Glu Tyr Glu
                165                 170                 175

Leu Val Ser Asp Gly Lys Ile Lys Gly Glu Val Glu Asn Val Arg Phe
            180                 185                 190

Ala Trp Arg Pro Leu Glu Val Ser Asn Arg Leu Gln Asp Gln Thr Thr
        195                 200                 205

Gln Phe Gln Leu Phe Leu Pro Ser Pro Ser Phe Thr Pro Asp Phe Leu
    210                 215                 220

Thr Glu Phe Leu Val Asn Tyr His Lys His Ala Val His Ile Leu Ala
225                 230                 235                 240

Asn Tyr Ser Asp Gln Gly Asn His Leu Leu Phe Glu Ala Gln Arg Met
                245                 250                 255

Ile Tyr Ala Gly Ala Phe Phe Pro Glu Phe Lys Glu Ala Pro Ala Trp
            260                 265                 270

Arg Lys Ser Gly Ile Asp Ile Leu Asn Arg Glu Val Asn Val Gln Val
        275                 280                 285

Tyr Asn Asp Gly Gly Gln Phe Glu Leu Asp Pro His Tyr His Leu Ala
    290                 295                 300

Ala Ile Asn Ile Phe Cys Lys Ala Leu Gly Ile Ala Asp Val Asn Gly
305                 310                 315                 320

Phe Arg Asn Glu Phe Pro Gln Glu Tyr Leu Asp Thr Ile Glu Lys Met
                325                 330                 335

Ile Met Phe Tyr Ala Asn Ile Ser Phe Pro Asp Tyr Thr Asn Pro Cys
            340                 345                 350

Phe Ser Asp Ala Lys Ile Thr Glu Lys Lys Glu Met Leu Lys Asn Tyr
        355                 360                 365

```
Arg Ala Trp Ser Lys Leu Phe Pro Lys Asn Glu Thr Ile Lys Tyr Leu
    370                 375                 380

Ala Thr Asp Gly Lys Glu Gly Ala Leu Pro Asp Tyr Met Ser Lys Gly
385                 390                 395                 400

Phe Leu Lys Ser Gly Phe Phe Val Phe Arg Asn Ser Trp Gly Met Asp
                405                 410                 415

Ala Thr Gln Met Val Val Lys Ala Gly Pro Lys Gly Phe Trp His Cys
            420                 425                 430

Gln Pro Asp Asn Gly Thr Phe Glu Met Trp Phe Asn Gly Lys Asn Leu
        435                 440                 445

Phe Pro Asp Ser Gly Ser Tyr Val Tyr Ala Gly Glu Gly Glu Val Met
    450                 455                 460

Glu Gln Arg Asn Trp His Arg Gln Thr Ser Val His Asn Thr Val Thr
465                 470                 475                 480

Leu Asp Asn Lys Asn Leu Glu Thr Thr Glu Ser Val Thr Lys Leu Trp
                485                 490                 495

Gln Pro Glu Gly Asn Ile Gln Thr Leu Val Thr Glu Asn Pro Ser Tyr
            500                 505                 510

Lys Asn Phe Lys His Arg Arg Ser Val Phe Phe Val Asp Asn Thr Tyr
        515                 520                 525

Phe Val Ile Val Asp Glu Val Ser Gly Ser Ala Lys Gly Ser Val Asn
    530                 535                 540

Leu His Tyr Gln Met Pro Lys Gly Glu Ile Ala Asn Ser Arg Glu Asp
545                 550                 555                 560

Met Thr Phe Leu Thr Gln Phe Glu Asp Gly Ser Asn Met Lys Leu Gln
                565                 570                 575

Cys Phe Gly Pro Glu Gly Met Ser Met Lys Lys Glu Pro Gly Trp Cys
            580                 585                 590

Ser Thr Ala Tyr Arg Lys Arg Tyr Lys Arg Met Asn Val Ser Phe Asn
        595                 600                 605

Val Lys Lys Asp Asn Glu Asn Ala Val Arg Tyr Ile Thr Val Ile Tyr
    610                 615                 620

Pro Val Lys Lys Ser Ala Asp Ala Pro Lys Phe Asp Ala Lys Phe Lys
625                 630                 635                 640

Asn Lys Thr Phe Asp Glu Asn Gly Leu Glu Ile Glu Val Lys Val Asn
                645                 650                 655

Gly Lys Lys Gln Ser Leu Lys Tyr Lys Leu
            660                 665

<210> SEQ ID NO 7
<211> LENGTH: 1935
<212> TYPE: DNA
<213> ORGANISM: Bacteroides thetaiotaomicron

<400> SEQUENCE: 7
caagagttga aaagcgaggt attctcgctt ctcaacctgg actacccggg attggagaaa      60
gtaaaagcct acatcagga aggcaaagat gaggatgccg caaaagcact gctcgactac     120
taccgtgcac gtacgaatgt gaagacgccg gatattaatc tgaaaaagat cactatcggc     180
aaagaagaac agcaatgggc ggatgacgga ttgaagcata cattctttgt tcacaaaggc     240
tatcagcctt cttacaacta cggagaagat atcaactggc aatactggcc ggtgaaagac     300
aatgaactcc gctggcagtt gcaccgtcat aaatggttta ctccgatggg taaggcatac     360
cgtgtatcgg gtgacgagaa atatgccaaa gaatgggcat accaatacat cgactggatt     420
```

```
aaaagaatc cgttggtgaa gatggacaag aaagaatacg aactggtaag tgacggtaag      480
attaaaggcg aagtggaaaa tgtacgtttc gcatggcgtc cgctggaagt cagtaatcgt      540
ctgcaggatc agactaccca gttccagttg ttcctcccct ctccttcttt cactccggat      600
ttcctgactg aatttctggt gaactatcat aaacatgccg tacatattct ggctaattac      660
tctgatcagg gtaatcactt gttgttcgaa gcccagcgta tgatttatgc aggtgcattc      720
ttcccggaat ttaagaagc tccggcctgg agaaaaagcg gtatcgacat tctgaaccgt      780
gaagtaaacg tacaggttta caacgatggc ggccagtttg aacttgaccc gcattatcat      840
cttgctgcta tcaatatctt ctgcaaggca ttgggtatcg cggatgttaa cggattccgt      900
aatgagttcc cacaggaata tctggatact atcgaaaaga tgatcatgtt ctatgccaat      960
atttctttcc cggattacac aaatccgtgt ttcagtgatg ctaaaatcac agaaaagaaa     1020
gaaatgctga agaactatcg tgcatggagc aaactgttcc cgaaaaacga aactatcaag     1080
tatttggcaa cagacggcaa agaaggcgcg ttacccgatt atatgtcgaa aggtttcctg     1140
aaatcaggtt tctttgtgtt ccgcaattcc tggggaatgg atgctacaca atggtagta     1200 aaagccggtc cgaaaggttt ctggcactgt cagccggata acggtacttt cgaaatgtgg     1260
tttaacggca agaacctgtt cccagactcc ggttcgtatg tgtatgccgg tgaaggcgaa     1320
gtgatggaac aacgcaactg catcgtcag acttccgtac acaacaccgt gactctggac     1380
aataagaatc tggaaacaac cgaatctgtt actaaactgt ggcagccgga aggcaatatc     1440
cagaccttgg ttacagaaaa cccaagctac aagaacttca gcaccgccg ttcggtcttc     1500 ttcgtagaca atacctactt tgtcattgta gatgaagtat caggcagcgc caaaggttct     1560
gtcaacctgc actatcagat gccgaaaggt gagatagcca cagccgtga agacatgaca     1620 ttcctgactc aattcgaaga tggaagcaac atgaaacttc aatgcttcgg ccctgaaggc     1680
atgagcatga aaaagagcc gggatggtgt tctactgcat atcgcaagcg ctacaaacgt     1740
atgaatgttt cattcaacgt aaagaaagac aatgagaatg cggtacgtta catcacagtt     1800
atttacccag tcaagaagag cgcagatgcc cctaaatttg acgctaagtt caagaacaaa     1860
acgttcgatg aaaacggact ggaaatagaa gtgaaagtaa acgcaagaa acagtcatta     1920 aaatataaat tataa                                                     1935
```

<210> SEQ ID NO 8
<211> LENGTH: 644
<212> TYPE: PRT
<213> ORGANISM: Bacteroides thetaiotaomicron

<400> SEQUENCE: 8

```
Gln Glu Leu Lys Ser Glu Val Phe Ser Leu Leu Asn Leu Asp Tyr Pro
 1               5                  10                  15

Gly Leu Glu Lys Val Lys Ala Leu His Gln Glu Gly Lys Asp Glu Asp
                20                  25                  30

Ala Ala Lys Ala Leu Leu Asp Tyr Tyr Arg Ala Arg Thr Asn Val Lys
            35                  40                  45

Thr Pro Asp Ile Asn Leu Lys Lys Ile Thr Ile Gly Lys Glu Glu Gln
        50                  55                  60

Gln Trp Ala Asp Asp Gly Leu Lys His Thr Phe Val His Lys Gly
 65                  70                  75                  80

Tyr Gln Pro Ser Tyr Asn Tyr Gly Glu Asp Ile Asn Trp Gln Tyr Trp
                85                  90                  95
```

-continued

```
Pro Val Lys Asp Asn Glu Leu Arg Trp Gln Leu His Arg His Lys Trp
            100                 105                 110
Phe Thr Pro Met Gly Lys Ala Tyr Arg Val Ser Gly Asp Glu Lys Tyr
            115                 120                 125
Ala Lys Glu Trp Ala Tyr Gln Tyr Ile Asp Trp Ile Lys Lys Asn Pro
        130                 135                 140
Leu Val Lys Met Asp Lys Lys Glu Tyr Glu Leu Val Ser Asp Gly Lys
145                 150                 155                 160
Ile Lys Gly Glu Val Glu Asn Val Arg Phe Ala Trp Arg Pro Leu Glu
                165                 170                 175
Val Ser Asn Arg Leu Gln Asp Gln Thr Thr Gln Phe Gln Leu Phe Leu
            180                 185                 190
Pro Ser Pro Ser Phe Thr Pro Asp Phe Leu Thr Glu Phe Leu Val Asn
        195                 200                 205
Tyr His Lys His Ala Val His Ile Leu Ala Asn Tyr Ser Asp Gln Gly
    210                 215                 220
Asn His Leu Leu Phe Glu Ala Gln Arg Met Ile Tyr Ala Gly Ala Phe
225                 230                 235                 240
Phe Pro Glu Phe Lys Glu Ala Pro Ala Trp Arg Lys Ser Gly Ile Asp
                245                 250                 255
Ile Leu Asn Arg Glu Val Asn Val Gln Val Tyr Asn Asp Gly Gly Gln
            260                 265                 270
Phe Glu Leu Asp Pro His Tyr His Leu Ala Ala Ile Asn Ile Phe Cys
        275                 280                 285
Lys Ala Leu Gly Ile Ala Asp Val Asn Gly Phe Arg Asn Glu Phe Pro
    290                 295                 300
Gln Glu Tyr Leu Asp Thr Ile Glu Lys Met Ile Met Phe Tyr Ala Asn
305                 310                 315                 320
Ile Ser Phe Pro Asp Tyr Thr Asn Pro Cys Phe Ser Asp Ala Lys Ile
                325                 330                 335
Thr Glu Lys Lys Glu Met Leu Lys Asn Tyr Arg Ala Trp Ser Lys Leu
            340                 345                 350
Phe Pro Lys Asn Glu Thr Ile Lys Tyr Leu Ala Thr Asp Gly Lys Glu
        355                 360                 365
Gly Ala Leu Pro Asp Tyr Met Ser Lys Gly Phe Leu Lys Ser Gly Phe
    370                 375                 380
Phe Val Phe Arg Asn Ser Trp Gly Met Asp Ala Thr Gln Met Val Val
385                 390                 395                 400
Lys Ala Gly Pro Lys Gly Phe Trp His Cys Gln Pro Asp Asn Gly Thr
                405                 410                 415
Phe Glu Met Trp Phe Asn Gly Lys Asn Leu Phe Pro Asp Ser Gly Ser
            420                 425                 430
Tyr Val Tyr Ala Gly Glu Gly Glu Val Met Glu Gln Arg Asn Trp His
        435                 440                 445
Arg Gln Thr Ser Val His Asn Thr Val Thr Leu Asp Asn Lys Asn Leu
    450                 455                 460
Glu Thr Thr Glu Ser Val Thr Lys Leu Trp Gln Pro Glu Gly Asn Ile
465                 470                 475                 480
Gln Thr Leu Val Thr Glu Asn Pro Ser Tyr Lys Asn Phe Lys His Arg
                485                 490                 495
Arg Ser Val Phe Phe Val Asp Asn Thr Tyr Phe Val Ile Val Asp Glu
            500                 505                 510
Val Ser Gly Ser Ala Lys Gly Ser Val Asn Leu His Tyr Gln Met Pro
```

-continued

```
           515                 520                 525
Lys Gly Glu Ile Ala Asn Ser Arg Glu Asp Met Thr Phe Leu Thr Gln
            530                 535                 540

Phe Glu Asp Gly Ser Asn Met Lys Leu Gln Cys Phe Gly Pro Glu Gly
545                 550                 555                 560

Met Ser Met Lys Lys Glu Pro Gly Trp Cys Ser Thr Ala Tyr Arg Lys
                565                 570                 575

Arg Tyr Lys Arg Met Asn Val Ser Phe Asn Val Lys Lys Asp Asn Glu
            580                 585                 590

Asn Ala Val Arg Tyr Ile Thr Val Ile Tyr Pro Val Lys Lys Ser Ala
            595                 600                 605

Asp Ala Pro Lys Phe Asp Ala Lys Phe Lys Asn Lys Thr Phe Asp Glu
            610                 615                 620

Asn Gly Leu Glu Ile Glu Val Lys Val Asn Gly Lys Lys Gln Ser Leu
625                 630                 635                 640

Lys Tyr Lys Leu

<210> SEQ ID NO 9
<211> LENGTH: 1947
<212> TYPE: DNA
<213> ORGANISM: Bacteroides thetaiotaomicron

<400> SEQUENCE: 9
atgaataaaa ccctgaaata tatcgtcctg ctgacatttg cttgtttcgt aggcaaaggc       60
tatgcccaag agttgaaaag cgaggtattc tcgcttctca acctggacta ccccggattg      120
gagaaagtaa aagccttaca tcaggaaggc aaagatgagg atgccgcaaa agcactgctc      180
gactactacc gtgcacgtac gaatgtgaag acgccggata ttaatctgaa aaagatcact      240
atcggcaaag aagaacagca atgggcggat gacggattga agcatacatt ctttgttcac      300
aaaggctatc agccttctta caactacgga gaagatatca actggcaata ctggccggtg      360
aaagacaatg aactccgctg gcagttgcac cgtcataaat ggtttactcc gatgggtaag      420
gcataccgtg tatcgggtga cgagaaatat gccaaagaat gggcatacca atacatcgac      480
tggattaaaa agaatccgtt ggtggtggaa aatgtacgtt tcgcatggcg tccgctggaa      540
gtcagtaatc gtctgcagga tcagactacc cagttccagt tgttcctccc ctctccttct      600
ttcactccgg atttcctgac tgaatttctg gtgaactatc ataaacatgc cgtacatatt      660
ctggctaatt actctgatca gggtaatcac ttgttgttcg aagcccagcg tatgatttat      720
gcaggtgcat tcttcccgga atttaaagaa gctccggcct ggagaaaaag cggtatcgac      780
attctgaacc gtgaagtaaa cgtacaggtt acaacgatg cggccagtt tgaacttgac      840
ccgcattatc atcttgctgc tatcaatatc ttctgcaagg cattgggtat cgcggatgtt      900
aacggattcc gtaatgagtt cccacaggaa tatctggata ctatcgaaaa gatgatcatg      960
ttctatgcca atatttcttt cccggattac acaaatccgt gtttcagtga tgctaaaatc     1020
acagaaaaga aagaaatgct gaagaactat cgtgcatgga gcaaactgtt cccgaaaaac     1080
gaaactatca agtatttggc aacagacggc aaagaaggcg cgttacccga ttatatgtcg     1140
aaaggttttcc tgaaatcagg tttctttgtg ttccgcaatt cctggggaat ggatgctaca     1200
caaatggtag taaaagccgg tccgaaaggt ttctggcact gtcagccgga taacggtact     1260
ttcgaaatgt ggtttaacgg caagaacctg ttcccagact ccggttcgta tgtgtatgcc     1320
ggtgaaggcg aagtgatgga acaacgcaac tggcatcgtc agacttccgt acacaacacc     1380
```

-continued

```
gtgactctgg acaataagaa tctggaaaca accgaatctg ttactaaact gtggcagccg   1440
gaaggcaata tccagacctt ggttacagaa aacccaagct acaagaactt caagcaccgc   1500
cgttcggtct tcttcgtaga caataccrac tttgtcattg tagatgaagt atcaggcagc   1560
gccaaaggtt ctgtcaacct gcactatcag atgccgaaag gtgagatagc aacagccgt    1620 gaagacatga cattcctgac tcaattcgaa gatggaagca acatgaaact tcaatgcttc   1680
ggccctgaag gcatgagcat gaaaaaagag ccgggatggt gttctactgc atatcgcaag   1740
cgctacaaac gtatgaatgt ttcattcaac gtaaagaaag acaatgagaa tgcggtacgt   1800
tacatcacag ttatttaccc agtcaagaag agcgcagatg ccctaaatt tgacgctaag   1860 ttcaagaaca aacgttcga tgaaaacgga ctggaaatag aagtgaaagt aaacggcaag   1920
aaacagtcat taaatataa attataa                                       1947
```

<210> SEQ ID NO 10
<211> LENGTH: 649
<212> TYPE: PRT
<213> ORGANISM: Bacteroides thetaiotaomicron

<400> SEQUENCE: 10

```
Met Asn Lys Thr Leu Lys Tyr Ile Val Leu Leu Thr Phe Ala Cys Phe
  1               5                  10                  15

Val Gly Lys Gly Tyr Ala Gln Glu Leu Lys Ser Glu Val Phe Ser Leu
             20                  25                  30

Leu Asn Leu Asp Tyr Pro Gly Leu Glu Lys Val Lys Ala Leu His Gln
         35                  40                  45

Glu Gly Lys Asp Glu Asp Ala Ala Lys Ala Leu Leu Asp Tyr Tyr Arg
     50                  55                  60

Ala Arg Thr Asn Val Lys Thr Pro Asp Ile Asn Leu Lys Lys Ile Thr
 65                  70                  75                  80

Ile Gly Lys Glu Glu Gln Gln Trp Ala Asp Asp Gly Leu Lys His Thr
                 85                  90                  95

Phe Phe Val His Lys Gly Tyr Gln Pro Ser Tyr Asn Tyr Gly Glu Asp
            100                 105                 110

Ile Asn Trp Gln Tyr Trp Pro Val Lys Asp Asn Glu Leu Arg Trp Gln
        115                 120                 125

Leu His Arg His Lys Trp Phe Thr Pro Met Gly Lys Ala Tyr Arg Val
    130                 135                 140

Ser Gly Asp Glu Lys Tyr Ala Lys Glu Trp Ala Tyr Gln Tyr Ile Asp
145                 150                 155                 160

Trp Ile Lys Lys Asn Pro Leu Val Val Glu Asn Val Arg Phe Ala Trp
                165                 170                 175

Arg Pro Leu Glu Val Ser Asn Arg Leu Gln Asp Gln Thr Thr Gln Phe
            180                 185                 190

Gln Leu Phe Leu Pro Ser Pro Ser Phe Thr Pro Asp Phe Leu Thr Glu
        195                 200                 205

Phe Leu Val Asn Tyr His Lys His Ala Val His Ile Leu Ala Asn Tyr
    210                 215                 220

Ser Asp Gln Gly Asn His Leu Leu Phe Glu Ala Gln Arg Met Ile Tyr
225                 230                 235                 240

Ala Gly Ala Phe Phe Pro Glu Phe Lys Glu Ala Pro Ala Trp Arg Lys
                245                 250                 255

Ser Gly Ile Asp Ile Leu Asn Arg Glu Val Asn Val Gln Val Tyr Asn
            260                 265                 270
```

```
Asp Gly Gly Gln Phe Glu Leu Asp Pro His Tyr His Leu Ala Ala Ile
            275                 280                 285

Asn Ile Phe Cys Lys Ala Leu Gly Ile Ala Asp Val Asn Gly Phe Arg
        290                 295                 300

Asn Glu Phe Pro Gln Glu Tyr Leu Asp Thr Ile Glu Lys Met Ile Met
305                 310                 315                 320

Phe Tyr Ala Asn Ile Ser Phe Pro Asp Tyr Thr Asn Pro Cys Phe Ser
                325                 330                 335

Asp Ala Lys Ile Thr Glu Lys Lys Glu Met Leu Lys Asn Tyr Arg Ala
            340                 345                 350

Trp Ser Lys Leu Phe Pro Lys Asn Glu Thr Ile Lys Tyr Leu Ala Thr
            355                 360                 365

Asp Gly Lys Glu Gly Ala Leu Pro Asp Tyr Met Ser Lys Gly Phe Leu
            370                 375                 380

Lys Ser Gly Phe Phe Val Phe Arg Asn Ser Trp Gly Met Asp Ala Thr
385                 390                 395                 400

Gln Met Val Val Lys Ala Gly Pro Lys Gly Phe Trp His Cys Gln Pro
                405                 410                 415

Asp Asn Gly Thr Phe Glu Met Trp Phe Asn Gly Lys Asn Leu Phe Pro
            420                 425                 430

Asp Ser Gly Ser Tyr Val Tyr Ala Gly Glu Gly Glu Val Met Glu Gln
            435                 440                 445

Arg Asn Trp His Arg Gln Thr Ser Val His Asn Thr Val Thr Leu Asp
            450                 455                 460

Asn Lys Asn Leu Glu Thr Thr Glu Ser Val Thr Lys Leu Trp Gln Pro
465                 470                 475                 480

Glu Gly Asn Ile Gln Thr Leu Val Thr Glu Asn Pro Ser Tyr Lys Asn
                485                 490                 495

Phe Lys His Arg Arg Ser Val Phe Val Asp Asn Thr Tyr Phe Val
            500                 505                 510

Ile Val Asp Glu Val Ser Gly Ser Ala Lys Gly Ser Val Asn Leu His
            515                 520                 525

Tyr Gln Met Pro Lys Gly Glu Ile Ala Asn Ser Arg Glu Asp Met Thr
            530                 535                 540

Phe Leu Thr Gln Phe Glu Asp Gly Ser Asn Met Lys Leu Gln Cys Phe
545                 550                 555                 560

Gly Pro Glu Gly Met Ser Met Lys Lys Glu Pro Gly Trp Cys Ser Thr
                565                 570                 575

Ala Tyr Arg Lys Arg Tyr Lys Arg Met Asn Val Ser Phe Asn Val Lys
            580                 585                 590

Lys Asp Asn Glu Asn Ala Val Arg Tyr Ile Thr Val Ile Tyr Pro Val
            595                 600                 605

Lys Lys Ser Ala Asp Ala Pro Lys Phe Asp Ala Lys Phe Lys Asn Lys
            610                 615                 620

Thr Phe Asp Glu Asn Gly Leu Glu Ile Glu Val Lys Val Asn Gly Lys
625                 630                 635                 640

Lys Gln Ser Leu Lys Tyr Lys Leu Leu
                645

<210> SEQ ID NO 11
<211> LENGTH: 29
<212> TYPE: DNA
<213> ORGANISM: Artificial Sequence
<220> FEATURE:
<223> OTHER INFORMATION: Primer
```

<400> SEQUENCE: 11
catatgctga ctgctcagac taaaaatac                                    29

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
ctcgagttat ctttccgaat atcctgcgag at                                32

<210> SEQ ID NO 13
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 13

Met Gly Ser Ser His His His His His His Ser Ser Gly Leu Val Pro
 1               5                  10                  15

Arg Gly Ser His
            20

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
catatgaata aaaccctgaa atatatcgtc ctg                               33

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
ctcgagttat aatttatatt ttaatgactg tttcttgc                          38

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
catatgcaag agttgaaaag cgaggtattc tcg                               33

<210> SEQ ID NO 17
<211> LENGTH: 40
<212> TYPE: PRT
<213> ORGANISM: Artificial Sequence
<220> FEATURE:
<223> OTHER INFORMATION: Synthetically generated peptide

<400> SEQUENCE: 17

-continued

```
Met Gly Ser Ser His His His His His Ser Ser Gly Leu Val Pro
1               5                   10                  15

Arg Gly Ser His Met Asn Lys Thr Leu Lys Tyr Lys Val Asn Gly Lys
                20                  25                  30

Lys Gln Ser Leu Lys Tyr Lys Leu
        35                  40

<210> SEQ ID NO 18
<211> LENGTH: 42
<212> TYPE: PRT
<213> ORGANISM: Artificial Sequence
<220> FEATURE:
<223> OTHER INFORMATION: Synthetically generated peptide

<400> SEQUENCE: 18

Met Gly Ser Ser His His His His His Ser Ser Gly Leu Val Pro
1               5                   10                  15

Arg Gly Ser His Met Gln Glu Leu Lys Ser Glu Val Phe Lys Val Asn
                20                  25                  30

Gly Lys Lys Gln Ser Leu Lys Tyr Lys Leu
        35                  40

<210> SEQ ID NO 19
<211> LENGTH: 18
<212> TYPE: PRT
<213> ORGANISM: Bacteroides thetaiotaomicron

<400> SEQUENCE: 19

Lys Met Asp Lys Lys Glu Tyr Glu Leu Val Ser Asp Gly Lys Ile Lys
1               5                   10                  15

Gly Glu

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
ggattaaaaa gaatccgttg gtggaaaatg tacgtttcgc                    40

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
cctaattttt cttaggcaac caccttttac atgcaaagcg                    40

<210> SEQ ID NO 22
<211> LENGTH: 1104
<212> TYPE: DNA
<213> ORGANISM: Bacteroides thetaiotaomicron

<400> SEQUENCE: 22
caaacactga tgccactcac cgaacgggta acgtacagg ctgactctgc acgtatcaac    60
cagattattg acggttgctg ggtagctgtc gggacgaata aacctcatgc cattcagcgt   120
gattttacca acctgtttga tgcaagccc tcctatcgct ttgaactcaa aactgaagac   180
```

```
aatacactgg aaggttatgc gaaaggagaa acgaaaggac gtgccgagtt tcatattgc    240 tatgcaactt ccgacgattt caggggatta cctgccgacg tttatcagaa agcacagatc   300
acaaagacag tttatcatca cgggaaggga gcttgtccgc aaggaagttc ccgcgactat   360
gagttttcgg tttatattcc ttcttcttta gacagcaatg tctccaccat ctttgcccaa   420
tggcacggaa tgcccgaccg gacgctggtc cagactcctc agggcgaggt gaagaaactg   480
actgttgacg aatttgtaga actggaaaaa acgaccttct tcaaaaagaa tgtcggacac   540
gaaaaagtgg ccagactgga taaacaaggt aatccggtga agataaaaa tggaaaacct    600 gtatataagg caggaaaacc caacggatgg ttggttgaac agggaggata cccgccattg   660
gcattcggat tttccggagg actgttttat atcaaagcaa actccgaccg taaatggctg   720
acagacaaag atgaccgttg caatgcaaac ccgggaaaga cgcccgttat gaaaccgctg   780
acttctgaat acaaggcatc caccattgcc tacaaattac cttttgccga tttcccgaaa   840
gactgctgga ttacttttccg tgtccatatc gactggacgg tctatggcaa ggaagcggaa   900
acgattgtga aaccgggcat gctggatgta cggatggatt atcaggagca aggtaagaaa   960
gtgagcaaac acattgtcga taatgagaag attctgattg gacgtaacga cgaagacggg  1020
tattacttta gttcggaatt ttaccgcgta ggtgatagta ccgttcccgt ttgctacaat  1080
ctcgcaggat attcggaaag ataa                                        1104
```

<210> SEQ ID NO 23
<211> LENGTH: 367
<212> TYPE: PRT
<213> ORGANISM: Bacteroides thetaiotaomicron

<400> SEQUENCE: 23

```
Gln Thr Leu Met Pro Leu Thr Glu Arg Val Asn Val Gln Ala Asp Ser
  1               5                  10                  15

Ala Arg Ile Asn Gln Ile Ile Asp Gly Cys Trp Val Ala Val Gly Thr
             20                  25                  30

Asn Lys Pro His Ala Ile Gln Arg Asp Phe Thr Asn Leu Phe Asp Gly
         35                  40                  45

Lys Pro Ser Tyr Arg Phe Glu Leu Lys Thr Glu Asp Asn Thr Leu Glu
     50                  55                  60

Gly Tyr Ala Lys Gly Glu Thr Lys Gly Arg Ala Glu Phe Ser Tyr Cys
 65                  70                  75                  80

Tyr Ala Thr Ser Asp Asp Phe Arg Gly Leu Pro Ala Asp Val Tyr Gln
                 85                  90                  95

Lys Ala Gln Ile Thr Lys Thr Val Tyr His His Gly Lys Gly Ala Cys
            100                 105                 110

Pro Gln Gly Ser Ser Arg Asp Tyr Glu Phe Ser Val Tyr Ile Pro Ser
        115                 120                 125

Ser Leu Asp Ser Asn Val Ser Thr Ile Phe Ala Gln Trp His Gly Met
    130                 135                 140

Pro Asp Arg Thr Leu Val Gln Thr Pro Gln Gly Glu Val Lys Lys Leu
145                 150                 155                 160

Thr Val Asp Glu Phe Val Glu Leu Glu Lys Thr Thr Phe Phe Lys Lys
                165                 170                 175

Asn Val Gly His Glu Lys Val Ala Arg Leu Asp Lys Gln Gly Asn Pro
            180                 185                 190

Val Lys Asp Lys Asn Gly Lys Pro Val Tyr Lys Ala Gly Lys Pro Asn
        195                 200                 205
```

```
Gly Trp Leu Val Glu Gln Gly Tyr Pro Pro Leu Ala Phe Gly Phe
210                 215                 220

Ser Gly Gly Leu Phe Tyr Ile Lys Ala Asn Ser Asp Arg Lys Trp Leu
225                 230                 235                 240

Thr Asp Lys Asp Asp Arg Cys Asn Ala Asn Pro Gly Lys Thr Pro Val
                245                 250                 255

Met Lys Pro Leu Thr Ser Glu Tyr Lys Ala Ser Thr Ile Ala Tyr Lys
            260                 265                 270

Leu Pro Phe Ala Asp Phe Pro Lys Asp Cys Trp Ile Thr Phe Arg Val
            275                 280                 285

His Ile Asp Trp Thr Val Tyr Gly Lys Glu Ala Glu Thr Ile Val Lys
            290                 295                 300

Pro Gly Met Leu Asp Val Arg Met Asp Tyr Gln Glu Gln Gly Lys Lys
305                 310                 315                 320

Val Ser Lys His Ile Val Asp Asn Glu Lys Ile Leu Ile Gly Arg Asn
                325                 330                 335

Asp Glu Asp Gly Tyr Tyr Phe Lys Phe Gly Ile Tyr Arg Val Gly Asp
                340                 345                 350

Ser Thr Val Pro Val Cys Tyr Asn Leu Ala Gly Tyr Ser Glu Arg
                355                 360                 365

<210> SEQ ID NO 24
<211> LENGTH: 384
<212> TYPE: PRT
<213> ORGANISM: Pedobacter heparinus

<400> SEQUENCE: 24

Met Lys Lys Gln Ile Leu Tyr Leu Ile Val Leu Gln Gln Leu Phe Leu
1               5                   10                  15

Cys Ser Ala Tyr Ala Gln Gln Lys Lys Ser Gly Asn Ile Pro Tyr Arg
            20                  25                  30

Val Asn Val Gln Ala Asp Ser Ala Lys Gln Lys Ala Ile Ile Asp Asn
        35                  40                  45

Lys Trp Val Ala Val Gly Ile Asn Lys Pro Tyr Ala Leu Gln Tyr Asp
50                  55                  60

Asp Lys Leu Arg Phe Asn Gly Lys Pro Ser Tyr Arg Phe Glu Leu Lys
65                  70                  75                  80

Ala Glu Asp Asn Ser Leu Glu Gly Tyr Ala Ala Gly Glu Thr Lys Gly
                85                  90                  95

Arg Thr Glu Leu Ser Tyr Ser Tyr Ala Thr Thr Asn Asp Phe Lys Lys
            100                 105                 110

Phe Pro Pro Ser Val Tyr Gln Asn Ala Gln Lys Leu Lys Thr Val Tyr
        115                 120                 125

His Tyr Gly Lys Gly Ile Cys Glu Gln Gly Ser Ser Arg Ser Tyr Thr
130                 135                 140

Phe Ser Val Tyr Ile Pro Ser Ser Phe Pro Asp Asn Ala Thr Thr Ile
145                 150                 155                 160

Phe Ala Gln Trp His Gly Ala Pro Ser Arg Thr Leu Val Ala Thr Pro
                165                 170                 175

Glu Gly Glu Ile Lys Thr Leu Ser Ile Glu Glu Phe Leu Ala Leu Tyr
            180                 185                 190

Asp Arg Met Ile Phe Lys Lys Asn Ile Ala His Asp Lys Val Glu Lys
        195                 200                 205

Lys Asp Lys Asp Gly Lys Ile Thr Tyr Val Ala Gly Lys Pro Asn Gly
210                 215                 220
```

Trp Lys Val Glu Gln Gly Gly Tyr Pro Thr Leu Ala Phe Gly Phe Ser
225                 230                 235                 240

Lys Gly Tyr Phe Tyr Ile Lys Ala Asn Ser Asp Arg Gln Trp Leu Thr
            245                 250                 255

Asp Lys Ala Asp Arg Asn Asn Ala Asn Pro Glu Asn Ser Glu Val Met
        260                 265                 270

Lys Pro Tyr Ser Ser Glu Tyr Lys Thr Ser Thr Ile Ala Tyr Lys Met
    275                 280                 285

Pro Phe Ala Gln Phe Pro Lys Asp Cys Trp Ile Thr Phe Asp Val Ala
290                 295                 300

Ile Asp Trp Thr Lys Tyr Gly Lys Glu Ala Asn Thr Ile Leu Lys Pro
305                 310                 315                 320

Gly Lys Leu Asp Val Met Met Thr Tyr Thr Lys Asn Lys Lys Pro Gln
            325                 330                 335

Lys Ala His Ile Val Asn Gln Gln Glu Ile Leu Ile Gly Arg Asn Asp
        340                 345                 350

Asp Asp Gly Tyr Tyr Phe Lys Phe Gly Ile Tyr Arg Val Gly Asn Ser
    355                 360                 365

Thr Val Pro Val Thr Tyr Asn Leu Ser Gly Tyr Ser Glu Thr Ala Arg
370                 375                 380

<210> SEQ ID NO 25
<211> LENGTH: 659
<212> TYPE: PRT
<213> ORGANISM: Pedobacter heparinus

<400> SEQUENCE: 25

Met Thr Thr Lys Ile Phe Lys Arg Ile Ile Val Phe Ala Val Ile Ala
1               5                   10                  15

Leu Ser Ser Gly Asn Ile Leu Ala Gln Ser Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Lys Ala Leu Leu
50                  55                  60

Ala Tyr Tyr Arg Glu Lys Ser Lys Ala Arg Glu Pro Asp Phe Ser Asn
65                  70                  75                  80

Ala Glu Lys Pro Ala Asp Ile Arg Gln Pro Ile Asp Lys Val Thr Arg
            85                  90                  95

Glu Met Ala Asp Lys Ala Leu Val His Gln Phe Gln Pro His Lys Gly
        100                 105                 110

Tyr Gly Tyr Phe Asp Tyr Gly Lys Asp Ile Asn Trp Gln Met Trp Pro
    115                 120                 125

Val Lys Asp Asn Glu Val Arg Trp Gln Leu His Arg Val Lys Trp Trp
130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
            165                 170                 175

Gly Leu Ser Gln Asp Asn Asp Lys Phe Val Trp Arg Pro Leu Glu Val
        180                 185                 190

Ser Asp Arg Val Gln Ser Leu Pro Pro Thr Phe Ser Leu Phe Val Asn
    195                 200                 205

Ser Pro Ala Phe Thr Pro Ala Phe Leu Met Glu Phe Leu Asn Ser Tyr

-continued

```
            210                 215                 220
His Gln Gln Ala Asp Tyr Leu Ser Thr His Tyr Ala Glu Gln Gly Asn
225                 230                 235                 240

His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
                260                 265                 270

Leu Asn Thr Glu Ile Lys Lys Gln Val Tyr Ala Asp Gly Met Gln Phe
                275                 280                 285

Glu Leu Ser Pro Ile Tyr His Val Ala Ile Asp Ile Phe Leu Lys
290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
                340                 345                 350

Asp Lys Asn Phe Arg Met Ala Gln Phe Ala Ser Trp Ala Arg Val Phe
                355                 360                 365

Pro Ala Asn Gln Ala Ile Lys Tyr Phe Ala Thr Asp Gly Lys Gln Gly
370                 375                 380

Lys Ala Pro Asn Phe Leu Ser Lys Ala Leu Ser Asn Ala Gly Phe Tyr
385                 390                 395                 400

Thr Phe Arg Ser Gly Trp Asp Lys Asn Ala Thr Val Met Val Leu Lys
                405                 410                 415

Ala Ser Pro Pro Gly Glu Phe His Ala Gln Pro Asp Asn Gly Thr Phe
                420                 425                 430

Glu Leu Phe Ile Lys Gly Arg Asn Phe Thr Pro Asp Ala Gly Val Phe
                435                 440                 445

Val Tyr Ser Gly Asp Glu Ala Ile Met Lys Leu Arg Asn Trp Tyr Arg
                450                 455                 460

Gln Thr Arg Ile His Ser Thr Leu Thr Leu Asp Asn Gln Asn Met Val
465                 470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
                500                 505                 510

Ser Val Leu Phe Ile Asn Lys Lys Tyr Phe Leu Val Ile Asp Arg Ala
                515                 520                 525

Ile Gly Glu Ala Thr Gly Asn Leu Gly Val His Trp Gln Leu Lys Glu
530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Glu Gly Lys Val Ser Tyr Val Tyr Asn Lys
                580                 585                 590

Glu Leu Lys Arg Pro Ala Phe Val Phe Glu Lys Pro Lys Lys Asn Ala
                595                 600                 605

Gly Thr Gln Asn Phe Val Ser Ile Val Tyr Pro Tyr Asp Gly Gln Lys
                610                 615                 620

Ala Pro Glu Ile Ser Ile Arg Glu Asn Lys Gly Asn Asp Phe Glu Lys
625                 630                 635                 640
```

Gly Lys Leu Asn Leu Thr Leu Thr Ile Asn Gly Lys Gln Gln Leu Val
            645                 650                 655

Leu Val Pro

<210> SEQ ID NO 26
<211> LENGTH: 286
<212> TYPE: PRT
<213> ORGANISM: Artificial Sequence
<220> FEATURE:
<223> OTHER INFORMATION: Consensus sequence

<400> SEQUENCE: 26

Met Lys Lys Ile Leu Ile Met Met Gly Cys Arg Val Asn Val Gln Ala
 1               5                  10                  15

Asp Ser Ala Arg Ile Ile Asp Trp Val Ala Gly Asn Lys Pro Ala
             20                  25                  30

Ile Gln Asp Phe Gly Lys Pro Ser Tyr Arg Phe Glu Leu Lys Glu Asp
             35                  40                  45

Asn Thr Leu Glu Gly Tyr Ala Gly Glu Thr Lys Gly Arg Glu Ser Tyr
 50                  55                  60

Tyr Ala Thr Ser Asp Phe Arg Pro Val Tyr Gln Ala Gln Lys Thr Val
 65                  70                  75                  80

Tyr His Gly Lys Gly Cys Gln Gly Ser Ser Arg Tyr Phe Ser Val Tyr
                 85                  90                  95

Ile Pro Ser Ser Asn Ser Thr Ile Phe Ala Gln Trp His Gly Pro Arg
            100                 105                 110

Thr Leu Val Thr Pro Gly Glu Val Lys Leu Thr Val Asp Glu Phe Val
            115                 120                 125

Leu Phe Lys Lys Asn Val Gly His Glu Lys Val Arg Leu Asp Lys Gln
        130                 135                 140

Gly Asn Pro Val Lys Asp Lys Gly Lys Tyr Ala Gly Lys Pro Asn Gly
145                 150                 155                 160

Trp Val Glu Gln Gly Gly Tyr Pro Leu Ala Phe Gly Phe Ser Gly Phe
                165                 170                 175

Tyr Ile Lys Ala Asn Ser Asp Arg Trp Leu Thr Asp Lys Asp Arg Asn
            180                 185                 190

Ala Asn Pro Thr Val Met Lys Pro Thr Ser Glu Tyr Lys Ser Thr Ile
        195                 200                 205

Ala Tyr Lys Ile Pro Phe Ala Phe Pro Lys Asp Cys Trp Ile Thr Phe
    210                 215                 220

Val Ile Asp Trp Thr Tyr Gly Lys Glu Ala Thr Ile Val Lys Pro Gly
225                 230                 235                 240

Leu Asp Val Met Tyr Gln Lys His Ile Val Asn Ile Leu Ile Gly Arg
                245                 250                 255

Asn Asp Glu Asp Gly Tyr Tyr Phe Lys Phe Gly Ile Tyr Arg Val Gly
            260                 265                 270

Ser Thr Val Pro Val Tyr Asn Leu Gly Tyr Ser Glu Ala Arg
        275                 280                 285

<210> SEQ ID NO 27
<211> LENGTH: 388
<212> TYPE: PRT
<213> ORGANISM: Artificial Sequence
<220> FEATURE:
<223> OTHER INFORMATION: Consensus sequence

<400> SEQUENCE: 27

```
Met Lys Lys Ile Ile Val Gly Asn Ile Ala Ile Phe Ile Asn Leu Glu
 1               5                  10                  15

Tyr Gly Leu Glu Lys Val Gly Asp Asp Ala Lys Ala Leu Leu Tyr
            20                  25                  30

Tyr Arg Lys Ser Arg Pro Asp Asn Ala Glu Lys Pro Ala Arg Ile Lys
            35                  40                  45

Ala Asp Ala Leu His Phe His Lys Gly Tyr Pro Phe Tyr Gly Asp Ile
 50                  55                  60

Asn Trp Gln Trp Pro Val Lys Asp Asn Glu Val Arg Trp Gln Leu His
 65                  70                  75                  80

Arg Lys Trp Trp Met Ala Tyr Thr Gly Asp Glu Lys Tyr Ala Arg Glu
                 85                  90                  95

Trp Tyr Gln Tyr Asp Trp Arg Lys Asn Pro Leu Lys Lys Glu Tyr Glu
                100                 105                 110

Leu Val Ser Asp Gly Lys Ile Lys Gly Glu Val Asp Asn Lys Phe Trp
            115                 120                 125

Arg Pro Leu Glu Val Ser Arg Val Gln Phe Leu Phe Val Ser Pro Phe
130                 135                 140

Thr Pro Phe Leu Glu Phe Leu Tyr His Ala Leu Tyr Glu Gln Gly Asn
145                 150                 155                 160

His Leu Phe Glu Ala Gln Arg Leu Phe Ala Gly Phe Pro Glu Phe Lys
                165                 170                 175

Asp Pro Trp Arg Thr Gly Ile Val Leu Asn Glu Ile Gln Val Tyr Asp
                180                 185                 190

Gly Gln Phe Glu Leu Pro Tyr His Val Ala Ala Ile Ile Phe Lys Ala
            195                 200                 205

Gly Ala Glu Phe Pro Gln Tyr Val Thr Val Glu Met Ile Met Ile Ser
210                 215                 220

Pro Asp Tyr Pro Phe Asp Ile Thr Asp Lys Met Gln Phe Trp Arg Val
225                 230                 235                 240

Phe Pro Asn Ile Lys Tyr Ala Thr Asp Gly Lys Gly Pro Phe Leu Ser
                245                 250                 255

Lys Ala Gly Phe Tyr Phe Arg Trp Ala Thr Met Val Ile Lys Ala Pro
                260                 265                 270

Gly Phe His Gln Pro Asp Asn Gly Thr Phe Glu Leu Phe Gly Arg Asn
            275                 280                 285

Pro Asp Gly Phe Val Tyr Gly Asp Ile Met Arg Asn Trp Arg Gln Thr
290                 295                 300

Ile His Thr Ile Thr Leu Asp Asn Asn Met Thr Trp Asn Leu Leu Asn
305                 310                 315                 320

Pro Ser Tyr Asn His Arg Ser Val Phe Ile Tyr Phe Leu Val Ile Asp
                325                 330                 335

Gly Ala Gly Leu Val His Trp Gln Leu Asp Lys Thr Tyr Asp Gly Asn
            340                 345                 350

Leu Ile Gln Asp Ser Leu Glu Gly Ser Tyr Lys Lys Arg Phe Lys Asn
            355                 360                 365

Phe Val Ser Ile Val Tyr Pro Lys Phe Glu Leu Leu Ile Asn Gly
            370                 375                 380

Lys Gln Val Leu
385
```